(12) United States Patent
Zebroski

(10) Patent No.: US 12,043,854 B2
(45) Date of Patent: *Jul. 23, 2024

(54) PROCESSES FOR REDUCING STEAM CONSUMPTION AND IMPROVING PROCESS CARBON BALANCE IN BIOMASS CONVERSION TO SUGARS, BIOCHEMICALS, BIOFUELS, AND/OR BIOMATERIALS

(71) Applicant: GranBio Intellectual Property Holdings, LLC, Minnetrista, MN (US)

(72) Inventor: Ryan Zebroski, Fayetteville, GA (US)

(73) Assignee: GranBio Intellectual Property Holdings, LLC, Minnetrista, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/018,303

(22) PCT Filed: Dec. 11, 2021

(86) PCT No.: PCT/US2021/062985
§ 371 (c)(1),
(2) Date: Jan. 27, 2023

(87) PCT Pub. No.: WO2022/082122
PCT Pub. Date: Apr. 21, 2022

(65) Prior Publication Data
US 2023/0313251 A1 Oct. 5, 2023

Related U.S. Application Data

(60) Provisional application No. 63/090,454, filed on Oct. 12, 2020, provisional application No. 63/090,743, filed on Oct. 13, 2020, provisional application No. 63/104,545, filed on Oct. 23, 2020.

(51) Int. Cl.
| | | |
|---|---|---|
| C12P 19/14 | (2006.01) | |
| C08H 8/00 | (2010.01) | |
| C12N 9/24 | (2006.01) | |
| C12N 9/42 | (2006.01) | |
| C12P 19/02 | (2006.01) | |

(52) U.S. Cl.
CPC ............... *C12P 19/02* (2013.01); *C08H 8/00* (2013.01); *C12N 9/2437* (2013.01); *C12P 19/14* (2013.01); *C12P 2201/00* (2013.01); *C12P 2203/00* (2013.01)

(58) Field of Classification Search
CPC ......... C08H 8/00; C12N 9/2437; C12P 19/14; C12P 2201/00
See application file for complete search history.

(56) References Cited

U.S. PATENT DOCUMENTS 6,419,788 B1   7/2002   Wingerson

FOREIGN PATENT DOCUMENTS

| CA | 2804934 A1 | 12/2011 |
| WO | 2011/044282 A1 | 4/2011 |
| WO | 2013/013318 A1 | 1/2013 |

OTHER PUBLICATIONS

International Search Report and Written Opinion, PCT/US2021/062985, dated Apr. 7, 2022.
International Preliminary Report on Patentability, PCT/US2021/062985, dated Apr. 13, 2023.

*Primary Examiner* — Maryam Monshipouri
(74) *Attorney, Agent, or Firm* — O'Connor & Company; Ryan P. O'Connor

(57) ABSTRACT

In some variations, a process for converting a biomass feedstock into a pretreated biomass material comprises: providing a biomass feedstock containing cellulose, hemicellulose, and lignin; introducing the biomass feedstock and a recycled vapor stream to a biomass-heating unit, thereby generating a heated biomass stream at a first temperature, wherein the recycled vapor stream is at a first pressure of at least atmospheric pressure; feeding the heated biomass stream to a biomass digestor operated at a second temperature and a second pressure to pretreat the biomass feedstock, thereby generating a digested stream comprising a solid-liquid mixture and a digestor vapor, wherein the second temperature is higher than the first temperature, and wherein the second pressure is higher than the first pressure; recycling at least a portion of the digestor vapor to the biomass-heating unit; and recovering or further processing the solid-liquid mixture as a pretreated biomass material. Many variations are disclosed.

14 Claims, 16 Drawing Sheets

PROCESSES FOR REDUCING STEAM CONSUMPTION AND IMPROVING PROCESS CARBON BALANCE IN BIOMASS CONVERSION TO SUGARS, BIOCHEMICALS, BIOFUELS, AND/OR BIOMATERIALS

PRIORITY DATA

This international patent application claims priority to U.S. Provisional Patent App. No. 63/090,454, filed on Oct. 12, 2020, to U.S. Provisional Patent App. No. 63/090,743, filed on Oct. 13, 2020, and to U.S. Provisional Patent App. No. 63/104,545, filed on Oct. 23, 2020, each of which is hereby incorporated by reference herein.

FIELD

The present invention generally relates to processes for converting lignocellulosic biomass into sugars, biochemicals, biofuels, and biomaterials.

BACKGROUND

Lignocellulosic biomass is the most abundant renewable material on the planet and has long been recognized as a potential feedstock for producing chemicals, fuels, and materials. Lignocellulosic biomass normally comprises primarily cellulose, hemicellulose, and lignin. Cellulose and hemicellulose are natural polymers of sugars, and lignin is an aromatic/aliphatic hydrocarbon polymer reinforcing the entire biomass network.

Biomass refining (or biorefining) has become prevalent in the world's economy. Cellulose fibers and sugars, hemicellulose sugars, lignin, alcohols, acids, olefins, syngas, and derivatives of these intermediates are being utilized for chemical and fuel production. Integrated biorefineries are capable of processing incoming biomass much the same as petroleum refineries now process crude oil. Underutilized lignocellulosic biomass feedstocks have the potential to be much cheaper than petroleum, on a carbon basis, as well as much better from an environmental life-cycle standpoint, including the potential for net-zero equivalent carbon dioxide emissions from a biorefinery. Over the past few years, several commercial-scale biorefineries have been constructed to convert lignocellulosic biomass such as corn stover, wheat straw, and sugarcane bagasse or straw into second-generation ethanol.

Broadly speaking, in a biorefinery, a biomass feedstock may be combusted to energy, pyrolyzed to biochar, gasified to syngas, hydrolyzed to sugars, mechanically refined to nanocellulose or other specialty celluloses, or a combination thereof. In essentially all these processes with the possible exception of combustion, an initial pretreatment of the biomass is necessary or desirable to improve the yield of desired products. Pretreatment is especially important when forming sugars and/or nanocellulose from biomass.

"Pretreatment" refers to one or more chemical or physical processes that convert lignocellulosic biomass from its native form, which is recalcitrant to hydrolysis, into a form for which enzymatic hydrolysis is more effective. Because biomass is inherently difficult to efficiently convert via cellulose and/or hemicellulose hydrolysis, essentially any biomass-conversion process utilizing hydrolysis will benefit from an initial pretreatment of the biomass using a pretreatment chemical such as water, an acid catalyst, and/or a solvent for lignin, for example.

If the pretreatment chemical that is to be distributed in the biomass is not evenly distributed throughout the biomass, the subsequent process steps that depend on the presence of the chemical do not take place efficiently. The portions of the biomass that did not receive an adequate amount of the chemical will be unreacted or underreacted. Simultaneously, other portions of the biomass may be exposed to too much of the chemical. Therefore, under the same process conditions (pressure, temperature, residence time, pH, etc.), some portions of the biomass will be underreacted, and other portions of the biomass will be overreacted. This problem results in lower process yields, increased production of undesirable side products, and an inefficient use of the pretreatment chemical to be applied, among other problems. A common solution is to utilize large quantities of pretreatment chemical, but this approach is costly as well as energy-intensive since the pretreatment chemical is typically contained in aqueous solution which must ultimately be removed downstream, requiring even more energy.

Pretreatment is often the largest energy-consuming part of a biomass-conversion process. The primary reason is that the temperature of the biomass feedstock must be raised to a high reaction temperature, such as 175° C., before the desired pretreatment chemistry will take place at an acceptable rate. Heating the biomass to the desired reaction temperature requires a significant amount of energy, usually in the form of high-quality steam.

Pretreatment of biomass is further complicated by the generation of many side products that cause downstream problems in reactions (including rate, selectivity, and yield to a desired product), separations of side products from the desired products, fouling caused by side products, and regulated emissions of side products. Common side products are inhibitors, such as furfural, that inhibit sugar fermentation or catalytic conversion to desired products, such as ethanol or jet fuel. To deal with the side products, more process energy is required, and the ratio of total process energy to desired product yield increases even further. As is known in chemical engineering, mass efficiency and energy efficiency are intricately linked.

The pretreatment technical challenges described above are even more important when the commercial market is considered. While consumers have desired renewable products, there historically has been an unwillingness to pay a green premium for the products. However, in recent years, this situation is drastically changing. Many governments and companies are driving towards low-carbon and even "net zero" solutions that minimize or eliminate the net generation of greenhouse-gas emissions, such as $CO_2$. The market craves energy efficiency and is willing to pay for it. There are various regulatory and market mechanisms including renewable fuel standards, renewable identification numbers, renewable energy credits, sustainability certifications (such as for cellulosic ethanol or sustainable aviation fuel), traceability registries, and the like. These regulatory and market mechanisms dictate the product value and therefore market price.

Improvements in biomass pretreatment are earnestly needed for biorefineries that convert lignocellulosic biomass into sugars, biochemicals, biofuels, or biomaterials.

SUMMARY

The present invention addresses the aforementioned needs in the art.

In some variations, the present invention provides a process for converting a biomass feedstock into a pretreated biomass material, the process comprising:
- (a) providing a biomass feedstock containing cellulose, hemicellulose, and lignin;
- (b) introducing the biomass feedstock and a recycled vapor stream to a biomass-heating unit, thereby generating a heated biomass stream at a first temperature, wherein the recycled vapor stream is at a first pressure of at least atmospheric pressure;
- (c) feeding the heated biomass stream to a biomass digestor operated at a second temperature and a second pressure to pretreat the biomass feedstock, thereby generating a digested stream comprising a solid-liquid mixture and a digestor vapor, wherein the second temperature is higher than the first temperature, and wherein the second pressure is higher than the first pressure;
- (d) optionally recycling at least a portion of the digestor vapor to step (b), as some or all of the recycled vapor stream; and
- (e) recovering or further processing the solid-liquid mixture as a pretreated biomass material.

In some embodiments, the biomass feedstock is a herbaceous feedstock, a woody feedstock, or a mixture of a herbaceous feedstock and a woody feedstock.

In some embodiments, the first pressure is greater than atmospheric pressure. The first pressure may be selected from about 0 barg to about 5 barg. The first temperature may be selected from about 50° C. to about 150° C., for example.

In some embodiments, the second pressure is selected from about 1 barg to about 25 barg. The second temperature may be selected from about 100° C. to about 220° C., for example.

In some embodiments, the recycled vapor stream is clean steam. The clean steam may be, or may be derived from, a process vapor stream, a utility vapor stream, a vapor stream obtained from an adjacent facility or process, or a combination thereof, for example.

In some embodiments, the recycled vapor stream is contaminated steam. The contaminated steam may be, or may be derived from, a process vapor stream, a utility vapor stream, a vapor stream obtained from an adjacent facility or process, or a combination thereof, for example.

The recycled vapor stream may contain a pretreatment chemical, such as (but not limited to) acetic acid, formic acid, or a combination thereof.

In some embodiments, step (d) is conducted to directly recycle the digestor vapor to step (b). Alternatively, or additionally, heat contained in the digestor vapor may be utilized to generate fresh vapor that is introduced to step (b) as part or all of the recycled vapor stream.

In some embodiments, the digested stream is fed to a mechanical refiner. In certain embodiments, the digestor vapor is separated from the solid-liquid mixture, and then the solid-liquid mixture is fed to a mechanical refiner.

In some embodiments, the solid-liquid mixture is divided into a solid-rich stream and a liquid-rich stream. The solid-rich stream may be fed to a mechanical refiner.

In some embodiments, the solid-liquid mixture is processed to hydrolyze the cellulose and/or the hemicellulose to monomeric and/or oligomeric sugars. Monomeric and/or oligomeric sugars include, but are not limited to, glucose, xylose, arabinose, mannose, galactose, fructose, sucrose, and oligomers thereof. Optionally, the sugars are processed via sugar separation into a monomer-enriched stream, which may be beneficial for fermentation.

In certain embodiments, the monomeric and/or oligomeric sugars are recovered as a sugar product.

In some embodiments, the monomeric and/or oligomeric sugars are fermented to a fermentation product, such as (but not limited to) ethanol, n-butanol, isobutanol, butanediols, succinic acid, lactic acid, or a combination thereof.

In some embodiments, the monomeric and/or oligomeric sugars are catalytically converted to a biofuel or a biochemical, such as (but not limited to) ethanol, ethylene, propylene, butenes, butadienes, bionaphtha, gasoline, jet fuel, diesel fuel, or a combination thereof.

The pretreated biomass material (the solid-liquid mixture) may alternatively, or additionally, be processed to convert the cellulose into nanocellulose as a biomaterial. The nanocellulose may include cellulose nanofibrils, cellulose nanocrystals, or a combination thereof.

The pretreated biomass material may be alternatively, or additionally, processed in many other ways to produce one or more sugars, biofuels, biochemicals, or biomaterials. For example, the pretreated biomass material may be subjected to pyrolysis, hydropyrolysis, hydrotreating, gasification, steam reforming, combustion, anaerobic digestion, or a combination thereof, or any other biorefinery downstream process that benefits from steps (a)-(d).

BRIEF DESCRIPTION OF THE FIGURES

FIG. 1 is an exemplary block-flow diagram depicting a process of converting biomass into fermentation products, in some embodiments employing a mechanical conveyor with liquid recycle upstream of a biomass digestor.

FIG. 2 is an exemplary block-flow diagram depicting a process of converting biomass into fermentation products, in some embodiments employing a mechanical conveyor with liquid recycle upstream of a biomass refiner.

FIG. 3 is an exemplary block-flow diagram depicting a process of converting biomass into products using catalyzed reactions of sugars, in some embodiments employing a mechanical conveyor with liquid recycle upstream of a biomass digestor.

FIG. 4 is an exemplary block-flow diagram depicting a process of converting biomass into nanocellulose, in some embodiments employing a mechanical conveyor with liquid recycle upstream of a biomass digestor.

FIG. 5 is an exemplary block-flow diagram depicting a process of converting biomass into pretreated material, in some embodiments employing vapor recycle to a biomass-heating unit.

FIG. 6 is an exemplary block-flow diagram depicting a process of converting biomass into pretreated material, in some embodiments utilizing clean, recycled steam in a biomass-heating unit.

FIG. 7 is an exemplary block-flow diagram depicting a process of converting biomass into pretreated material, in some embodiments utilizing contaminated, recycled steam in a biomass-heating unit.

FIG. 8 is an exemplary block-flow diagram depicting a process of converting biomass into pretreated material, in some embodiments employing a heat-recovery vapor generator to recover the heat of the digestor vapor and generate fresh vapor to feed into the biomass-heating unit.

FIG. 9 is an exemplary block-flow diagram depicting a process of converting biomass into products, in some embodiments employing a digestor, a vapor-separation unit, a refiner, and a hydrolysis reactor to generate sugars for conversion to products.

FIG. 10 is an exemplary block-flow diagram depicting a process of converting biomass into products, in some embodiments employing a digestor, a vapor-separation unit, recycle of vapor to the reaction solution fed to the digestor, a refiner, and a hydrolysis reactor to generate sugars for conversion to products.

FIG. 11 is an exemplary block-flow diagram depicting a process of converting biomass into products, in some embodiments employing a digestor, a refiner, a vapor-separation unit after the refiner, and a hydrolysis reactor to generate sugars for conversion to products.

FIG. 12 is an exemplary block-flow diagram depicting a process of converting biomass into products, in some embodiments employing a digestor, a multi-stage vapor-separation unit, an optional refiner disposed between vapor-separation unit stages, and a multi-stage hydrolysis reactor to generate sugars for biological or catalytic conversion to products.

FIG. 13 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a vapor-separation unit, vapor recycle to the biomass-heating unit, a refiner, a hydrolysis reactor, a fermentor, and a purification unit to generate products.

FIG. 14 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a refiner, a vapor-separation unit, vapor recycle to the biomass-heating unit, a hydrolysis reactor, a catalytic reactor, and a purification unit to generate products.

FIG. 15 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a vapor-separation unit, vapor recycle to the biomass-heating unit, a refiner, and a hydrolysis reactor to generate a sugar product.

FIG. 16 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a vapor-separation unit, vapor recycle to the biomass-heating unit, and a refiner to generate nanocellulose.

DETAILED DESCRIPTION OF EMBODIMENTS

Figure 1:
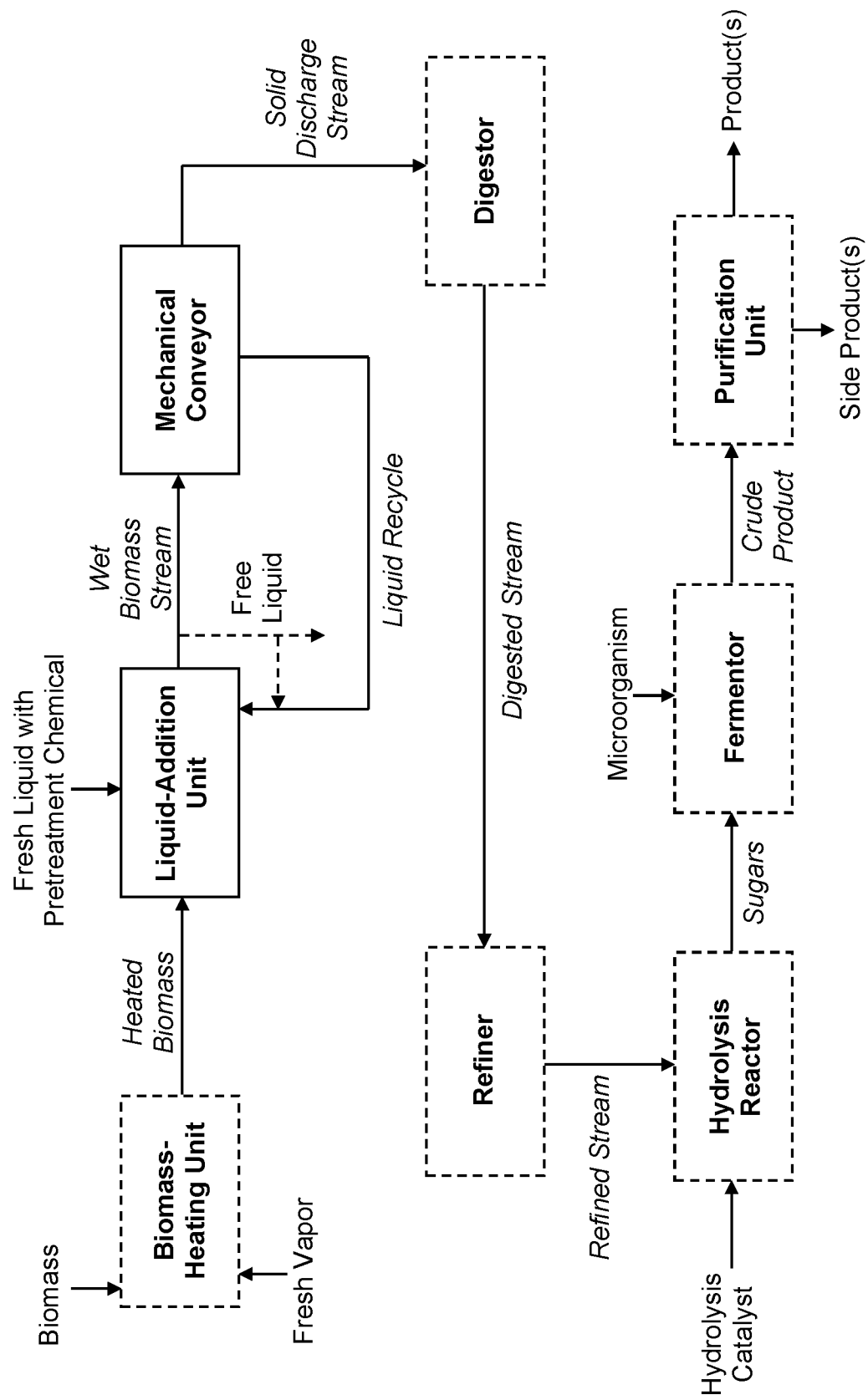
FIGS. 1 to 16 are simplified block-flow diagrams depicting the process and system of various embodiments. In these drawings, dotted lines denote optional streams and units.

This description will enable one skilled in the art to make and use the invention, and it describes several embodiments, adaptations, variations, alternatives, and uses of the invention. These and other embodiments, features, and advantages of the present invention will become more apparent to those skilled in the art when taken with reference to the following detailed description of the invention in conjunction with any accompanying drawings.

As used in this specification and the appended claims, the singular forms "a," "an," and "the" include plural referents unless the context clearly indicates otherwise. Unless defined otherwise, all technical and scientific terms used herein have the same meaning as is commonly understood by one of ordinary skill in the art to which this invention belongs. All composition numbers and ranges based on percentages are weight percentages, unless indicated otherwise. All ranges of numbers or conditions are meant to encompass any specific value contained within the range, rounded to any suitable decimal point.

Unless otherwise indicated, all numbers expressing reaction conditions, stoichiometries, concentrations of components, and so forth used in the specification and claims are to be understood as being modified in all instances by the term "about." As used herein, the term "about" means±20% of the indicated range or value, unless otherwise indicated. Also, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phrase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phrase "consisting essentially of" limits the scope of a claim to the specified elements or method steps, plus those that do not materially affect the basis and novel characteristic(s) of the claimed subject matter.

With respect to the terms "comprising," "consisting of," and "consisting essentially of," where one of these three terms is used herein, the presently disclosed and claimed subject matter may include the use of either of the other two terms, except when used in a Markush group. Thus in some embodiments not otherwise explicitly recited, any instance of "comprising" may be replaced by "consisting of" or, alternatively, by "consisting essentially of."

As used herein, any concentration range, percentage range, ratio range, or integer range is to be understood to include the value of any integer within the recited range and, when appropriate, fractions thereof (such as one tenth of an integer), unless otherwise indicated. Also, any number range recited herein is to be understood to include any integer within the recited range, unless otherwise indicated.

For purposes of an enabling technical disclosure, various explanations, hypotheses, theories, speculations, assumptions, and so on are disclosed. The present disclosure does not rely on any of these being in fact true. None of the explanations, hypotheses, theories, speculations, or assumptions in this detailed description shall be construed to limit the scope of the disclosure in any way.

This disclosure provides a large number of processes, process steps, process conditions, systems, units, embodiments, and options that are generally useful in biorefineries for converting biomass to sugars, biochemicals, biomaterials, and/or biofuels. It will be recognized by a skilled artisan that the inventive concepts are widely applicable to various biomass-conversion processes, including those employing pretreatment, hydrolysis, pyrolysis, gasification, digestion, fermentation, catalysis, and so on. Many examples of processes will be described herein, with the understanding that there are other embodiments in which fewer than, or more than, the disclosed process steps may be employed for that particular process.

As will be understood by a skilled artisan, in the description of a process herein, the order of process steps may be varied without departing from the scope of the invention defined by the claims. Thus for example when a process is described to include steps A, B, C, and D, it will be understood that, unless otherwise stated, the process may be conducted sequentially (A-B-C-D), or in any other logical sequence (e.g., A-C-B-D, A-B-D-C, B-C-A-D, etc.), which alternative process sequences may not provide all the benefits of the preferred sequence but which nevertheless provide a benefit compared to the prior art. In some embodiments, when steps of a process are disclosed, the process is conducted in sequence, i.e. the first step (often denoted by "(a)") is conducted before the second step (often denoted by "(b)"), the second step is conducted before the third step (often denoted by "(c)"), and so on. In other embodiments, when steps of a process are disclosed, the process is not conducted in the sequence stated but rather in another sequence.

Headings provided herein are for convenience only and do not interpret the scope or meaning of the claimed embodiments.

Processes for Reducing Chemical Use and Equipment Corrosion

Some variations are predicated on the improved utilization of pretreatment chemicals applied to lignocellulosic biomass, such as herbaceous biomass (e.g., sugarcane bagasse or straw, energy cane bagasse or straw, corn stover, wheat straw, etc.).

Some embodiments utilize the application of liquid containing a pretreatment chemical to be applied, at a point prior to a plug-screw feeder (or other mechanical conveyor), rather than after the plug-screw feeder. The pretreatment chemical may be a catalyst that catalyzes a reaction (e.g., hydrolysis), or a reactant that is consumed in a chemical reaction (e.g., water consumed in hydrolysis, hydrogen consumed in deoxygenation, etc.).

The pretreatment chemical, contained in the liquid phase, is typically well in excess of the amount of pretreatment chemical needed for the desired reactions to take place. Furthermore, because the pretreatment chemical is in the liquid phase, and not necessarily in contact with the cellulose-hemicellulose-lignin fiber of the biomass, the chemical may not actually be participating in the reaction.

After the liquor containing the pretreatment chemical to be impregnated has been applied to the biomass, the excess free liquid may be drained off, however, because herbaceous biomass can absorb and hold several times as much liquid as its dry fiber weight (up to 4.5 parts liquid per one part dry biomass fiber, by weight), the biomass still contains a significant amount of liquid and chemical in the fiber. This excess liquid and pretreatment chemical may then be removed from the biomass using a mechanical conveyor (e.g., a plug-screw feeder) configured to physically remove liquid, resulting in a biomass liquid content that has been significantly reduced. The excess pretreatment chemical and liquid may be returned to the process to be applied to incoming biomass. The biomass exiting the plug-screw feeder preferably contains only the liquid and pretreatment chemical required for the subsequent process reactions.

Several advantages arise from these variations. First, the pretreatment chemical that remains free in the liquid phase preferably does not pass forward in the process. In preferred embodiments, only that pretreatment chemical that is in direct contact with the biomass fiber (e.g., absorbed into the bulk fiber phase and/or adsorbed onto fiber surfaces) is passed forward in the process. This method reduces the amount of pretreatment chemical that passes through subsequent steps of the process without chemically participating in desirable chemistry. The excess pretreatment chemical is recycled, where it is applied to fresh biomass which has not yet had any pretreatment chemical applied, or applied to pre-steamed biomass which may have had some exposure to the pretreatment chemical (e.g., acetic acid) but less than the full amount to be impregnated into the biomass. The net effect is the reduction of pretreatment chemical used. A consequential benefit is the reduction of other chemicals used in subsequent steps that would be required to neutralize or counteract the excess pretreatment chemical (e.g., a base to neutralize excess acid) and reduction in operating cost associated with removal of neutralized pretreatment chemical (e.g., a salt).

Another benefit to these embodiments is reduced corrosion potential when the pretreatment chemical is corrosive, as is often the case when an acidic or alkaline chemical is employed. There may be a reduction in the corrosion-resistance requirement for piping and equipment designed to handle and process the lignocellulosic biomass when corrosive chemicals are used. Preferably, the free liquid has been removed from the surface and pore structure of the biomass, which means there is not as much free liquid and pretreatment chemical available to contact the surface of the equipment. Therefore, the corrosion resistance of the material of construction can be much less than it would need to be if the free liquid and pretreatment chemical were able to contact the surface of the equipment. There is a reduction in equipment cost in subsequent processing steps. As an example, a sugarcane bagasse processing reactor lined with 316L stainless steel may be used rather than 2205 stainless steel, which is a higher-cost austenitic-ferritic stainless steel with chromium, nitrogen, and molybdenum to inhibit local and uniform corrosion.

In some variations, the present invention provides a process for preparing a biomass feedstock for conversion to a sugar, a biofuel, a biochemical, or a biomaterial, the process comprising:

(a) providing a biomass feedstock containing cellulose, hemicellulose, and lignin;

(b) optionally, introducing the biomass feedstock and a first vapor stream to a biomass-heating unit, thereby generating a heated biomass stream;

(c) introducing the biomass feedstock, or the heated biomass stream if step (b) is conducted, and a first liquid stream to a liquid-addition unit, thereby generating a wet biomass stream, wherein the first liquid stream contains a pretreatment chemical;

(d) introducing the wet biomass stream to a mechanical conveyor operated to physically remove liquid from the wet biomass stream, thereby generating an excess-liquid stream comprising the pretreatment chemical and a solid discharge stream comprising the biomass feedstock and the pretreatment chemical;

(e) recycling at least a portion of the excess-liquid stream to the first liquid stream; and (f) recovering or further processing the solid discharge stream.

In some embodiments, the biomass feedstock is a herbaceous feedstock. In other embodiments, the biomass feedstock is a woody feedstock, or a mixture of a herbaceous feedstock and a woody feedstock.

The first liquid stream contains at least some liquid. The first liquid stream may contain only a liquid phase, or both a liquid phase and a vapor phase, or both a liquid phase and a solid phase, or all of a liquid phase, a vapor phase, and a solid phase.

The pretreatment chemical may be selected from the group consisting of an acid, a base, a salt, an organic solvent, an inorganic solvent, an ionic liquid, an enzyme, water, and combinations thereof, for example. The pretreatment chemical may be a catalyst or a reactant. In certain embodiments, water is the only pretreatment chemical.

In some embodiments, the mechanical conveyor is a screw conveyor, such as (but by no means limited to) a plug-screw feeder.

In some embodiments, step (b) is conducted. In these embodiments, the first vapor stream may contain a pretreatment chemical (e.g., an acid catalyst) which may be the same pretreatment chemical introduced in step (c), or a different pretreatment chemical.

When step (b) is conducted, there may be a pre-steaming discharge vapor lock upstream of the liquid-addition unit. The pre-steaming discharge vapor lock may be a rotary valve or a screw vapor lock, for example. The pre-steaming discharge vapor lock is especially beneficial when a vapor-phase pretreatment chemical, such as sulfur dioxide, is used downstream.

In some embodiments, excess free liquid is drained from the wet biomass stream between step (c) and step (d). After optionally draining excess free liquid, the wet biomass stream may contain from about 25 wt % to about 95 wt % liquid, such as about, at least about, or at most about 25, 30, 35, 40, 45, 50, 55, 60, 65, 70, 75, 80, 85, 90, or 95 wt % liquid, for example.

In certain embodiments, an inclined helical screw with mixing elements may be utilized to apply and then drain away excess impregnation solution. In this configuration, the inclined helical screw functions as the liquid-addition unit as well as a means of removing excess free liquid prior to the mechanical conveyor.

Following the extensive liquid removal in the mechanical conveyor, the solid discharge stream may contain from about 10 wt % to about 70 wt % liquid, such as from about 30 wt % to about 40 wt % liquid. In various embodiments, the solid discharge stream contains about, at least about, or at most about 10, 15, 20, 25, 30, 35, 40, 45, 50, 55, 60, 65, or 70 wt % liquid, for example.

The mechanical conveyor (e.g., a screw conveyor) may be configured to remove at least 10%, preferably at least 25%, more preferably at least 50%, and possibly at least 60%, at least 70%, at least 80%, or at least 90% (weight basis) of the liquid present in the wet biomass stream. When free liquid is not removed from the wet biomass stream, a greater overall quantity of liquid will typically be removed in the mechanical conveyor. However, it is preferable to remove most or all of the excess free liquid prior to feeding the wet biomass stream into the mechanical conveyor.

Typically, the recycled liquid contains a pretreatment chemical, such as an acid pretreatment catalyst (e.g., nitric acid, sulfuric acid, or sulfurous acid). However, in certain embodiments, the recycled liquid consists essentially of water and any materials extracted out of the biomass in the mechanical conveyor. In these embodiments, the mechanical conveyor may be used to control the moisture content for purposes of optimal digestor operation, for example.

In some embodiments, step (f) comprises feeding the solid discharge stream to a mechanical refiner. Alternatively, or additionally, step (f) may comprise feeding the solid discharge stream to a biomass digestor operated to pretreat the biomass feedstock, thereby generating a digested stream. The digested stream from the digestor may be fed to the next unit operation through a blowback valve, which provides protection against vapor blowback.

The digested stream from the digestor may be fed to a mechanical refiner without separating the second vapor stream from the solid-liquid stream. Alternatively, the digested stream may be divided into a solid-liquid stream and a second vapor stream. This solid-liquid stream may be fed to a mechanical refiner.

Alternatively, or additionally, the solid-liquid stream may be divided into a solid-rich stream and a liquid-rich stream. The solid-rich stream may be fed to a mechanical refiner. In some embodiments, the solid-rich stream is rich in cellulose, and the liquid-rich stream is rich in hemicellulose. It can be advantageous to separately process the cellulose and the hemicellulose, as explained later.

The solid discharge stream may be processed to hydrolyze the cellulose and/or the hemicellulose to monomeric and/or oligomeric sugars. Monomeric and/or oligomeric sugars include, but are not limited to, glucose, xylose, arabinose, mannose, galactose, fructose, sucrose, and oligomers thereof.

Different biomass feedstocks have different sugar profiles in the cellulose and hemicellulose fractions. For example, in hardwoods and herbaceous feedstocks, the main hemicellulose sugar is the $C_5$ sugar xylose, while in softwoods, both $C_5$ and $C_6$ sugars are prevalent in hemicellulose.

Optionally, the sugars are processed via sugar separation into a monomer-enriched stream, which may be beneficial for fermentation. Sugar separation may be accomplished using membrane separation, for example.

In some embodiments, the monomeric and/or oligomeric sugars are fermented to a fermentation product, such as (but not limited to) ethanol, n-butanol, isobutanol, butanediols, succinic acid, lactic acid, or a combination thereof.

In some embodiments, the monomeric and/or oligomeric sugars are catalytically converted to a biofuel or a biochemical, such as (but not limited to) ethanol, ethylene, propylene, butenes, butadienes, bionaphtha, gasoline, jet fuel, diesel fuel, or a combination thereof.

In some embodiments, the monomeric and/or oligomeric sugars are recovered as a sugar product, or multiple sugar products.

The solid discharge stream from step (f) may alternatively, or additionally, be processed to convert the cellulose into nanocellulose as a biomaterial. The nanocellulose may include cellulose nanofibrils, cellulose nanocrystals, or a combination thereof.

The solid discharge stream from step (f) may be alternatively, or additionally, processed in many other ways to produce one or more sugars, biofuels, biochemicals, or biomaterials. For example, the solid discharge stream may be subjected to pyrolysis, hydropyrolysis, hydrotreating, gasification, steam reforming, combustion, anaerobic digestion, or a combination thereof, or any other biorefinery downstream process that benefits from steps (a)-(e).

As used herein, "pyrolysis" is the thermal decomposition of a carbonaceous material. In pyrolysis, less oxygen is present than is required for complete combustion of the material, such as at most about 10%, 1%, 0.1%, or 0.01% of the oxygen (O2 molar basis) that is required for complete combustion. In some embodiments, pyrolysis is performed in the absence of oxygen.

As used herein, "hydropyrolysis" is the thermal decomposition of a carbonaceous material in the presence of hydrogen. In hydropyrolysis, less oxygen is present than is required for complete combustion of the material, such as at most about 10%, 1%, 0.1%, or 0.01% of the oxygen (02 molar basis) that is required for complete combustion. In some embodiments, hydropyrolysis is performed in the absence of oxygen.

"Hydrotreating" refers to exposure to hydrogen for purposes of adding hydrogen to a molecule (e.g., hydration of an olefin using $H_2$), removing a component from a molecule (e.g., sulfur removal via $S+H_2 \rightarrow H_2S$), or a combination thereof.

In the case of hydropyrolysis and hydrotreating, the $H_2$ is preferably renewable hydrogen. As used herein, "renewable hydrogen" is determined by correlating the $^2H/PH$ isotopic ratio with the renewability of the starting feedstock. The $^2H/PH$ isotopic ratio correlates with renewability of the hydrogen, with higher $^2H/PH$ isotopic ratios indicating a greater renewable hydrogen content.

As used herein, "gasification" refers to the conversion of biomass at high temperatures (typically >700° C.), without combustion, by controlling the amount of oxygen and/or steam present in the reaction. When the gasification employs only steam and no oxygen, the reactions may be referred to as steam reforming.

As used herein, "anaerobic digestion" refers to the conversion of the organic material in biomass by bacteria, in the absence of oxygen, to create methane-rich biogas.

FIG. 1 is an exemplary block-flow diagram depicting a process of converting biomass into fermentation products, in some embodiments employing a mechanical conveyor with liquid recycle upstream of a biomass digestor. In FIG. 1, biomass is optionally heated in a biomass-unit unit, which may be a pre-steaming unit. Fresh vapor (e.g., fresh steam) may be directly injected into the biomass-unit unit. There may be a vapor purge from the biomass-heating unit. The biomass is fed to a liquid-addition unit, which may be a pre-impregnation unit. Fresh liquid with a pretreatment chemical is introduced to the liquid-addition unit. The wet biomass stream is fed to a mechanical conveyor. Excess free liquid may be removed from the wet biomass stream, prior to entrance into the mechanical conveyor. In the mechanical conveyor, liquid is physically removed, such as by pressing or by the mechanical forces from a rotating screw. The liquid removed from the mechanical conveyor is recycled to the liquid-additional unit, at least in part. Some or all of the excess free liquid may be combined with the recycled liquid, as depicted in FIG. 1. The solid discharge stream from the mechanical conveyor may be fed to a digestor, producing a digested stream that may be mechanically refined in a refiner. The refined stream may be fed to a hydrolysis reactor using a hydrolysis catalyst (e.g., enzymes or sulfuric acid), to generate sugars. The sugars may be fermented to generate a crude product using a microorganism (e.g., yeast or bacteria). The crude product may be purified into the desired product(s), rejecting any side product(s).

Figure 2:
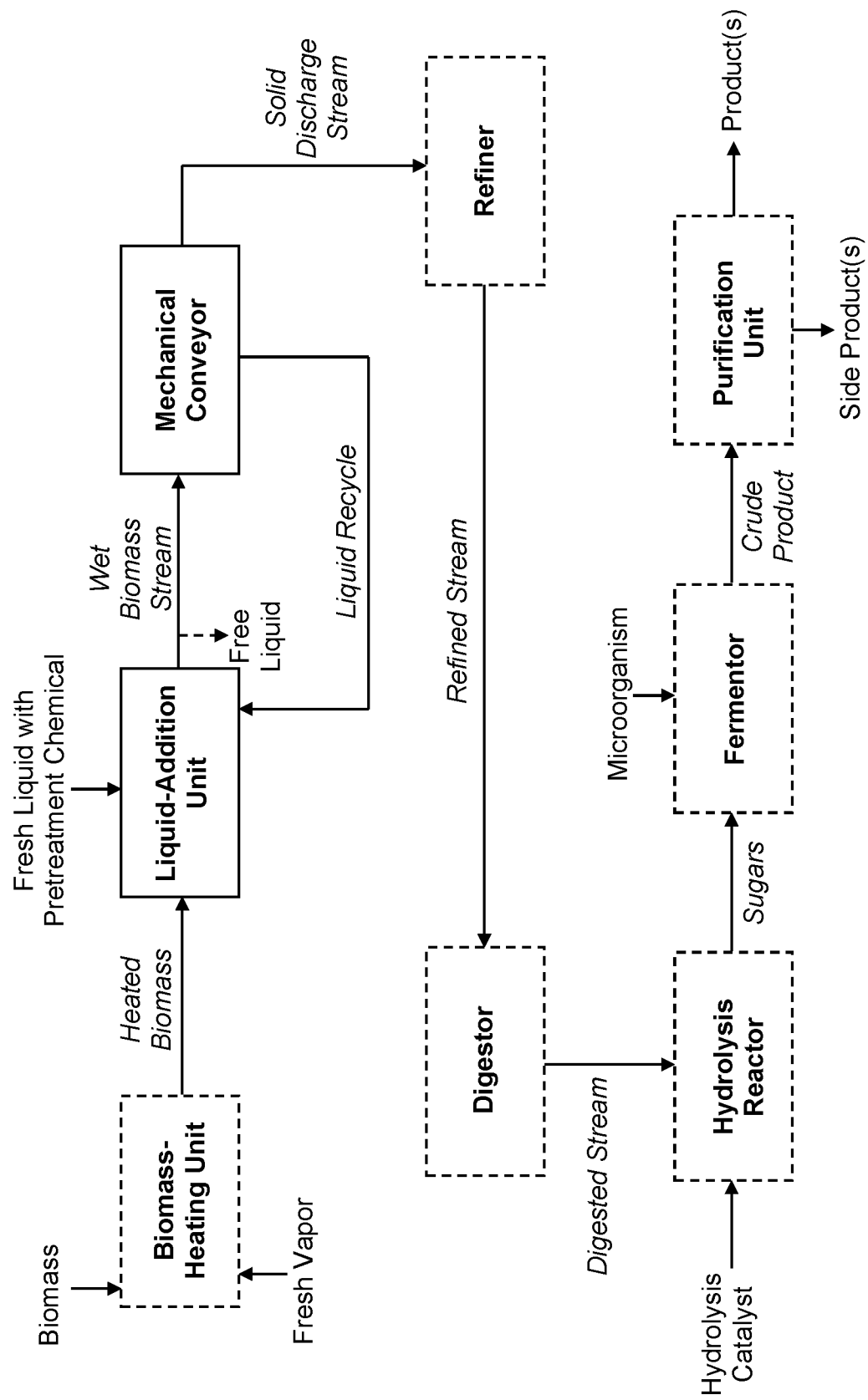

FIG. 2 is an exemplary block-flow diagram depicting a process of converting biomass into fermentation products, in some embodiments employing a mechanical conveyor with liquid recycle upstream of a biomass refiner. FIG. 2 is similar to FIG. 1, described above, except that the sequence of the digestor and the refiner is switched.

Figure 3:
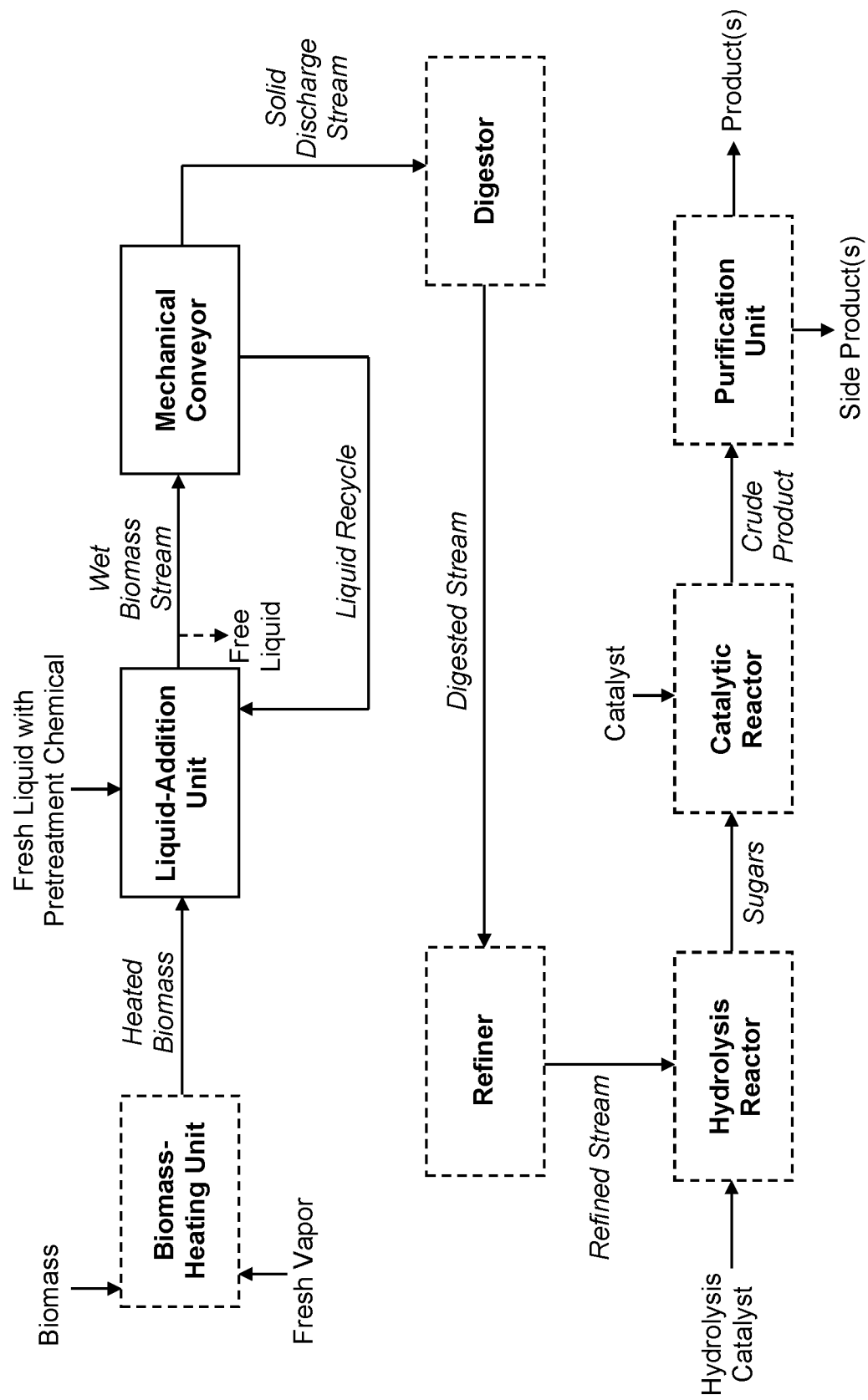

FIG. 3 is an exemplary block-flow diagram depicting a process of converting biomass into products using catalyzed reactions of sugars, in some embodiments employing a mechanical conveyor with liquid recycle upstream of a biomass digestor. FIG. 3 is similar to FIG. 1, described above, except that the sugars from hydrolysis are not fermented but rather are catalytically converted to a product, using a catalyst such as a heterogeneous catalyst (e.g., a metal-zeolite fixed bed) or a homogeneous catalyst (e.g., an metal-containing soluble acid).

Figure 4:
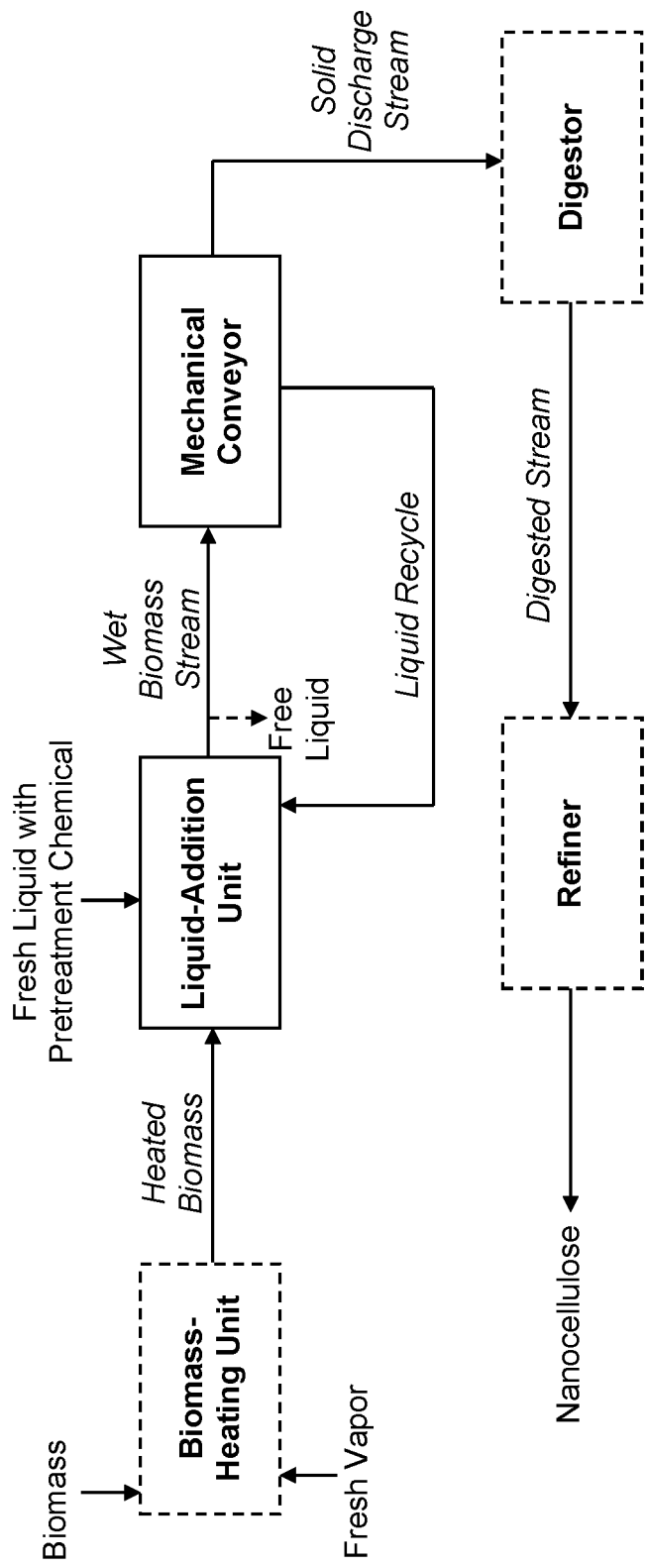

FIG. 4 is an exemplary block-flow diagram depicting a process of converting biomass into nanocellulose, in some embodiments employing a mechanical conveyor with liquid recycle upstream of a biomass digestor. FIG. 4 is similar to FIG. 1, described above, except that the digested stream is refined to produce nanocellulose, rather than hydrolyzed to produce sugars.

The process may be carried out as a batch, continuous, or semi-continuous process. Each unit within the process may be configured for co-current, countercurrent, or cross-current flow. Each unit within the process may be a static vessel or an agitated vessel, in horizontal, vertical, or slanted orientation.

Processes for Reducing Steam Consumption and Improving Carbon Balance

Other variations of the invention are premised on the optimization of steam (or other vapor) usage in biorefinery processes.

A significant benefit of heating the biomass in the pre-steaming unit (or another biomass-heating unit) is that pre-steaming the biomass provides for improved uptake (impregnation) of liquid and/or pretreatment chemicals in the liquid-addition unit. In various embodiments, pre-steaming improves the impregnation of a pretreatment chemical by about, or at least about, 5%, 10%, 15%, 20%, 25%, 30%, 35%, 40%, 45%, or 50%, or more, compared to a process that does not utilize pre-steaming or other vapor exposure in the biomass-heating unit. Improved impregnation means that the pretreatment chemical better penetrates the biomass and may result in a higher concentration of pretreatment chemical in the biomass for a given concentration in the impregnation liquid, or may result in a desired (target) concentration of pretreatment chemical in the biomass using a lower concentration in the impregnation liquid, for example.

According to the principles taught herein, there may be a reduction in the amount of steam required for the processing of lignocellulosic biomass (e.g., herbaceous or woody biomass) for the production of sugars (e.g., dextrose), biofuels (e.g., ethanol), biochemicals (e.g., 1,4-butanediol), and/or biomaterials (e.g. nanocellulose). By reducing the amount of fresh high-pressure steam required for the process, the process carbon balance is improved. The process carbon balance refers to the net $CO_2$ emissions per ton of biomass feedstock processed. Additionally, by condensing recycled process vapor in a useful fashion—and reintroducing it into the process—the process water balance is improved. The process water balance refers to the net water emissions per ton of biomass feedstock processed.

Some variations utilize direct heating of biomass with recovered vapor (water vapor and/or other vapor) from other unit operations of the process, utility systems, adjacent processes or facilities, or a combination thereof. Direct heating of the biomass with low-pressure recovered vapor (e.g., low-pressure recycled steam) improves the thermal efficiency of the process.

Direct heating of the biomass with low-pressure recovered vapor may also be utilized to recover water and potentially other chemicals, such as acids (e.g., acetic acid or formic acid). In some cases, the recovered chemicals serve as pretreatment chemicals downstream, to aid in the lignocellulosic conversion process by, for example, catalyzing hydrolysis of cellulose or hemicellulose, or by reacting with cellulose or lignin. In other cases, the recovered chemicals do not necessarily function as pretreatment chemicals, but they must be removed from the vapor stream prior to release to the atmosphere. By directly heating the biomass with the low-pressure vapor, components that would have otherwise been emitted to the atmosphere may instead be recovered downstream, such as in liquid form, and used for other purposes.

In some embodiments, recovered vapor is passed through a biomass-heating unit containing biomass, preferably in a countercurrent fashion, prior to elevating the biomass to digestor pressure. The biomass enters the biomass-heating unit at a temperature less than the saturation temperature of the recovered vapor, typically at ambient temperature. In the biomass-heating unit, the biomass is heated to, or near, the saturation temperature of the recovered vapor. This method reduces the amount of high-pressure vapor (e.g., fresh boiler steam or recovered high-pressure process vapor) that must be used to heat the biomass to digestor temperature. The source of the vapor to be injected into the biomass may be recovered process vapor from any part of the overall biomass-conversion process, from utility processes, or from other processes operated at adjacent facilities. The vapor may be clean steam, contaminated steam, or any other process or utility vapor. To further improve the energy efficiency and carbon balance of the process, the vapor that exits the biomass-heating unit may be condensed by other process or utility streams that must be warmed.

Generally speaking, the temperature of the biomass feedstock must be raised to a reaction temperature before the desired reaction(s) will take place at an economical rate. The biomass enters the process at a temperature considerably lower than the reaction temperature-often at, or near, ambient temperature (about 25° C.). In various embodiments, the biomass enters the process at ambient temperatures from about −40° C. to about 40° C., such as from about −10° C. to about 30° C.

To bring the biomass up to the desired reaction temperature (e.g., 140-180° C.), high-pressure vapor such as fresh boiler steam is typically used to raise the temperature of the biomass through direct heating, after the biomass has been raised to reactor pressure. The biomass could also be heated through indirect heating, but this is usually not practical, due to the poor heat-transfer characteristics of the stream containing the biomass.

Heating the biomass to the desired reaction temperature requires a significant amount of energy. The step of heating the digestor feed materials to digestion temperature is usually one of the largest steam consumers in a lignocellulosic conversion process. The use fresh boiler steam, high-pressure recovered process vapor, or another high-quality vapor stream to raise the temperature of the biomass from near ambient all the way to reaction temperature is not thermodynamically efficient. Such a method is both energy-inefficient as well as carbon-inefficient, causing a poor carbon balance.

By first preheating the biomass from near ambient temperature to, or near, the saturation temperature of the lower-pressure recycled vapor stream, the amount of higher-pressure vapor needed to bring the biomass to reaction temperature is greatly reduced. The preheating takes place in a biomass-heating unit, while the remainder of the heating takes place in a digestor or in another unit (e.g., a pre-impregnation unit) that is physically distinct from the biomass-heating unit.

In some embodiments, the reduction of high-pressure steam is from about 1% to about 25%, such as from about 8% to about 16%, by using a recycled vapor stream in the biomass-heating unit. In various embodiments, the reduction of high-pressure steam is about, or at least about 1%, 2%, 3%, 4%, 5%, 6%, 7%, 8%, 9%, 10, 1%, $1^2$%, 13%, 14%, 15%, 16%, 17%, 18%, 19%, 20%, 21%, 22%, 23%, 24%, 25%, or more, including any intervening ranges.

This method reduces both the process operating costs and the amount of carbon dioxide that is emitted to the atmosphere as a result of steam or vapor generation. The result is an improved carbon balance of the process. Given that the market acceptance and market price of a sugar, biofuel, biochemical, or biomaterial is now often determined, at least in part, by the carbon balance of the process, the profitability of the process may also be improved.

In various embodiments, the carbon intensity of the process is reduced by about, or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more, including any intervening ranges.

In various embodiments, the process water balance of the process is improved by about, or at least about 1%, 2%, 3%, 4%, 5%, 6%, 7%, 8%, 9%, 10%, 11%, 12%, 13%, 14%, 15, $1^6$%, 1%, 18%, 19%, 20%, 21%, 22%, 23%, 24%, 25%, or more, including any intervening ranges.

The process may be carried out as a batch, continuous, or semi-continuous process. Each unit within the process may be configured for co-current, countercurrent, or cross-current flow. Each unit within the process may be a static vessel or an agitated vessel, in horizontal, vertical, or slanted orientation.

In some variations, the present invention provides a process for converting a biomass feedstock into a pretreated biomass material, the process comprising:
  (a) providing a biomass feedstock containing cellulose, hemicellulose, and lignin;
  (b) introducing the biomass feedstock and a recycled vapor stream to a biomass-heating unit, thereby generating a heated biomass stream at a first temperature, wherein the recycled vapor stream is at a first pressure of at least atmospheric pressure;
  (c) feeding the heated biomass stream to a biomass digestor operated at a second temperature and a second pressure to pretreat the biomass feedstock, thereby generating a digested stream comprising a solid-liquid mixture and a digestor vapor, wherein the second temperature is higher than the first temperature, and wherein the second pressure is higher than the first pressure;
  (d) optionally recycling at least a portion of the digestor vapor to step (b), as some or all of the recycled vapor stream; and
  (e) recovering or further processing the solid-liquid mixture as a pretreated biomass material.

In some embodiments, the biomass feedstock is a herbaceous feedstock, a woody feedstock, or a mixture of a herbaceous feedstock and a woody feedstock.

The first pressure of the recycled vapor stream may be at atmospheric pressure, but preferably the recycled vapor stream is at least slightly greater than atmospheric pressure.

In some embodiments, the first pressure is greater than atmospheric pressure (0 barg). For example, the first pressure may be selected from about 0 barg to about 5 barg. In various embodiments, the first pressure is about, at least about, or at most about 0.1 barg, 0.2 barg, 0.3 barg, 0.4 barg, 0.5 barg, 0.6 barg, 0.7 barg, 0.8 barg, 0.9 barg, 1 barg, 1.1 barg, 1.2 barg, 1.3 barg, 1.4 barg, 1.5 barg, 1.6 barg, 1.7 barg, 1.8 barg, 1.9 barg, 2.0 barg, 2.1 barg, 2.2 barg, 2.3 barg, 2.4 barg, 2.5 barg, 2.6 barg, 2.7 barg, 2.8 barg, 2.9 barg, 3.0 barg, 3.1 barg, 3.2 barg, 3.3 barg, 3.4 barg, 3.5 barg, 3.6 barg, 3.7 barg, 3.8 barg, 3.9 barg, 4.0 barg, 4.1 barg, 4.2 barg, 4.3 barg, 4.4 barg, 4.5 barg, 4.6 barg, 4.7 barg, 4.8 barg, 4.9 barg, or 5.0 barg, including any intervening ranges.

The first pressure may be greater than atmospheric pressure by at least 0.01 bar, 0.02 bar, 0.03 bar, 0.04 bar, 0.05 bar, 0.1 bar, 0.15 bar, 0.2 bar, 0.25 bar, 0.3 bar, 0.4 bar, 0.5 bar, 0.6 bar, 0.7 bar, 0.8 bar, 0.9 bar, 1.0 bar, 1.1 bar, 1.2 bar, 1.3 bar, 1.4 bar, 1.5 bar, 2.0 bar, 2.5 bar, 3.0 bar, 3.5 bar, 4.0 bar, 4.5 bar, or 5.0 bar, including any intervening ranges, for example. Note that bar=bara, units of absolute pressure.

Atmospheric pressure is usually 1 bar, but it depends on altitude. For example, the atmospheric pressure in Denver, Colorado is about 0.8 bar (which equates to −0.2 barg). The atmospheric pressure in an underground geological formation may be about 1.1 bar to about 2 bar, for example. In various embodiments, atmospheric pressure is about 0.75 bar, 0.80 bar, 0.85 bar, 0.90 bar, 0.95 bar, 0.98 bar, 0.99 bar, 1.0 bar, 1.01 bar, 1.02 bar, 1.05 bar, 1.10 bar, or 1.15 bar. Unless otherwise stated, atmospheric pressure is 1.00 bar (0.00 barg).

The first temperature of the recycled vapor stream may be selected from about 50° C. to about 150° C., for example. In various embodiments, the first temperature is selected to be about, at least about, or at most about 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., or 150° C., including any intervening ranges (e.g., about 100-125° C.).

In some embodiments, the second pressure of the biomass digestor is selected from about 1 barg to about 25 barg. In various embodiments, the second pressure is about, at least about, or at most about 1 barg, 1.5 barg, 2 barg, 2.5 barg, 3 barg, 4 barg, 5 barg, 6 barg, 7 barg, 8 barg, 9 barg, 10 barg, 11 barg, 12 barg, 13 barg, 14 barg, 15 barg, 20 barg, or 25 barg, including any intervening ranges.

The second temperature of the biomass digestor may be selected from about 100° C. to about 220° C., for example. In various embodiments, the second temperature is about, at least about, or at most about 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., or 220° C., including any intervening ranges.

The difference between the second pressure and the first pressure is preferably at least about 2 bar. In various embodiments, the difference between the second pressure and the first pressure is about, at least about, or at most about 0.1 bar, 0.5 bar, 1 bar, 1.5 bar, 1.8 bar, 2 bar, 2.2 bar, 2.5 bar, 3 bar, 3.5 bar, 4 bar, 4.5 bar, 5 bar, 6 bar, 7 bar, 8 bar, 9 bar, or 10 bar, including any intervening ranges.

In some embodiments, the recycled vapor stream is clean steam. The clean steam may be, or may be derived from, a process vapor stream, a utility vapor stream, a vapor stream obtained from an adjacent facility or process, or a combination thereof, for example.

In some embodiments, the recycled vapor stream is contaminated steam. The contaminated steam may be, or may be derived from, a process vapor stream, a utility vapor stream, a vapor stream obtained from an adjacent facility or process, or a combination thereof, for example.

The recycled vapor stream may contain a pretreatment chemical, such as (but not limited to) acetic acid, formic acid, or a combination thereof.

In some embodiments, step (d) is conducted to directly recycle the digestor vapor to step (b). Alternatively, or additionally, heat contained in the digestor vapor may be utilized to generate fresh vapor that is introduced to step (b) as part or all of the recycled vapor stream.

In some embodiments, the digested stream is fed to a mechanical refiner. In certain embodiments, the digestor vapor is separated from the solid-liquid mixture, and then the solid-liquid mixture is fed to a mechanical refiner.

In some embodiments, the solid-liquid mixture is divided into a solid-rich stream and a liquid-rich stream. The solid-rich stream may be fed to a mechanical refiner.

In some embodiments, the solid-liquid mixture is processed to hydrolyze the cellulose and/or the hemicellulose to monomeric and/or oligomeric sugars. Monomeric and/or oligomeric sugars include, but are not limited to, glucose, xylose, arabinose, mannose, galactose, fructose, sucrose, and oligomers thereof. Optionally, the sugars are processed via sugar separation into a monomer-enriched stream, which may be beneficial for fermentation.

In certain embodiments, the monomeric and/or oligomeric sugars are recovered as one or more sugar products.

In some embodiments, the monomeric and/or oligomeric sugars are fermented to a fermentation product, such as (but not limited to) ethanol, n-butanol, isobutanol, butanediols, succinic acid, lactic acid, or a combination thereof.

In some embodiments, the monomeric and/or oligomeric sugars are catalytically converted to a biofuel or a biochemical, such as (but not limited to) ethanol, ethylene, propylene, butenes, butadienes, bionaphtha (e.g., a mixture of $C_5$-$C_{12}$ hydrocarbons), gasoline, jet fuel, diesel fuel, or a combination thereof.

The pretreated biomass material (the solid-liquid mixture) may alternatively, or additionally, be processed to convert the cellulose into nanocellulose as a biomaterial. The nanocellulose may include cellulose nanofibrils, cellulose nanocrystals, or a combination thereof.

The pretreated biomass material may be alternatively, or additionally, processed in many other ways to produce one or more sugars, biofuels, biochemicals, or biomaterials. For example, the pretreated biomass material may be subjected to pyrolysis, hydropyrolysis, hydrotreating, gasification, steam reforming, combustion, anaerobic digestion, or a combination thereof, or any other biorefinery downstream process that benefits from steps (a)-(d).

Figure 5:
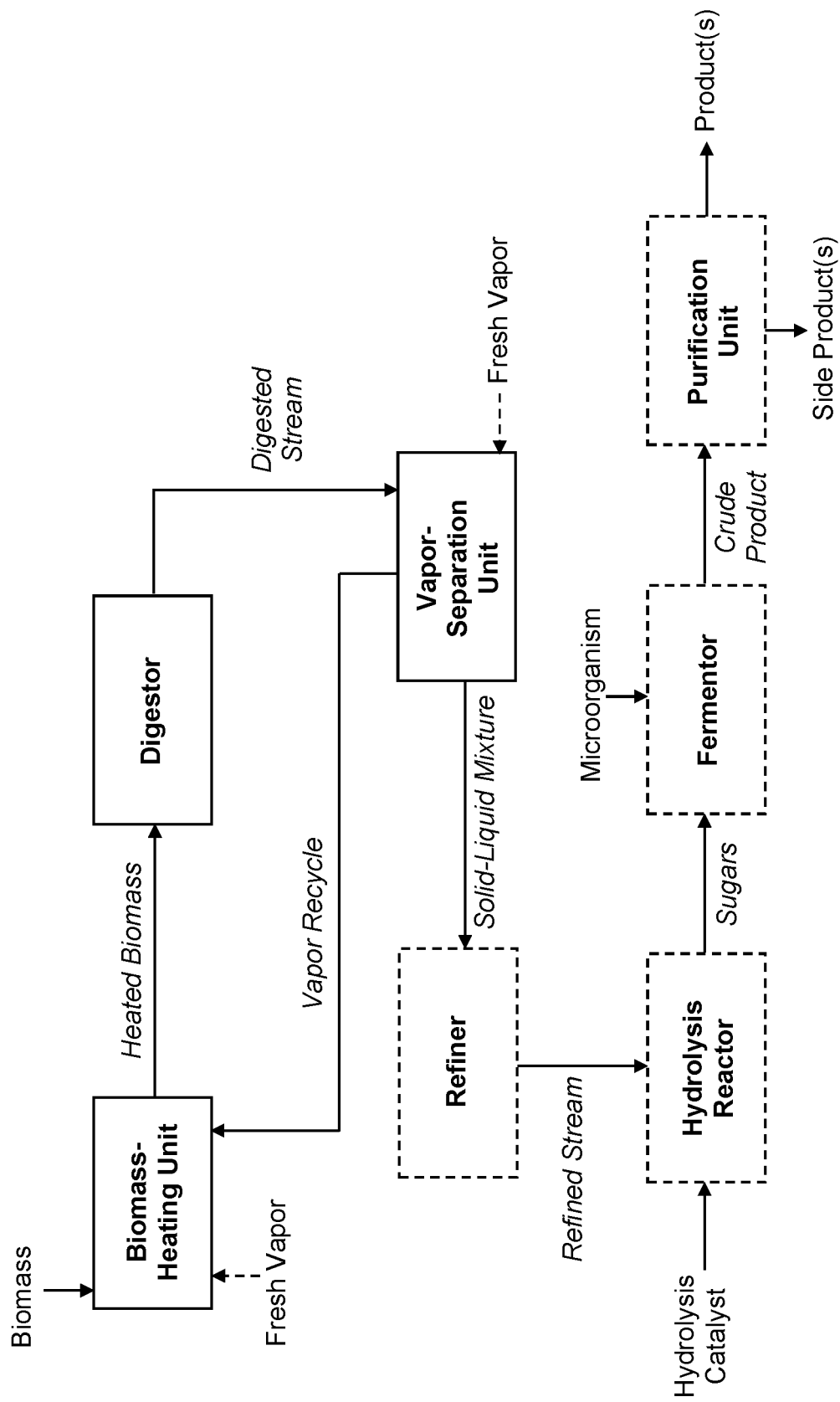

FIG. 5 is an exemplary block-flow diagram depicting a process of converting biomass into pretreated material, in some embodiments employing vapor recycle to a biomass-heating unit. In FIG. 5, biomass is fed to a biomass-heating unit, such as a pre-steaming unit. Fresh vapor (e.g., fresh steam) may be directly injected into the biomass-heating unit, but that is only optional because there is injection of recycled vapor from the downstream vapor-separation unit. The heated biomass is conveyed to a digestor, forming a digested stream. The digested stream is conveyed to a vapor-separation unit, into which fresh vapor is optionally injected. Digestor vapor is recycled back to the biomass-heating unit. The solid-liquid mixture from the vapor-separation unit, after vapor disengagement, is optionally mechanically refined in a refiner, and optionally hydrolyzed in a hydrolysis reactor to generate sugars. The sugars may be fermented to generate a crude product using a microorganism (e.g., yeast or bacteria). The crude product may be purified into the desired product(s), rejecting any side product(s).

Figure 6:
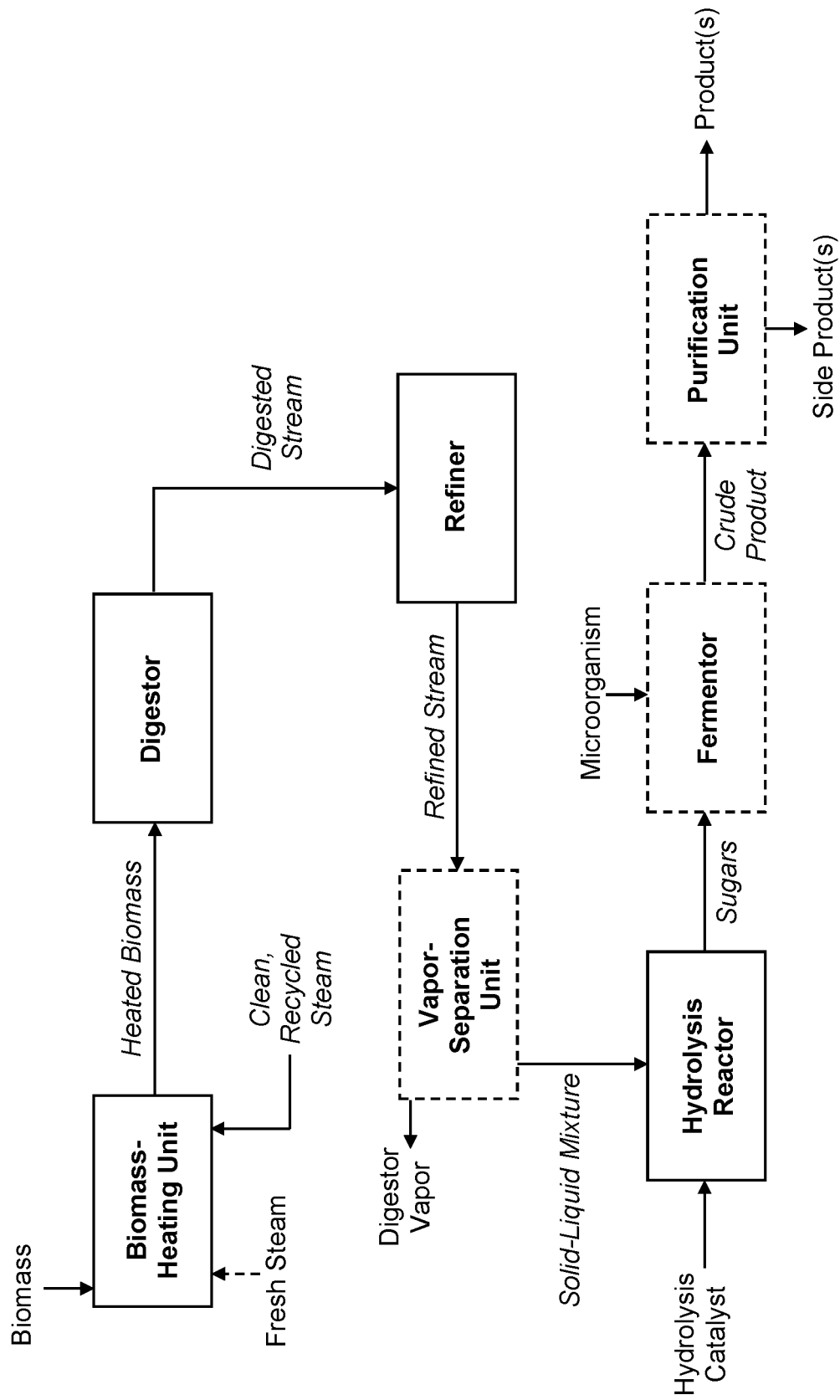

FIG. 6 is an exemplary block-flow diagram depicting a process of converting biomass into pretreated material, in some embodiments utilizing clean, recycled steam in a biomass-heating unit. FIG. 6 is similar to FIG. 5, described above, except that the refiner is disposed upstream of an optional vapor-separation unit. Clean, recycled steam is fed to the biomass-heating unit, which steam may be any recycled steam, not necessarily from the digestor.

Figure 7:
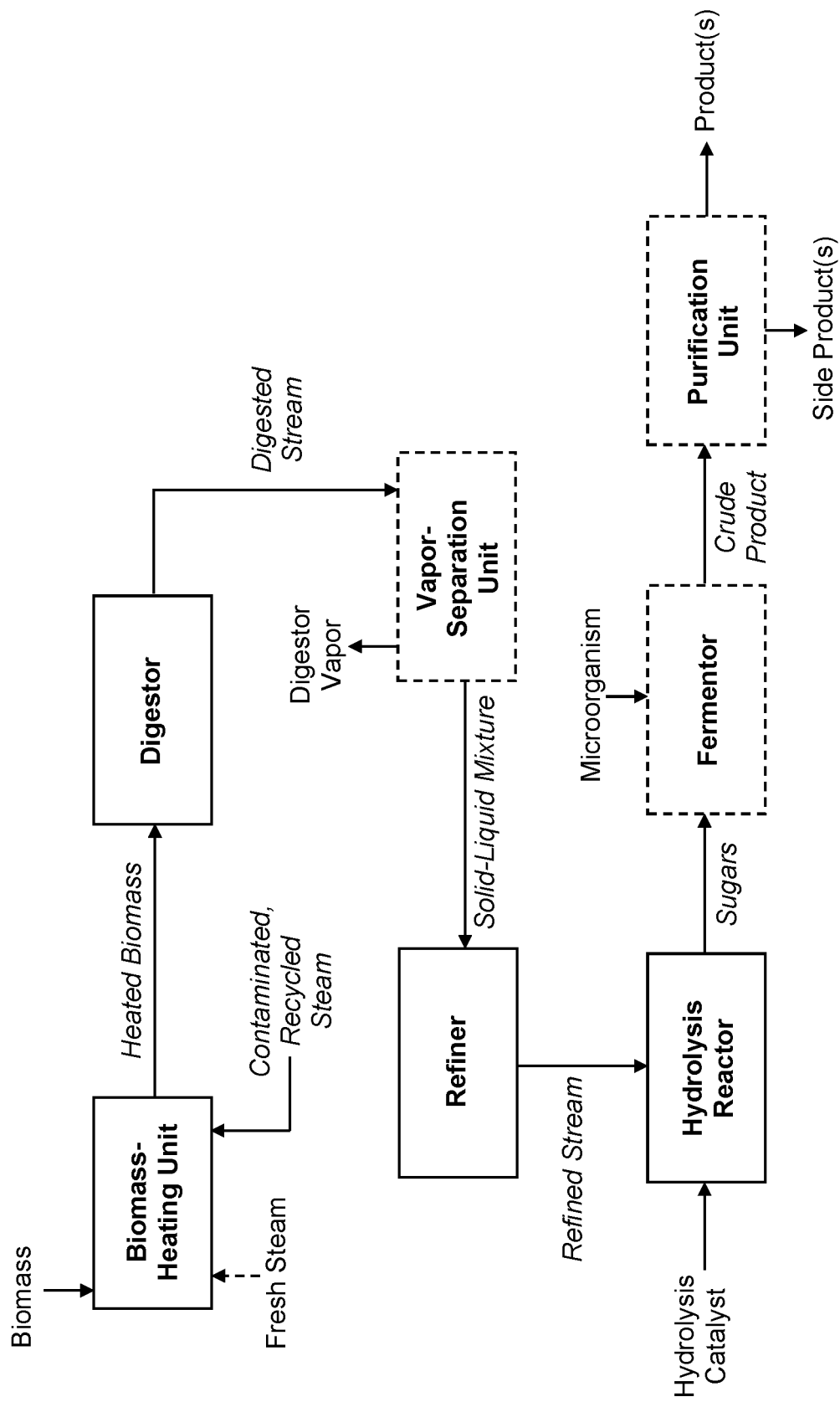

FIG. 7 is an exemplary block-flow diagram depicting a process of converting biomass into pretreated material, in some embodiments utilizing contaminated, recycled steam in a biomass-heating unit. FIG. 7 is similar to FIG. 5, described above, except that the vapor-separation unit is optional. Contaminated, recycled steam is fed to the biomass-heating unit, which steam may be any recycled steam, not necessarily from the digestor. Contaminated, recycled steam may be low-cost utility steam or low-cost steam piped from an adjacent facility, for example.

Figure 8:
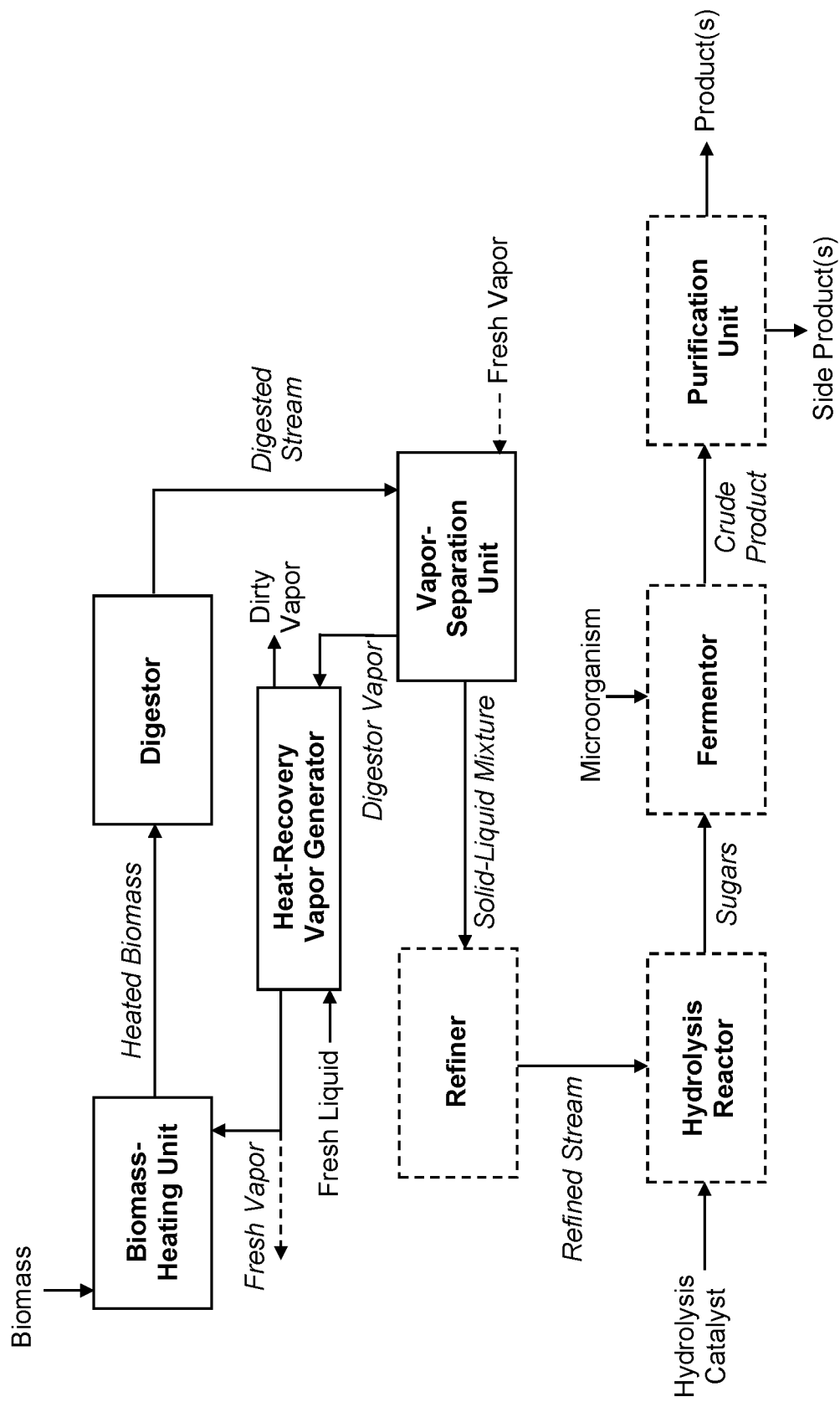

FIG. 8 is an exemplary block-flow diagram depicting a process of converting biomass into pretreated material, in some embodiments employing a heat-recovery vapor generator to recover the heat of the digestor vapor and generate fresh vapor to feed into the biomass-heating unit. FIG. 8 is similar to FIG. 5, described above, except that the digestor vapor is not recycled directly to the biomass-heating unit. Instead, the heat of the digestor vapor is recovered in the heat-recovery vapor generator (e.g., a heat-recovery steam generator), converting digestor vapor into cooled, dirty vapor on one side of a heat exchanger, and converting fresh liquid (e.g., water) into fresh vapor (e.g., fresh steam) on the other side of the heat exchanger. The fresh vapor may be fed to the biomass-heating unit, or may be used for other plant purposes, or both of these. In some embodiments, the heat-recovery vapor generator utilizes a reformer and/or a contact condenser.

Processes for Improving Performance and Energy Efficiency

Other variations of the invention are predicated on the optimization and management of vapor from a biomass digestor.

The pretreated material (digested stream) exiting a biomass digestor may contain compounds that can inhibit fermentation or other conversion, or are undesirable in the final products. Acetic acid, formic acid, hydroxymethylfurfural (HMF), furfural, and derivatives of furfural (e.g., levulinic acid) are examples of undesirable compounds. The pretreated material exiting the digestor is also in a state (temperature, pressure, and possibly pH) that would damage enzymes for enzymatic hydrolysis, resulting in poor hydrolysis performance. The moisture content of the digested stream is typically high which ultimately results in a low hydrolysis product monosaccharide concentration, and additional hydrolysis tank volume.

In addition, the pretreated material exits the digestor with a relatively high enthalpy (high temperature and pressure), compared to the rest of the process. The energy input to the digestor represents a significant portion of the energy used in the production of biochemicals/biofuels. Except for heat losses from the digestor, the energy input is contained in the digestor discharge (the digested stream).

Some variations simultaneously (a) reduce the content of undesirable compounds that can inhibit downstream conversion (e.g., fermentation) in the digestor discharge stream, (b) bring the pretreated biomass to a temperature, pressure, moisture content, and/or pH desirable for enzymatic hydrolysis, and (c) recover the energy embodied in the digestor discharge stream in a highly efficient manner and at a temperature and pressure readily useful in the biochemical/biofuel process, or in a process operated at an adjacent facility. The combined effect of all these benefits is to improve both the process yield and the operating costs. Furthermore, by reducing the energy input required for the biofuel/biochemical process, the process carbon balance is also improved, which as noted earlier can be a critical factor in determining the price the market will pay for the product(s).

A pretreated biomass stream, at a digestor temperature and pressure, is typically a mixture of solids, liquid, and vapor. In some embodiments, water vapor (steam) is removed from a pretreated biomass stream exiting a digestor, using a vapor-separation unit with one or more stages. The water vapor removed from the stream carries away a significant portion of the undesirable compounds (inhibitors) from the solid-liquid mixture, thereby improving downstream conversion (fermentation, catalysis, etc.) compared to such conversion with the inhibitors still present. By separating the vapor, the temperature and pressure of the solid-liquid mixture is reduced to conditions more suitable for enzymatic hydrolysis, for example. Also, by separating the vapor, the moisture content of the stream is reduced which is desirable to avoid too much dilution of product in downstream conversion (e.g., enzymatic or acidic hydrolysis). Finally, the vapor-separation unit is configured and operated so that energy contained in the separated vapor is recovered at a very useful temperature and pressure.

In some embodiments, a first stage of the vapor-separation unit involves the use of a particle-size classifier to separate the biomass (solid and liquid phases) from the vapor phase of the stream exiting the pretreatment digestor. A particle-size classifier is a piece of equipment commonly used in grain milling. A particle-size classifier comprises a hollow, motor-driven, slotted wheel that rotates in a vessel, usually a cyclone. The rotating slotted wheel causes a centripetal acceleration of any matter that enters the open slots of the wheel. The centripetal acceleration is sufficient to cause the biomass to be expelled by the wheel, and fall back into the vessel; however, the water vapor (containing the inhibitors) can pass through the slots of the wheel, thereby exiting the vessel largely free of biomass. The vapor exiting the vessel can then be reused in the plant directly. The solids exit the particle-size classifier through a pressure changer (such as an airlock or a screw) that allows the first stage of water-vapor removal to be performed at a pressure that makes the recovered vapor useful in the rest of the plant. This is typically greater than 0 barg, and is preferably as high a pressure as the pressure changer will allow.

Optionally, the energy content of the vapor may be recovered in a heat exchanger that is configured to generate clean steam, thereby isolating the dirty steam containing the inhibitors and any residual biomass particles. In some embodiments, some of the recovered vapor is reused directly, while some of the vapor is used only for its heat content. The ratio of direct use versus heat use may be dictated by the steam purity requirements in the recovery step (such as a pre-steaming unit).

In particular, in some embodiments, digestor vapor is not recycled directly to the biomass-heating unit. Instead, the heat of the digestor vapor is recovered in a heat-recovery vapor generator, converting digestor vapor into cooled, dirty vapor on one side of a heat exchanger (e.g., a falling-film evaporator), and converting fresh liquid (e.g., water) into fresh vapor (e.g., fresh steam) on the other side of the heat exchanger.

In some embodiments, the vapor-separation unit is a multi-stage vapor separator. A first stage may be a particle-size classifier as described above, for example, or another unit that utilizes centripetal acceleration. A second stage of water-vapor removal may be made at a pressure resulting in a corresponding water vapor saturation temperature that will not damage the enzyme when applied, for example. The second stage may involve the use of a cyclone separator designed for vacuum operation. In some embodiments, a second stage (or an additional stage) may be performed in a particle-size classifier or in another type of vapor/solid-liquid separation equipment.

In some embodiments employing a multi-stage vapor separator, the pressure of the second stage is lower than the pressure of the first stage. If there are three or more stages, all stages may be operated in sequentially descending pressure.

The operating pressure for the second stage may be less than 200 mbara, providing biomass in the range of 50-60° C., for example. Other operating pressures may be used, such that the pressure corresponds to a saturation temperature that is acceptable or desirable.

The water vapor removed in the second stage may contain inhibitors, in which case the inhibitor content is further reduced by the second stage (and additional stages, if used) of the multi-stage vapor-separation unit. Typically, a large fraction of volatile inhibitors, such as furfural, is removed in the first stage, but some volatile inhibitors may remain for non-thermodynamic reasons—e.g., due to mass-transfer limitations or due to reversible chemical bonding with other components. The reduced pressure of the second stage (and additional stages, if used) also assists in the removal of inhibitors (e.g., lignin derivatives) that have lower vapor pressures and which may not be effectively removed at the higher pressure of the first stage.

The moisture content of the biomass is also reduced in the second stage, allowing for a higher total solids content of the biomass entering into hydrolysis process, which can further improve the process energy efficiency and reduce capital cost. The water vapor may be condensed in a vacuum system, with process water as a cooling medium, thereby maximizing the energy recovery of the process. Other cooling mediums may be used for trim cooling, but process water requiring warming is preferably used to the greatest extent possible for condensation of water vapor. Preferably, the solids exit the second stage through a pressure changer, which allows for the maintenance of the vacuum in the second stage, and brings the biomass to the pressure desired for the next step of the process.

Subsequent stages (when present) of water-vapor removal may be operated in a fashion similar to the second stage. Alternatively, or additionally, there may be multiple stages that operate in a fashion similar to the first stage. For example, there may be multiple particle-size classifiers in series, followed by one or more vacuum cyclone separators, all arranged to operate in descending pressures.

By performing the water-vapor removal and temperature reduction in two or more steps, the size of the vessel used for the second step is greatly reduced. If the water vapor was all removed at a low pressure, such as 200 mbara, the vessel of the second step would be a very large vessel at full commercial scale. The vessel would need to be vacuum-rated, and would likely be cost-prohibitive. By removing the water vapor in two or more steps of descending pressures, the energy from the water vapor removed in the first step is recovered at a higher temperature and pressure, making it more useful.

The inhibitor concentration of the pretreated biomass is reduced, resulting in a hydrolysis product with a lower contaminant content, including hydrolysis and/or fermentation inhibitor contaminants. The removal of these compounds is beneficial for downstream processing of the biomass, and ultimately for the value of the final products of the process.

As specific examples, without limitation, the concentration of furfural may be reduced by at least about 75%, the concentration of acetic acid may be reduced by at least about 25%, and the concentration of formic acid may be reduced by at least about 35%. In some embodiments, the reduction of contaminants results in an improvement of about 10% to about 100% in product yield, compared to a process that does not remove contaminants using the disclosed vapor-separation unit. In various embodiments, the reduction of contaminants results in an improvement of product yield of about, or at least about, 5%, 10%, 15%, 20%, 25%, 30%, 40%, 50%, 60%, 70%, 80%, 90%, or 100%, including any intervening ranges, compared to a process that does not remove contaminants using the disclosed vapor-separation unit.

The state of the pretreated biomass is very efficiently adjusted to the temperature, pressure, and moisture content desired for enzyme application. Enzymes may be applied to conduct enzymatic hydrolysis (e.g., cellulose and/or hemicellulose conversion to monomeric sugars), enzymatic isomerization (e.g., glucose conversion to fructose), or other enzymatic reactions.

The removal of heat from the pretreated biomass is difficult using traditional heat-removal methods, due to the poor heat-transfer characteristics of the pretreated biomass. Likewise, moisture removal from biomass is difficult for materials that have no free moisture on the surface, which is typical of pretreated digestor discharge streams. As such, moisture removal by vaporization is another distinct benefit of these variations.

Efficient and effective methods are provided for energy recovery from digestor pretreated biomass streams. Given that the enthalpy of the digested stream represents a significant fraction of the overall energy demand for the entire plant, this is an important benefit of the disclosed process.

Note that all of these variations are equally applicable to vapors other than water vapor (steam). Water vapor represents a common embodiment because water is a low-cost solvent that is almost universally already present in starting biomass feedstocks (unless the feedstock is completely dried). However, from purely a technical perspective, the skilled artisan will recognize that all of these concepts work equally well with other vapors, or mixtures of water vapor with other process vapors. Examples include, but are not limited to, formamide, ammonia, glycerol, methanol, ethanol, acetic acid, hydrogen peroxide, and carbon dioxide.

In some variations, the present invention provides a process for converting a biomass feedstock into a product, the process comprising:
(a) providing a biomass feedstock containing cellulose, hemicellulose, and lignin;
(b) providing a reaction solution comprising a fluid (e.g., a liquid, a vapor, or a liquid-vapor mixture) and optionally a pretreatment chemical;
(c) feeding the biomass feedstock and the reaction solution to a biomass digestor operated to pretreat the biomass feedstock, thereby generating a digested stream comprising a solid-liquid mixture and a digestor vapor;
(d) discharging the digested stream to a vapor-separation unit operated to separate the digestor vapor from the solid-liquid mixture;
(e) optionally recycling at least a portion of the digestor vapor within the process;

(f) conveying the solid-liquid mixture, or a portion thereof, to a hydrolysis reactor operated to hydrolyze the cellulose and/or the hemicellulose to monomeric and/or oligomeric sugars; and (g) converting the monomeric and/or oligomeric sugars to a product.

In some embodiments, the biomass feedstock is a herbaceous feedstock, a woody feedstock, or a mixture of a herbaceous feedstock and a woody feedstock.

In some embodiments, the reaction solution comprises steam. The reaction solution may include a pretreatment chemical, such as a pretreatment chemical selected from the group consisting of an acid, a base, a salt, an organic solvent, an inorganic solvent, an ionic liquid, an enzyme, and combinations thereof, for example. The pretreatment chemical may be a catalyst or a reactant.

In some embodiments, the biomass digestor is operated at a digestor temperature selected from about 100° C. to about 220° C. In various embodiments, the biomass digestor temperature is about, at least about, or at most about 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., 200° C., 205° C., 210° C., 215° C., or 220° C., including any intervening ranges.

In some embodiments, the biomass digestor is operated at a digestor pressure selected from about 1 barg to about 25 barg. In various embodiments, the biomass digestor pressure is about, at least about, or at most about 1 barg, 1.5 barg, 2 barg, 2.5 barg, 3 barg, 4 barg, 5 barg, 6 barg, 7 barg, 8 barg, 9 barg, 10 barg, 11 barg, 12 barg, 13 barg, 14 barg, 15 barg, 20 barg, or 25 barg, including any intervening ranges.

The vapor-separation unit is preferably configured to cause centripetal acceleration of the solid-liquid mixture, thereby separating the solid-liquid mixture from the digestor vapor. In some embodiments, the vapor-separation unit includes a pressure changer that allows the digestor vapor to be utilized in pressurized form.

The digestor vapor that is recovered from the vapor-separation unit may be at a pressure from about 1 barg to about 25 barg. In various embodiments, the digestor vapor is at a pressure of about, at least about, or at most about 1 barg, 1.5 barg, 2 barg, 2.5 barg, 3 barg, 4 barg, 5 barg, 6 barg, 7 barg, 8 barg, 9 barg, 10 barg, 11 barg, 12 barg, 13 barg, 14 barg, 15 barg, 20 barg, or 25 barg, including any intervening ranges.

The vapor-separation unit may be a multi-stage vapor separator, with two, three, or more distinct stages of separation. In some embodiments, at least one stage of the multi-stage vapor separator is configured to cause centripetal acceleration of the solid-liquid mixture, thereby separating the solid-liquid mixture from the digestor vapor. The multi-stage vapor separator may include at least one pressure changer that allows the digestor vapor to be utilized in pressurized form, such as at a pressure from about 1 barg to about 25 barg.

In some embodiments, at least one stage of the multi-stage vapor separator is a vacuum cyclone separator. The vacuum cyclone separator may be operated at an absolute pressure of about 200 mbara or less, for example. In various embodiments, the vacuum cyclone separator is operated at an absolute pressure of about, or at most about 10, 50, 100, 150, 175, 200, 225, 250, 300, 400, 500, 600, 700, 800, 900, 950, or 990 mbara, including any intervening ranges.

Each stage of the multi-stage vapor separator may be configured to cause less than one equilibrium stage of vapor-liquid separation, or about one equilibrium stage of vapor-liquid separation. Since there may be multiple physical stages, the total number of equilibrium stages of vapor-liquid separation of the multi-stage vapor separator may be about 1, 2, 3, 4, 5, or more, including any intervening ranges. Without being limited by speculation, it is believed that a vapor-separation unit, or a stage of a multiple-stage separator, that is configured to cause centripetal acceleration of the solid-liquid mixture, along with vapor release—such as in a particle-size classifier described above—is able to provide at least one complete equilibrium stage of vapor-liquid separation. This is in contrast to a simple flash tank for which it can be difficult or costly to achieve theoretical equilibrium separation due to mass-transfer limitations, for example.

In some embodiments, the vapor-separation unit includes at least one stage that is not a simple flash tank (e.g., a vapor-flash drum). In this context, a "simple flash tank" refers to a unit that causes no centripetal acceleration of the solid-liquid mixture.

In some embodiments, the vapor-separation unit directs a majority of sugar-conversion inhibitors (e.g., fermentation inhibitors) to the digestor vapor, versus the solid-liquid mixture.

In certain embodiments, clean steam is introduced to the vapor-separation unit to reduce the concentration of sugar-conversion inhibitors in the digestor vapor and/or in the solid-liquid mixture. Clean steam may be fresh steam or recovered or recycled steam that has been purified.

In some embodiments, step (e) is conducted. In these embodiments, the digestor vapor is recycled to step (b) for use directly in the reaction solution. Alternatively, or additionally, heat contained in the digestor vapor is utilized to heat the reaction solution, at least in part. Alternatively, or additionally, heat contained in the digestor vapor is utilized to generate fresh vapor that is introduced to step (b) as part or all of the reaction solution.

In some embodiments, the digested stream is mechanically refined prior to step (d)—that is, prior to separating the digestor vapor from the solid-liquid mixture. In certain embodiments, the digested stream is mechanically refined between step (c) and step (d), such as in a blow line between the biomass digestor and the vapor-separation unit.

Figure 12:
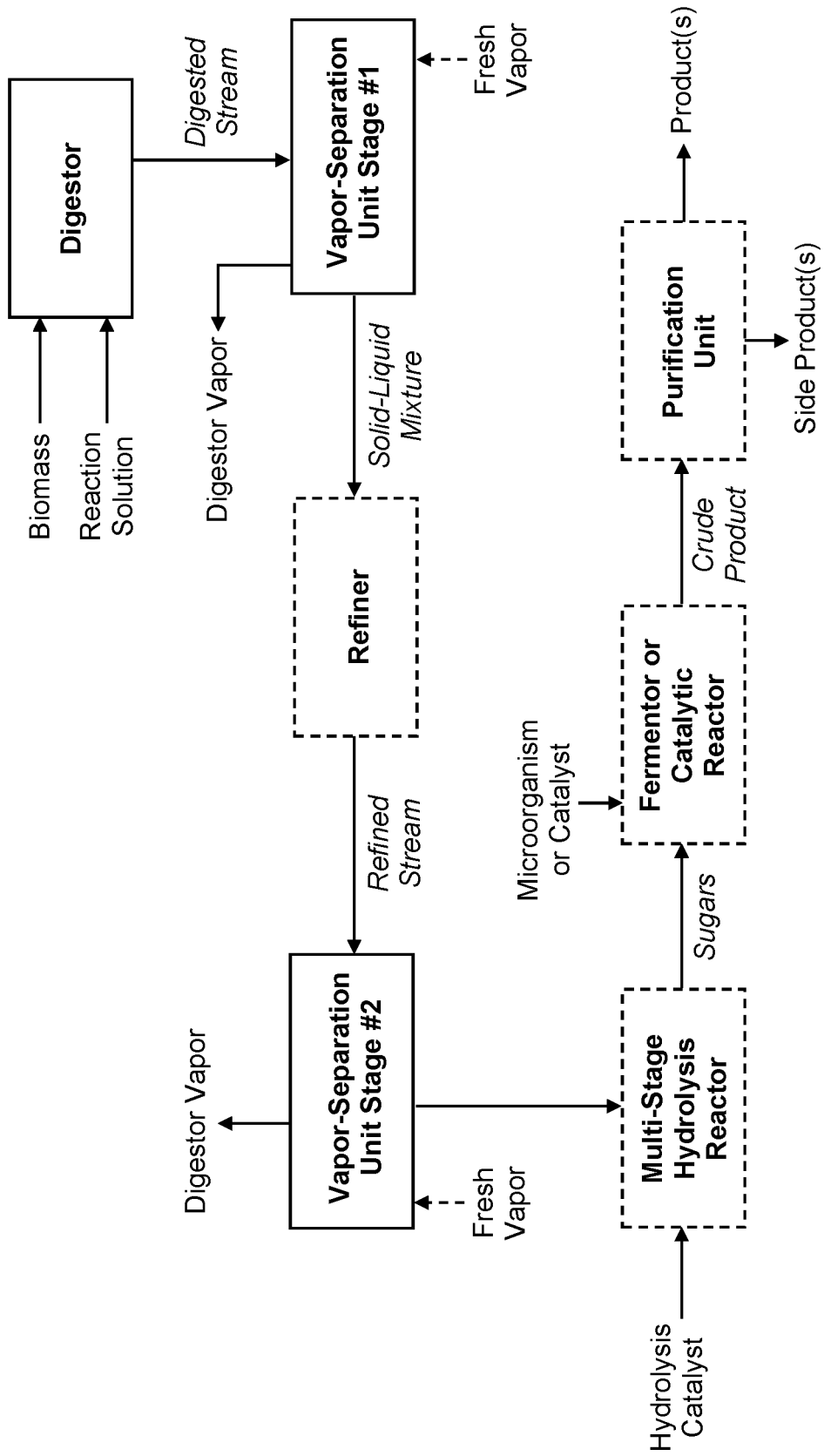

In some embodiments employing a multi-stage vapor separator, a mechanical refiner may be disposed between distinct stages of the multi-stage vapor separator, such as is depicted in FIG. 12.

In some embodiments, the hydrolysis reactor is a multiple-stage hydrolysis reactor, and a mechanical refiner may be disposed between distinct stages of the multiple-stage hydrolysis reactor. For example, a first hydrolysis stage may be configured for largely liquefaction to generate sugar oligomers, and a second hydrolysis stage may be configured to largely hydrolyze sugar oligomers to sugar monomers. The largely oligomer stream (from liquefaction) may be mechanically refined prior to the second hydrolysis stage.

Hydrolysis is discussed in much more detail later in this specification, including preferred hydrolysis conditions (e.g., pH, temperature, and solids concentration), enzymes, and hydrolysis reactor configurations.

Monomeric and/or oligomeric sugars include, but are not limited to, glucose, xylose, arabinose, mannose, galactose, fructose, sucrose, and oligomers thereof. Optionally, the sugars are processed via sugar separation into a monomer-enriched stream, which may be beneficial for fermentation or for catalytic conversion.

In some embodiments, in step (g), the monomeric and/or oligomeric sugars are fermented to a fermentation product, such as (but not limited to) ethanol, n-butanol, isobutanol, butanediols, succinic acid, lactic acid, or a combination thereof.

In some embodiments, in step (g), the monomeric and/or oligomeric sugars are catalytically converted to a biofuel or a biochemical, such as (but not limited to) ethanol, ethylene, propylene, butenes (e.g., 1-butene), butadienes (e.g., 1,3-butadiene), bionaphtha, gasoline, jet fuel, diesel fuel, or a combination thereof.

In some embodiments, in step (g), the monomeric and/or oligomeric sugars are purified and recovered as a sugar product or multiple sugar products.

Figure 9:
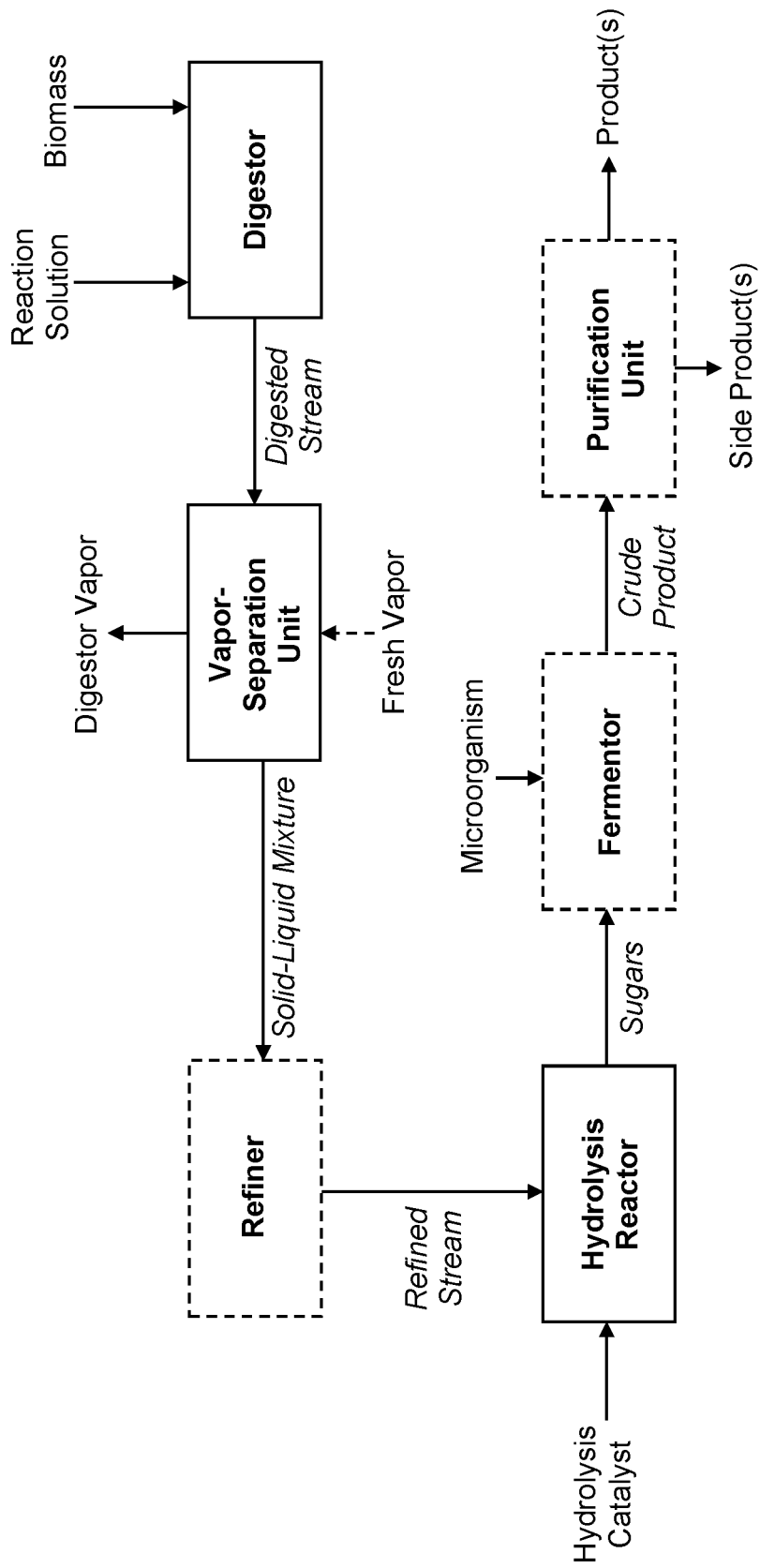

FIG. 9 is an exemplary block-flow diagram depicting a process of converting biomass into products, in some embodiments employing a digestor, a vapor-separation unit, a refiner, and a hydrolysis reactor to generate sugars for conversion to products. In FIG. 9, biomass and a reaction solution are fed to a digestor, either as a pre-mixed stream or separately. The digested stream is fed to a vapor-separation unit, forming a digestor vapor and a solid-liquid mixture that feeds forward. Fresh vapor is optionally injected into the vapor-separation unit. The solid-liquid mixture is optionally refined and is hydrolyzed in a hydrolysis reactor using a hydrolysis catalyst (e.g., enzymes or sulfuric acid), to generate sugars. The sugars may be fermented to generate a crude product using a microorganism (e.g., yeast or bacteria). The crude product may be purified into the desired product(s), rejecting any side product(s).

Figure 10:
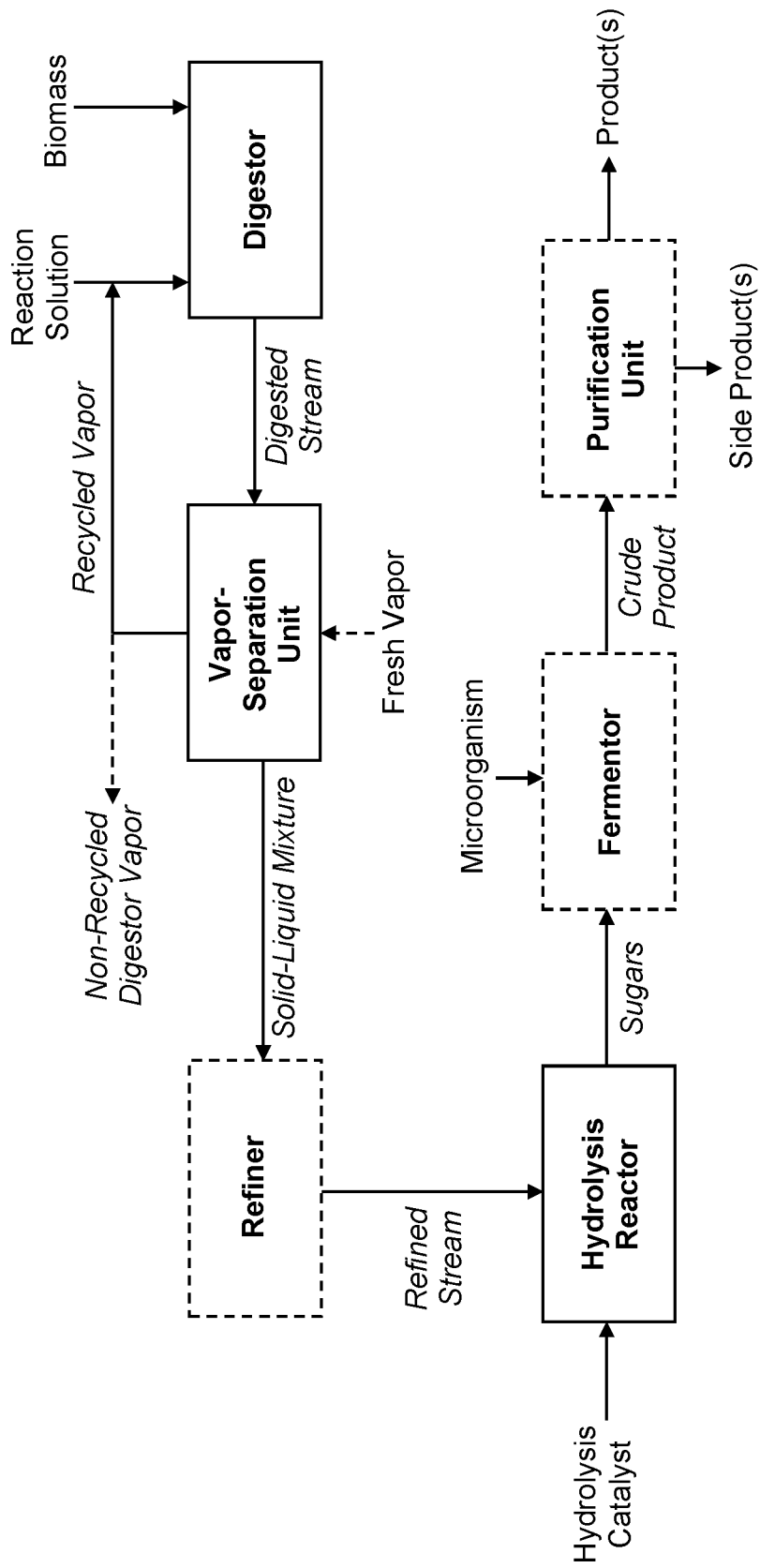

FIG. 10 is an exemplary block-flow diagram depicting a process of converting biomass into products, in some embodiments employing a digestor, a vapor-separation unit, recycle of vapor to the reaction solution fed to the digestor, a refiner, and a hydrolysis reactor to generate sugars for conversion to products. FIG. 10 is similar to FIG. 9, except that the digestor vapor is partially or completely recycled to the digestor by forming some or all of the reaction solution.

Figure 11:
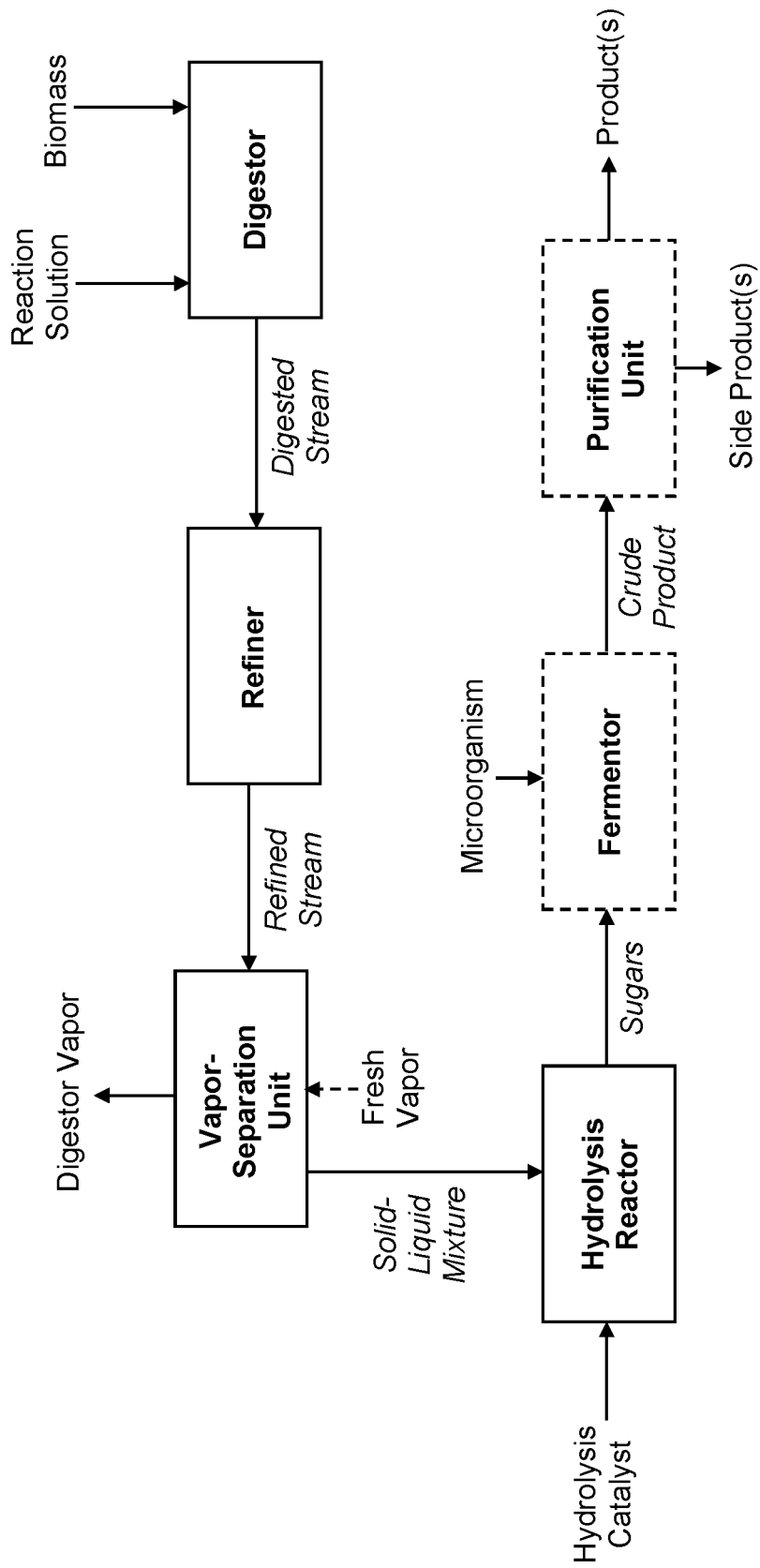

FIG. 11 is an exemplary block-flow diagram depicting a process of converting biomass into products, in some embodiments employing a digestor, a refiner, a vapor-separation unit after the refiner, and a hydrolysis reactor to generate sugars for conversion to products. FIG. 11 is similar to FIG. 9, except that the sequence of the vapor-separation unit and the refiner is switched.

It can be beneficial to place the refiner upstream of the vapor-separation unit because the higher temperature of the digested stream may reduce refiner power consumption. Also, by using this particular sequence, some of the refiner power goes into vaporizing liquid (e.g., water) contained in the biomass, which makes the separation more efficient in the vapor-separation unit and allows for recovery of additional vapor (e.g., steam) at a higher pressure.

FIG. 12 is an exemplary block-flow diagram depicting a process of converting biomass into products, in some embodiments employing a digestor, a multi-stage vapor-separation unit, an optional refiner disposed between vapor-separation unit stages, and a multi-stage hydrolysis reactor to generate sugars for biological or catalytic conversion to products. FIG. 12 is similar to FIG. 9, with the vapor-separation unit being specifically a multi-stage unit with separation stage #1 and separation stage #2, and the optional hydrolysis reactor being specifically a multi-stage reactor. Fresh vapor (e.g., fresh steam) may be injected into the multi-stage vapor-separation unit, which is beneficial to further reduce inhibitor concentration, such as formic acid concentration or terpene concentration. The optional refiner is shown in FIG. 12 as being situated between separation stage #1 and separation stage #s of the multi-stage vapor-separation unit. It should be understood that a refiner may alternatively be disposed between stages of the multi-stage hydrolysis reactor, between the multi-stage vapor-separation unit and the multi-stage hydrolysis reactor, or in multiple locations.

The process may be carried out as a batch, continuous, or semi-continuous process. Each unit within the process may be configured for co-current, countercurrent, or cross-current flow. Each unit within the process may be a static vessel or an agitated vessel, in horizontal, vertical, or slanted orientation.

Process and System Options for all Embodiments

Combinations of any disclosed embodiments may be incorporated in an integrated process.

Figure 13:
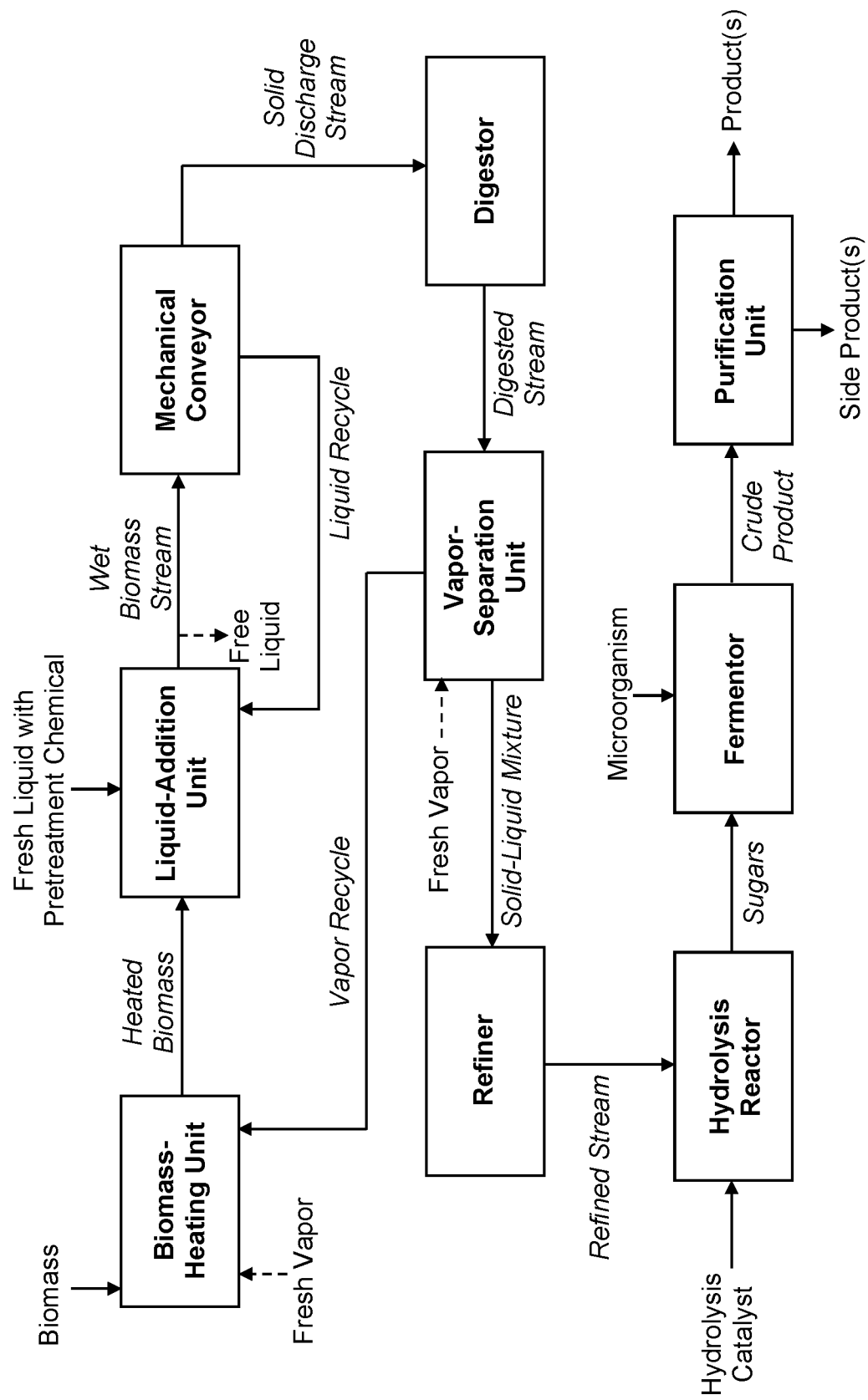

FIG. 13 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a vapor-separation unit, vapor recycle back to the biomass-heating unit, a refiner, a hydrolysis reactor, a fermentor, and a purification unit to generate products. All of the options described above for FIGS. 1-12 apply to FIG. 13.

Figure 14:
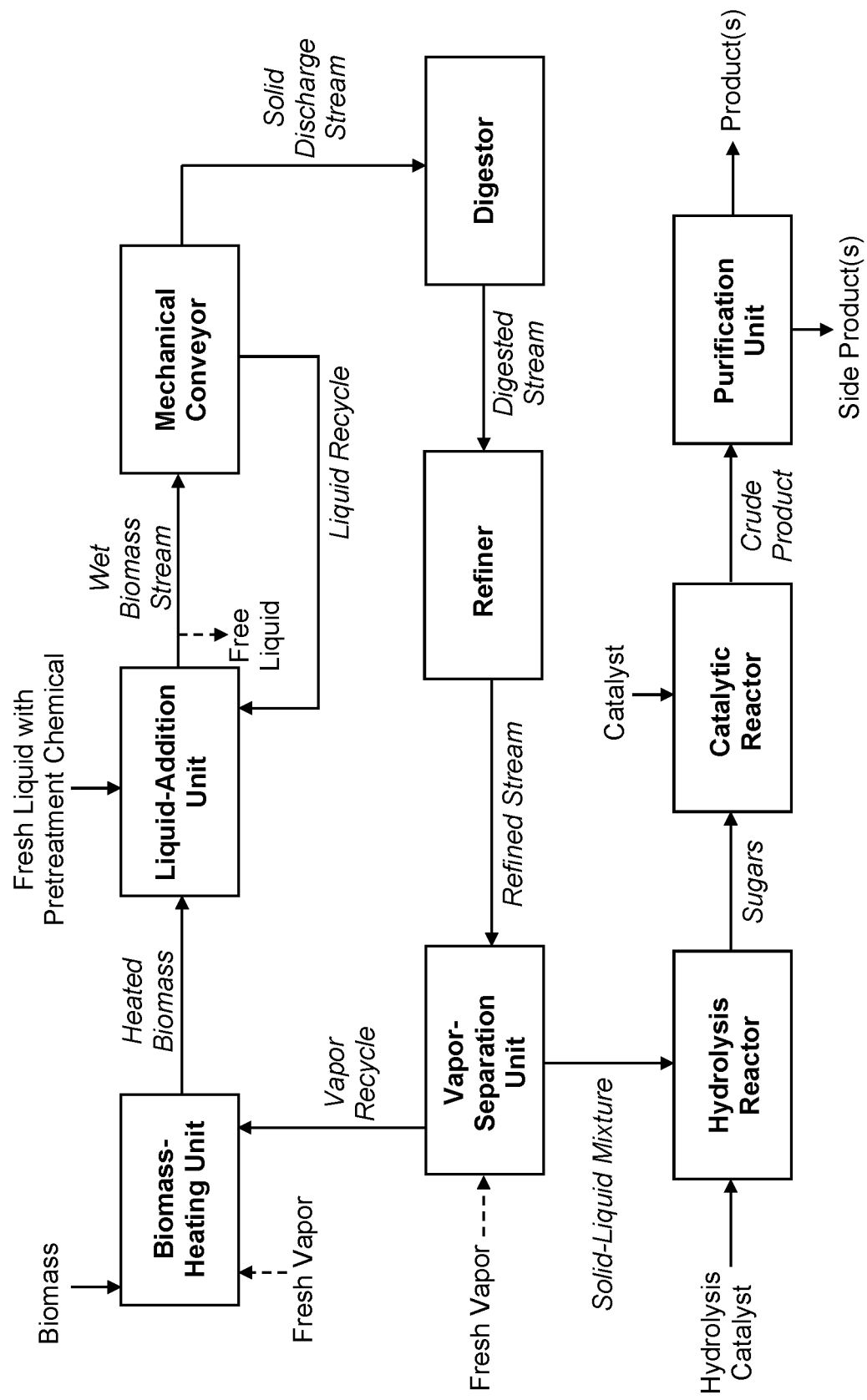

FIG. 14 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a refiner, a vapor-separation unit, vapor recycle to the biomass-heating unit, a hydrolysis reactor, a catalytic reactor, and a purification unit to generate products. All of the options described above for FIGS. 1-12 (such as the location of a mechanical refiner) apply to FIG. 14.

Figure 15:
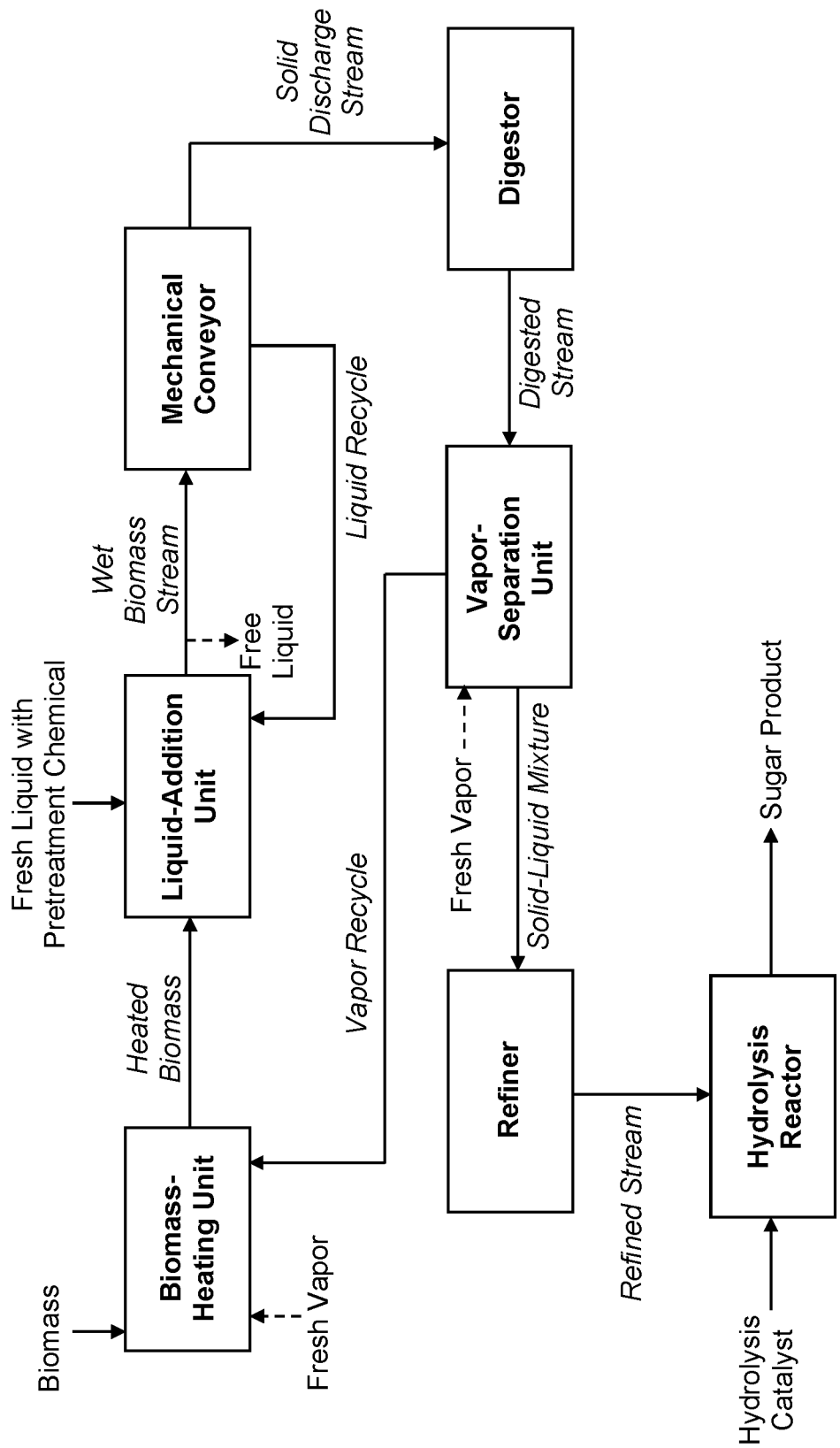

FIG. 15 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a vapor-separation unit, vapor recycle to the biomass-heating unit, a refiner, and a hydrolysis reactor to generate a sugar product. All of the options described above for FIGS. 1-12 apply to FIG. 15.

Figure 16:
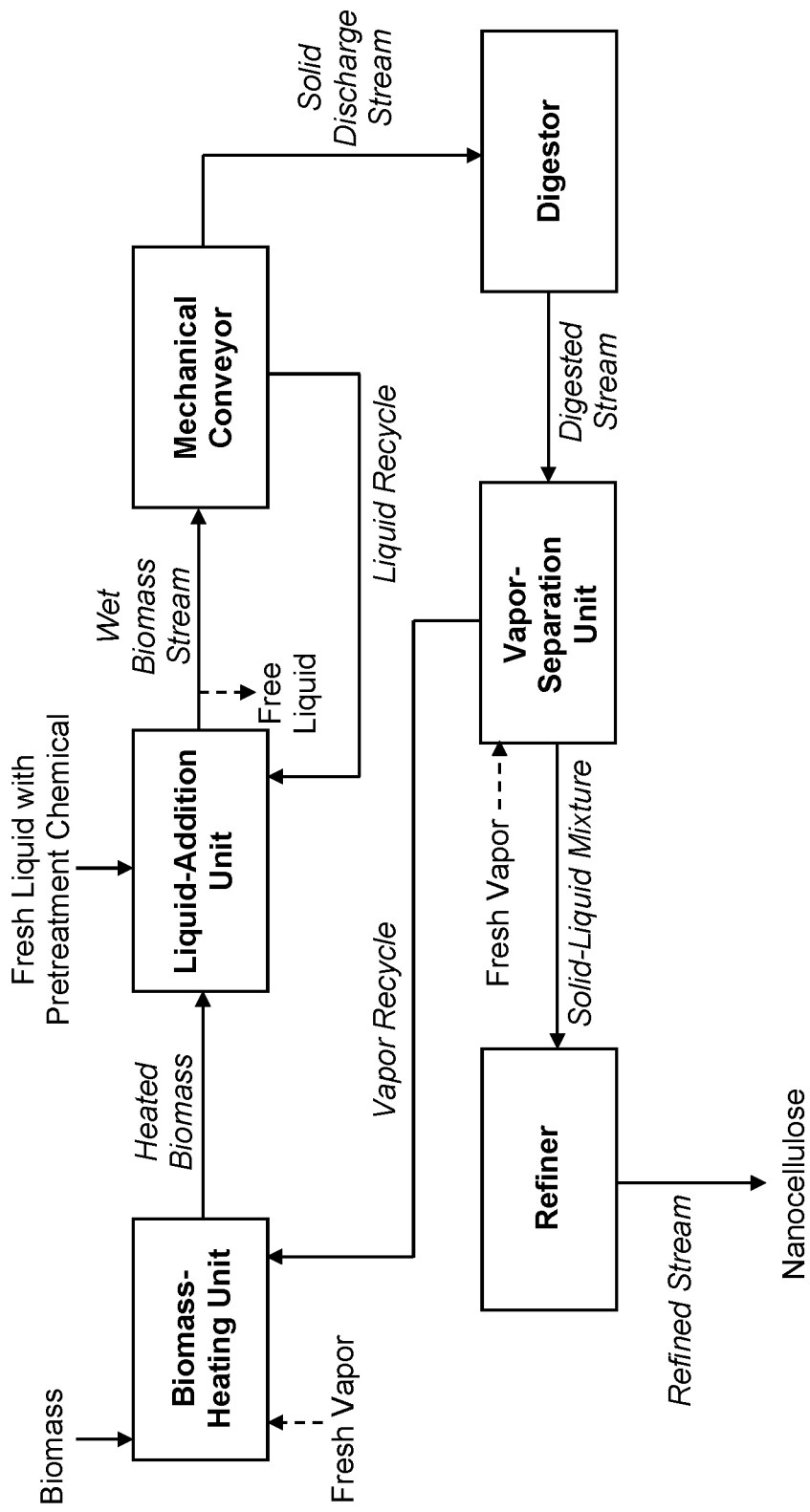

FIG. 16 is an exemplary block-flow diagram depicting a process of converting biomass into products, in some embodiments employing a biomass-heating unit, a liquid-addition unit, a mechanical conveyor with liquid recycle back to the liquid-addition unit, a digestor, a vapor-separation unit, vapor recycle to the biomass-heating unit, and a refiner to generate nanocellulose. All of the options described above for FIGS. 1-12 apply to FIG. 16.

It should be noted that in the block-flow diagrams (FIGS. 1-16), specific unit operations may be omitted in some embodiments and in these or other embodiments, other unit operations not explicitly shown may be included. In each of FIGS. 1 to 16, dotted lines explicitly denote optional streams and units. The invention is not limited to what is shown, or not shown, in the exemplary drawings.

Various valves, pumps, meters, sensors, sample ports, etc. are not shown in the block-flow diagrams of FIGS. 1-16. Additionally, multiple pieces of equipment (rather than single pieces of equipment), either in series or in parallel, may be utilized for any unit operations. Also, solid, liquid, and vapor streams produced or existing within the process may be independently recycled, passed to subsequent steps, or removed/purged from the process at any point.

In FIGS. 1-16, inputs and outputs are labeled with non-italicized text while intermediate streams are labeled with italicized text. Such labeling should not be construed to limit the invention. For example, a portion or all of an intermediate stream may be recovered as a co-product, if desired. Or, a product may be passed to another unit for further processing, in which case the product becomes an intermediate rather than final product.

In FIGS. 1-16, an arrow entering a unit (box) corresponds to direct process introduction, unless otherwise stated. Therefore, when a vapor (e.g., steam) is shown to enter a unit, it will be understand the direct vapor injection is being shown, rather than indirect heat exchange with that unit. Nevertheless, the disclosed processes do not preclude indirect heat exchange with vessel walls using steam, hot oil, electrical resisting heating, or other means.

This disclosure provides a wide variety of processes for biomass pretreatment that enables conversion of the biomass to useful products. "Pretreatment" of biomass refers to treatment of biomass using chemical, mechanical, thermal, and/or electrochemical forces, to produce a product from the biomass or to prepare the biomass for downstream conversion to a product. The downstream conversion may utilize one or more of chemical conversion (e.g., generation of olefins, hydrotreating, oligomerization, etc.), biological conversion (e.g., fermentation or enzymatic reactions), mechanical treatment (e.g., mechanical refining), thermal treatment (e.g., pyrolysis), electrochemical processing (e.g., electrode-assisted lignin processing), or a combination thereof.

"Biomass" refers to any biologically produced organic matter and includes the mass of living or once-living organisms, including plants and microorganisms. Biomass includes both the above-ground and below-ground tissues of plants—for example, leaves, twigs, branches, boles, as well as roots of trees and rhizomes of grasses. The chemical energy contained in biomass is derived from solar energy using the natural process of photosynthesis. Biomass is effectively stored solar energy. Photosynthesis is the process by which plants take in carbon dioxide and water from their surroundings and, using energy from sunlight, convert them into sugars, starches, cellulose, hemicellulose, and lignin.

The biomass feedstock used herein is typically a lignocellulosic feedstock that contains at least cellulose and typically contains lignin. In some embodiments, the lignocellulosic feedstock is a herbaceous feedstock. A herbaceous feedstock has little or no woody tissue and typically persists for a single growing season.

In some embodiments, the biomass feedstock is selected from softwood chips, hardwood chips, timber harvesting residues, tree branches, tree stumps, leaves, bark, sawdust, paper, cardboard, paper waste, off-spec paper pulp, bamboo, corn, corn stover, wheat, wheat straw, rice, rice straw, grass straw, cotton burr, switchgrass, miscanthus, sugarcane, sugarcane bagasse, sugarcane straw, energy cane, energy cane bagasse, energy cane straw, sugar beets, sugar beet pulp, sunflowers, sorghum, canola, algae, miscanthus, alfalfa, switchgrass, fruits, fruit shells, fruit stalks, fruit peels, fruit pits, hemp, vegetables, vegetable shells, vegetable stalks, vegetable peels, vegetable pits, grape pumice, almond shells, pecan shells, coconut shells, coffee grounds, food waste, commercial waste, grass pellets, hay pellets, wood pellets, paper trimmings, food packaging, municipal solid waste, or a combination thereof. The processes and systems of the invention can accommodate a wide range of feedstocks of various types, sizes, and moisture contents. A person of ordinary skill in the art will appreciate that the feedstock options are virtually unlimited.

It will also be recognized that while lignocellulosic biomass is a preferred feedstock, the principles of the invention may also be applied to grain feedstocks, such as those containing primarily starch rather than cellulose. Exemplary starch-containing feedstocks include corn, wheat, cassava, rice, potato, millet, and sorghum.

In some embodiments, a biomass feedstock contains cellulose, hemicellulose, and starch. An example is corn fiber, which typically contains about 35% hemicellulose, 18% cellulose, and 20% starch, as well as some lignin, protein, and oil.

In some embodiments, a biomass feedstock contains cellulose, hemicellulose, and sucrose (a $C_{12}$ sugar). Examples include whole sugarcane and whole energy cane. These materials may be processed to first mechanically remove sucrose juice, with the remaining material (bagasse) then fed to a process described herein. Alternatively, whole sugarcane or whole energy cane may be processed, with the sucrose—or glucose plus fructose derived from sucrose hydrolysis—optionally being fermented to ethanol or another product, or recovered as a sugar product, for example. When sucrose is fermented, it may be fermented to something different than what is made from the cellulose sugars or hemicellulose sugars.

Some process embodiments utilize the relatively easy removal of sucrose from certain feedstocks such as sugarcane, energy cane, or sugarcane bagasse, or energy cane bagasse. In these embodiments, the excess free liquid removed after the liquid-addition unit, or the liquid recycle stream removed from the mechanical conveyor, or both of these streams, may contain significant quantities of sucrose. That sucrose may be used for fermentation of sucrose or other conversion, or for recovery as a sucrose product, for example.

In some embodiments, the biomass feedstock is a botanical feedstock. Botanical feedstocks may include whole plants, plant herbs, plant roots, plant flowers, plant fruits, plant leaves, plant seeds, plant beans, and combinations thereof. An exemplary botanical feedstock is hemp.

The biomass feedstock can be provided or processed into a wide variety of particle sizes or shapes. For example, the feed material can be a fine powder, or a mixture of fine and coarse particles. The feed material can be in the form of large pieces of material, such as wood chips. In some embodiments, the feed material comprises pellets or other agglomerated forms of particles that have been pressed together or otherwise bound, such as with a binder. It is noted that size reduction is a costly and energy-intensive process. Therefore, in preferred embodiments, the biomass feedstock is not in the form of a fine powder.

There are three naturally occurring isotopes of carbon: $^{12}C$, $^{13}C$, and $^{14}C$. $^{12}C$ and $^{13}C$ are stable, occurring in a natural proportion of approximately 93:1. $^{14}C$ is produced by thermal neutrons from cosmic radiation in the upper atmosphere and is transported down to earth to be absorbed by living biological material. Isotopically, $^{14}C$ constitutes a small percentage, but since it is radioactive with a half-life of 5,700 years, $^{14}C$ is radiometrically detectable. Plants take up $^{14}C$ by fixing atmospheric carbon through photosynthesis. Animals then take $^{14}C$ into their bodies when they consume plants or consume other animals that consume plants. Accordingly, living plants and animals have the same ratio of $^{14}C$ to $^{12}C$ as the atmospheric $CO_2$. Once an organism dies, it stops exchanging carbon with the atmosphere, no longer taking up new $^{14}C$. Radioactive decay then gradually depletes the $^{14}C$ in the organism. This effect is the basis of radiometric dating of biological material.

Fossil fuels, such as coal, are made primarily of plant material that was deposited millions of years ago. This period of time equates to thousands of half-lives of $^{14}C$, which means that essentially all of the $^{14}C$ in fossil fuels has decayed. Fossil fuels also are depleted in $^{13}C$ relative to the atmosphere, because they were originally formed from living organisms. Therefore, the carbon from fossil fuels is depleted in both $^{13}C$ and $^{14}C$ compared to biomass carbon.

The difference between the carbon isotopes of recently deceased organic matter, such as that from renewable resources, and the carbon isotopes of fossil fuels, such as petroleum, allows for a determination of the source of carbon in a composition. Specifically, it can be proven whether the carbon in the composition was derived from a renewable resource or from a fossil fuel. The proof of renewability is often important to the market, as explained in the Background.

When the starting feedstock is biomass, which contains renewable carbon, the resulting product also generally contains renewable carbon (one exception is a hydrogen co-product). This can be shown from a measurement of the $^{14}C/^{12}C$ isotopic ratio of the carbon, using for example ASTM D6866. Measuring the $^{14}C/^{12}C$ isotopic ratio of carbon (in solid carbon, or in carbon in vapor form, such as CO, $CO_2$, or $CH_4$) is a proven technique.

A similar concept can be applied to hydrogen, in which the $^{2}H/^{1}H$ isotopic ratio is measured (2H is also known as deuterium, D). Fossil sources tend to be depleted in deuterium compared to biomass. See Schiegl et al., "Deuterium content of organic matter", *Earth and Planetary Science Letters*, Volume 7, Issue 4, 1970, Pages 307-313; and Hayes, "Fractionation of the Isotopes of Carbon and Hydrogen in Biosynthetic Processes", Mineralogical Society of America, National Meeting of the Geological Society of America, Boston, MA, 2001, which are hereby incorporated by reference herein.

In particular, the natural deuterium content of organically bound hydrogen shows systematic variations that depend on the origin of the samples. The hydrogen of both marine and land plants contains several percent less deuterium than the water on which the plants grew. Coal and oil is further depleted in deuterium with respect to plants, and natural gas is still more depleted in deuterium with respect to the coal or oil from which it is derived. "Renewable hydrogen" may be determined by correlating the $^{2}H/^{1}H$ isotopic ratio with the renewability of the starting feedstock. On average, water contains about 1 deuterium atom per 6,400 hydrogen (H) atoms. The ratio of deuterium atoms to hydrogen atoms in renewable biomass is slightly lower than 1/6,400, and the ratio of deuterium atoms to hydrogen atoms in non-renewable fossil sources (e.g., mined natural gas) is even lower than the ratio for renewable biomass. Therefore, the $^{2}H/^{1}H$ isotopic ratio correlates with renewability of the hydrogen: higher $^{2}H/^{1}H$ isotopic ratios indicate a greater renewable hydrogen content.

Renewable hydrogen may be obtained in a number of ways, in the context of this disclosure. For example, the digested stream, or a solid-rich stream derived therefrom, may be gasified to produce syngas ($H_2$ and CO), followed by water-gas shift to generate high $H_2$/CO ratios and/or separation to recover $H_2$. The digested stream, or a solid-rich stream derived therefrom, may be subjected to anaerobic digestion to make methane which is then steam-reformed or partially oxidized to generate syngas, from which $H_2$ may be obtained. Another approach is to separate a lignin-rich co-product from the digestor, from a hydrolysis reactor, from a fermentor, or from a distillation column and then gasify that lignin to generate syngas, from which $H_2$ may be obtained. These $H_2$ co-products represent renewable hydrogen.

Renewable hydrogen can be recognized in the market in various ways, such as through renewable-energy standards, renewable-energy credits, renewable identification numbers, and the like. As just one example, an oil refinery utilizing renewable hydrogen in producing jet fuel can receive renewable-energy credits for such $H_2$ content.

Importantly, a renewable product (or process) does not necessarily mean a sustainable product (or process). For example, an entirely renewable product could be made from biomass but at a high energy demand which means that the greenhouse-gas generation associated with the product is high (assuming nuclear energy use is not significant). The energy demand of a process can be characterized by the process carbon intensity, which is the ratio of greenhouse-gas emissions (usually on a $CO_2$-equivalent basis) to the energy content of the products. The difference between renewability and sustainability is the reason for sustainable standards such as those for sustainable aviation fuel ("SAF").

There is extraordinary commercial interest in sustainable aviation fuel, commonly referred to simply as SAF. SAF recycles $CO_2$ emissions that were emitted previously and subsequently absorbed from the atmosphere during biomass production. SAF must have the same characteristics as conventional jet fuel so that manufacturers do not need to redesign engines or aircraft, and so that fuel suppliers and airports do not need to build new fuel delivery systems. Taking into consideration that the same aircraft can be fueled in different countries, international specifications have been adopted for jet fuels.

A widely utilized standard to ensure jet fuel is fit for purpose is American Society for Testing Materials (ASTM) standard number D1655, which is incorporated by reference. ASTM D1655 sets requirements for criteria such as composition, volatility, fluidity, combustion, corrosion, thermal stability, contaminants, and additives, to ensure that the fuel is compatible when blended.

The drop-in condition is a major requirement for the aviation industry, to ensure safety and performance that is equivalent to conventional Jet A or Jet A1 kerosene. The standard regulating the technical certification of SAF is ASTM D7566, which is incorporated by reference. The alcohol-to-jet (ATJ) pathway has been approved by ASTM for incorporation into ASTM D7566 in 2018 using ethanol at a blend limit of 50%. The ATJ process utilizes dehydration, oligomerization, and hydroprocessing to convert ethanol to hydrocarbon fuel blending components. There are other approved pathways for SAF, and additional pathways may be approved in the future, such as catalyzed reactions of sugars into hydrocarbons.

In some embodiments, aviation fuel, such as SAF, is produced starting with ethanol, n-butanol, isobutanol, or other alcohols. In the case of ethanol, for example, catalytic conversion of ethanol into hydrocarbons typically involves three steps prior to purification to meet fuel specifications: ethanol dehydration to ethylene; ethylene oligomerization to higher-molecular-weight hydrocarbons; and hydrogenation to saturate the oligomers to produce a finished renewable fuel that can be blended at high levels into conventional fuels, or used directly in existing engines. Published designs generally require high reaction temperatures and pressures, as well as externally supplied hydrogen. See Hannon et al., "Technoeconomic and life-cycle analysis of single-step catalytic conversion of wet ethanol into fungible fuel blendstocks", *PNAS*, Vol. 117, No. 23, Pages 12576-12583 (2020), which is hereby incorporated by reference. An alternative approach involves one-step conversion of ethanol-water mixtures into hydrocarbons and water over a vanadium-containing zeolite catalyst. See, for example, U.S. Pat. No. 9,533,921 issued Jan. 3, 2017 to Narula et al., which is incorporated by reference.

In various embodiments, including those shown in FIGS. 1-16, alcohols such as ethanol are converted to sustainable gasoline, sustainable diesel fuel, sustainable aviation fuel, or a combination thereof. Such processes employ a number of reactors, including for example a biomass digestor, a hydrolysis reactor, a fermentor, a catalytic reactor, and potentially other reactors.

As used in this specification, a "reactor" can refer to a single reaction vessel or to a reaction zone contained within a reaction vessel. When a single reactor contains multiple reaction zones, the number of zones can be 2, 3, 4, or more. As used herein, "zones" are regions of space within a single physical unit, or are physically separate units, or a combination thereof. For a continuous reactor, the demarcation of zones can relate to structure, such as the presence of flights within the reactor or distinct heating elements to provide heat to separate zones. Alternatively, or additionally, the demarcation of zones in a continuous reactor can relate to function, such as distinct temperatures, fluid flow patterns, solid flow patterns, or extent of reaction. There are not necessarily abrupt transitions from one zone to another zone. Zone-specific process monitoring and control may be employed, such as through FTIR sampling, enabling dynamic process adjustments.

It should also be noted that multiple physical apparatus can be employed for a reactor, in series or in parallel. For example, a reactor can be two physical reaction vessels operated in series (sequentially), in parallel, or a hybrid thereof.

Material can generally be conveyed into and out of a reactor or vessel by pumps, screws, and the like. Material can be conveyed mechanically by physical force, pressure-driven flow, pneumatically driven flow, centrifugal flow, gravitational flow, fluidized flow, or some other known means of moving material.

The mode of operation for a reactor can be continuous, semi-continuous, batch, or any combination or variation of these. In some embodiments, the reactor is a continuous, countercurrent reactor in which two phases flow substantially in opposite directions. The reactor can also be operated in batch but with simulated countercurrent flow of vapors, such as by periodically introducing and removing vapor from the batch vessel.

Various flow patterns can be desired or observed in a reactor. With chemical reactions and simultaneous separations involving multiple phases in multiple reactor zones, the fluid dynamics can be quite complex. For example, the flow of solids can approach plug flow (well-mixed in the radial dimension) while the flow of vapor can approach fully mixed flow (fast transport in both radial and axial dimensions). Multiple inlet and outlet ports for vapor can contribute to overall mixing.

If desired, a process unit may be agitated in a variety of ways. In some embodiments, a process unit is disposed in physical communication with an external vibrating motor that physically vibrates the process unit to mix the contents. In some embodiments, the process unit is configured with a stirring mechanism such as an internal impeller or paddle. In some embodiments, the process unit is agitated by rolling or tumbling the unit in an automated manner. In some embodiments, the process unit is agitated via continuous recycling of a liquid that is pumped out of and back into the process unit. In similar embodiments, continuous recirculation of an inert gas (such as Ar or $N_2$) through the process unit may be employed to enhance the mixing efficiency. Combinations of any of these agitation techniques, or others (e.g., sonication), may be employed in certain embodiments.

The specific agitation rate is not regarded as critical to the invention, and one skilled in the art will be able to employ an effective agitation rate. For example, in the case of an external vibrating motor, the vibration frequency may be monitored or controlled. In the case of an internal impeller, the impeller revolution frequency (e.g., revolutions per minute, rpm) may be monitored or controlled. In the case of a continuous purge and reinjection of fluid (liquid or vapor), the recycle flow rate may be monitored or controlled, and so on. For any type of agitation, the fluid Reynolds Number (Re) may be monitored or controlled, such as by use of tracers to measure velocity distribution within the unit. The Re may be based on chamber diameter or on the impeller diameter in the case of an internal impeller, for example. In various embodiments, an effective internal Re may be from about 100 to about 10,000, for example. The flow pattern within the process chamber may be laminar or turbulent. In some embodiments, a non-agitated process unit (Re=0) is employed.

A unit may include a subsystem for adjusting temperature, pressure, and/or residence time within the unit. A subsystem may be configured to vary parameters, such as over a prescribed protocol, or in response to measured variables. For example, an unintended change in reactor pressure may be compensated by a change in reactor temperature and/or residence time. As another example, temperature may be maintained constant (isothermal operation) or pressure may be maintained constant (isobaric operation). The subsystem may utilize well-known control logic principles, such as feedback control and feedforward control. Control logic may incorporate results from previous experiments or production campaigns.

In some embodiments, a reaction probe is disposed in operable communication with a reaction zone. Such a reaction gas probe can be useful to extract vapors, liquids, or solids and analyze them, in order to determine extent of reaction, pH, temperature, or other process monitoring. Then, based on the measurement, the process can be controlled or adjusted in any number of ways, such as by adjusting processing rate, temperature, pressure, agitation, additives, and so on. Process adjustments based on the measurements, if deemed necessary or desirable, may be made using well-known principles of process control (feedback, feedforward, proportional-integral-derivative logic, etc.).

For example, acetic acid concentration in the vapor phase of a reactor may be measured using a gas probe to extract a sample, which is then analyzed using a suitable technique, such as gas chromatography, GC; mass spectroscopy, MS; GC-MS, or Fourier-Transform Infrared Spectroscopy, FTIR.

Safety considerations may be applied to the process and system. A unit may include protective devices (e.g., a safety release valve) that automatically activate when the temperature or pressure exceeds a maximum value, for example. Practical safety-related design may be built into the system as well. Those skilled in the art will understand how to design safe units.

In this disclosure, a "reaction solution" is generally a fluid, which may be a liquid, a vapor, or a mixture of a liquid and a vapor, that assists in one or more chemical reactions.

A reaction solution may also contain a solid in addition to the fluid, wherein the solid is dissolved and/or suspended. A reaction solution may contain a reactant, a catalyst, a solvent, a carrier, an additive, a diluent, or a combination thereof.

In this disclosure, "impregnate" and "impregnation" refer to the introduction of a reaction solution into the biomass feedstock, such that the reaction solution is contained within pores of the biomass structure as well as space between biomass particles. In some cases, the reaction solution suspends the biomass feedstock and potentially dissolves at least some of the biomass feedstock. For convenience, reference herein to "biomass pores" includes reference to open pores, interconnected pores, surface openings, and space between biomass particles.

In this disclosure, "solution" refers not only to a true thermodynamic solution with a single phase but also multiphase systems with multiple liquid phases, a solid phase dissolved and/or suspended in a liquid phase or multiple liquid phases, a vapor phase dissolved or entrained in one or more liquid phases, and so on.

The presence of non-condensable gases in the pore structure of biomass hinders the entry of the desired impregnation liquid from entering the biomass pores. This technical problem hinders the bulk flow by convection and/or diffusion of the reaction solution into biomass pores. If the biomass pore walls of the biomass structure are hydrophobic, the surface tension of an aqueous solution will hinder the wetting and ingress of the liquid into the pore structure. If the biomass pore walls of the biomass structure are hydrophilic, the surface tension of a non-polar liquid will hinder the wetting and ingress of the liquid into the pore structure.

As intended herein, a "non-condensable gas" is a molecule that is normally considered by a skilled chemical engineer to be non-condensable or difficult to condense, requiring cryogenic temperatures or very high pressures. Non-condensable gases herein may include gases with a condensation point of less than 0° C. (typically, −50° C. or less) at atmospheric pressure.

The process in some variations preferably includes removal of non-condensable gases from biomass pores by means of passing condensable vapor through the biomass-heating unit, or another vessel containing the biomass, preferably in a countercurrent fashion. After the non-condensable gases (e.g., oxygen, nitrogen, and/or carbon dioxide) have been removed from the biomass, a liquid containing the chemical with which the biomass is to be impregnated is introduced. The liquid introduced is below the condensation temperature for the condensable vapor used in the non-condensable gas removal, and therefore results in the condensation of the condensable vapor in the biomass, drawing the desired impregnation liquid (which optionally contains a pretreatment chemical) deeper into the biomass pores compared to simple application of the liquid to the surface of the biomass.

Some processes disclosed herein improve the impregnation of lignocellulosic biomass (herbaceous biomass or other types of biomass) by utilizing the pore structure of the biomass to more evenly distribute a chemical within the biomass particle. The chemical may be a catalyst to assist in the digestion of the biomass, or any other chemical (including water) for which an even distribution throughout the biomass is desirable.

In some embodiments, biomass is directly heated with vapor (such as steam), with an added advantage that this may be performed with relatively low-pressure steam, which can be recovered from other unit operations of the plant. Direct heating of the biomass improves the overall thermal efficiency of the process.

In addition, recovery of compounds contained in the vapor is possible, since those compounds enter the process stream due to direct biomass heating. Certain compounds (e.g., acetic acid) may assist the biomass-conversion process and/or must be removed from the vapor stream, prior to release to the atmosphere.

The process, in some embodiments, overcomes the technical problem that prevents the bulk flow of liquid into the pore structure of biomass. One technical solution includes removing non-condensable gases with a condensable vapor that is subsequently condensed by the temperature change caused by the introduction of a separate liquid.

Some variations utilize a process for impregnating a biomass feedstock with a reaction solution, the process comprising:

(a) providing a biomass feedstock that contains non-condensable gases within biomass pores of the biomass feedstock;

(b) introducing a condensable vapor into the biomass pores to remove at least some of the non-condensable gases out of the biomass pores, thereby generating an intermediate biomass material, wherein at least a portion of the condensable vapor remains within the biomass pores;

(c) exposing the intermediate biomass material to a liquid solution to (i) infiltrate the liquid solution into the biomass pores and (ii) condense at least a portion of the condensable vapor to form a condensed liquid contained within the biomass pores, thereby generating an impregnated biomass material containing a reaction solution comprising the liquid solution and the condensed liquid; and (d) recovering or further processing the impregnated biomass material.

The biomass feedstock may be a lignocellulosic biomass feedstock, such as (but not limited to) hardwoods, softwoods, sugarcane bagasse, sugarcane straw, energy cane, corn stover, corn cobs, corn fiber, wheat straw, rice straw, or combinations thereof.

In some embodiments, the non-condensable gases include one or more gases selected from the group consisting of air, oxygen, nitrogen, carbon dioxide, argon, hydrogen, carbon monoxide, and methane.

In some embodiments, the condensable vapor is steam. The steam may be clean steam, dirty steam, waste steam, recycled steam, acidic steam, or another source of steam, or a combination thereof. Dirty steam or waste steam may contain vapor-phase contaminants such as acetic acid, formic acid, formaldehyde, acetaldehyde, methanol, lactic acid, furfural, 5-hydroxymethylfurfural, furans, uronic acids, phenolic compounds, terpenes, and sulfur-containing compounds. Dirty steam or waste steam may entrained solid contaminants, such as cellulose, lignin, monosaccharides, polysaccharides, ash, etc.

The steam may be at various steam pressures and steam qualities. Steam may be steam that was originally introduced to the biomass (before or within the digestor) as steam, liquid water, or a combination thereof, and optionally with pretreatment chemicals. Steam may be derived from water that was present in the starting biomass feedstock.

In some embodiments, the condensable vapor is a vapor of a $C_1$-$C_4$ alcohol, such as methanol, ethanol, n-butanol, or isobutanol. Typically, the condensable vapor is a vapor of a component that is intended to be in the reaction solution. For example, when the reaction solution will contain ethanol as a solvent for lignin, then the condensable vapor may be an ethanol vapor.

In preferred embodiments, the liquid solution contains water. For example, the liquid solution may be an aqueous solution containing an acid, a salt of the acid, a base, a salt of the base, or a combination thereof. In certain embodiments, the liquid solution consists essentially of water. Impurities may be present in a liquid solution that consists essentially of water.

Water sources can include direct piping from process condensate, other recycle water, wastewater, make-up water, boiler feed water, or city water, for example. Water can optionally first be cleaned, purified, treated, ionized, distilled, and the like. When several water sources are used, various volume ratios of water sources are possible.

When an acid is included in the liquid solution, the acid may be a sulfur-containing acid, such as an acid selected from the group consisting of sulfur dioxide, sulfur trioxide, sulfurous acid, sulfuric acid, sulfonic acid, lignosulfonic acid, and combinations thereof.

Other acids may be employed. In various embodiments, an acid is selected from the group consisting of sulfuric acid, sulfurous acid, sulfur dioxide, nitric acid, phosphoric acid, hydrochloric acid, acetic acid, formic acid, levulinic acid, maleic acid, lactic acid, and combinations thereof. The acid may be a Bronsted acid or a Lewis acid. An example of a Lewis acid is sulfur dioxide.

When a base is included in the liquid solution, the base may be selected from the group consisting of ammonia, ammonium hydroxide, sodium hydroxide, potassium hydroxide, magnesium hydroxide, calcium hydroxide, and combinations thereof. The base may be a Bronsted base or a Lewis base.

In certain embodiments, the liquid solution includes an enzyme, such as an enzyme selected from the group consisting of cellulase, endoglucanase, exoglucanase, beta-glucosidase, hemicellulase, ligninase, and combinations thereof. The enzyme may be utilized as a pretreatment chemical, separately from any enzyme used downstream, such as in hydrolysis. Ligninase may be used as a pretreatment chemical to remove or modify lignin in the biomass, to improve biomass digestion or to assist in recovery of lignin, for example.

The liquid solution may contain a solvent for lignin. For example, the solvent for lignin may be selected from the group consisting of a linear alcohol, a branched alcohol, an aromatic alcohol, a ketone, an aldehyde, an ether, a non-oxygenated hydrocarbon, an ionic liquid, and combinations thereof. Exemplary solvents for lignin include methanol, ethanol, ethylene glycol, 1-propanol, 2-propanol, propanediol, glycerol, 1-butanol, 2-butanol, isobutanol, butanediol, 1-pentanol, 1-hexanol, cyclohexanol, and combinations thereof.

When the liquid solution includes a solvent for lignin, there may or may not also be water in the liquid solution. Also, when the liquid solution includes a solvent for lignin, there may or may not also be a pretreatment catalyst in the liquid solution. For example, in the case of ethanol as a solvent for lignin and sulfur dioxide as a pretreatment catalyst, a liquid solution may contain ethanol, water, and $SO_2$; ethanol and water; water and $SO_2$; ethanol and $SO_2$; water only; or ethanol only.

All of the vapor-liquid processing described in this specification may be applied to a vapor other than steam. The thermodynamics of the liquids and vapors present will dictate the necessary temperature and pressures in various units, in order to take advantage of the principles set forth herein. Water is a low-cost solvent that is almost universally already present in starting biomass feedstocks (unless the feedstock is completely dried). However, from purely a technical perspective, the skilled artisan will recognize that the disclosed processes work equally well with other vapors, or mixtures of water vapor with other process vapors. Examples include, but are not limited to, carbon dioxide, ammonia, glycerol, methanol, ethanol, propanol, butanol, acetone, acetic acid, formic acid, formamide (which may be derived from formic acid), and hydrogen peroxide.

In some embodiments, step (b) is conducted at a first absolute pressure selected from 0.05 mbar (mbar=millibar) to 5 bar. The first absolute pressure may be about, at least about, or at most about 0.1 mbar, 1 mbar, 10 mbar, 100 mbar, 500 mbar, 1 bar, 1.5 bar, 2 bar, 2.5 bar, 3 bar, 3.5 bar, 4 bar, 4.5 bar, or 5 bar. In this disclosure, the unit of "bar" is equivalent to "bara" which is absolute pressure, rather than gauge pressure.

In some embodiments, step (c) is conducted at a second absolute pressure that is the same, or about the same, as the first absolute pressure. Alternatively, step (c) may be conducted at a second absolute pressure that is higher than the first absolute pressure. In certain embodiments, step (c) is conducted at a second absolute pressure that is lower than the first absolute pressure.

The liquid solution is at a liquid initial temperature prior to exposing the intermediate biomass material to the liquid solution. This liquid initial temperature may generally be selected from 20° C. to 210° C., such as about, at least about, or at most about 25° C., 30° C., 40° C., 50° C., 60° C., 70° C., 80° C., 90° C., 100° C., 110° C., 120° C., 130° C., 140° C., 150° C., 160° C., 170° C., 180° C., 190° C., or 200° C.

In some embodiments, the liquid initial temperature is selected such that the liquid initial temperature is from about 5° C. to about 20° C. less than the condensation temperature of the condensable vapor calculated at the second absolute pressure in step (c). In various embodiments, the liquid initial temperature is about, at least about, or at most about 1° C., 2° C., 3° C., 4° C., 5° C., 6° C., 7° C., 8° C., 9° C., 10° C., 11° C., 12° C., 13° C., 14° C., 15° C., 16° C., 17° C., 18° C., 19° C., 20° C., 21° C., 22° C., 23° C., 24° C., or 25° C. less than the condensation temperature of the condensable vapor calculated at the second absolute pressure in step (c).

In certain embodiments, a multicomponent condensable vapor has multiple condensation temperatures in which case the liquid initial temperature is selected such that it is from about 5° C. to about 20° C. less than the lowest condensation temperature of the condensable vapor calculated at the second absolute pressure in step (c), to avoid fractional condensation.

In some embodiments, during step (b), at least 50 vol % of the non-condensable gases are removed out of the biomass pores. The volume fraction of non-condensable gases removed out of the biomass pores may be about, or at least about, 40 vol %, 50 vol %, 60 vol %, 70 vol %, 75 vol %, 80 vol %, 90 vol %, or 95 vol %, for example.

In some embodiments, during step (c), at least 50 vol % of the condensable vapor that is contained within the biomass pores condenses. The volume fraction of condensable vapor that condenses may be about, or at least about, 50 vol %, 60 vol %, 70 vol %, 75 vol %, 80 vol %, 90 vol %, 95 vol %, or 99 vol %, for example.

Typically, the composition of the reaction solution is specified for a given downstream process (e.g., pretreatment and hydrolysis) as described in detail in this specification.

The quantities of condensable vapor(s), liquid solution(s), and pretreatment chemical(s) will be added to the process in order to achieve the desired composition of the reaction solution, taking into account the starting moisture level of the biomass feedstock.

Steps (b) and (c) may be carried out in a common unit or in separate units. In certain embodiments, step (b) is conducted in a first unit and step (c) is conducted in both the first unit and a second unit. In certain embodiments, step (b) is conducted in both a first unit and a second unit, and step (c) is conducted in only the second unit.

During step (b), the condensable vapor may flow countercurrently, cross-currently, or cocurrently relative to a flow of the biomass feedstock. In preferred embodiments, the condensable vapor flows countercurrently or cross-currently relative to a flow of the biomass feedstock.

Process step (d) may include pretreatment and/or hydrolysis of the impregnated biomass material within a digestor, to form biomass sugars. The biomass sugars may be recovered as a sugar product and/or fermented to at least one fermentation product, which is preferably purified.

In some embodiments employing pretreatment and/or hydrolysis, the process includes mechanical refining of the impregnated biomass material during or after pretreatment and/or hydrolysis.

Process step (d) may include pretreatment and/or hydrolysis of the impregnated biomass material within a digestor, to form a nanocellulose precursor pulp. The process may further comprise mechanically treating the nanocellulose precursor pulp to generate cellulose nanofibrils and/or cellulose nanocrystals. Exemplary processes and apparatus to convert nanocellulose precursor pulp into cellulose nanofibrils and/or cellulose nanocrystals are described in commonly owned U.S. Pat. No. 9,187,865, issued on Nov. 17, 2015 and U.S. Patent App. Pub. No. 2018/0298113 A1, published on Oct. 18, 2018, which are each hereby incorporated by reference herein.

In some embodiments, the process does not include forming a conventional pulp material for making paper or paper-based products. That is, step (d) may involve converting pretreated material into sugars, fermentation products, lignin, nanocellulose, or combinations thereof, and not using the pretreated material as pulp for papermaking or other conventional pulp and paper processes.

Generally, the process may be continuous, semi-continuous, batch, or semi-batch. Preferably, the process is a continuous process.

Within the process, any vessel may be a static vessel or an agitated vessel. Any vessel may be configured in a horizontal, vertical, or slanted orientation.

Other variations of the invention utilize a process for impregnating a biomass feedstock with a reaction solution, the process comprising:
(a) providing a biomass feedstock that contains non-condensable gases within biomass pores of the biomass feedstock;
(b) introducing a condensable vapor comprising a pretreatment chemical into the biomass pores to remove at least some of the non-condensable gases out of the biomass pores, thereby generating an intermediate biomass material, wherein at least a portion of the condensable vapor as well as at least a portion of the pretreatment chemical remains within the biomass pores;
(c) exposing the intermediate biomass material to a liquid solution to (i) infiltrate the liquid solution into the biomass pores and (ii) condense at least a portion of the condensable vapor to form a condensed liquid contained within the biomass pores, thereby generating an impregnated biomass material containing a reaction solution comprising the liquid solution and the condensed liquid, wherein the reaction solution includes the pretreatment chemical; and
(d) recovering or further processing the impregnated biomass material, wherein the pretreatment chemical is optionally sulfur dioxide or a derivative thereof.

Note that in embodiments in which the pretreatment chemical is sulfur dioxide, the sulfur dioxide may be considered to be a condensable vapor rather than a non-condensable gas, even though the condensation point of $SO_2$ at 1 bar is −10° C. The reason that $SO_2$ is may be considered to be condensable is because it is a relatively polar compound, and so readily dissolves in water to form sulfurous acid ($H_2SO_3$) at low pH. On the other hand, when excess $SO_2$ is present—relative to the equilibrium amount as a function of pH and temperature—there will be a non-condensable portion of sulfur dioxide.

Other variations of the invention utilize a process for impregnating a biomass feedstock with a reaction solution, the process comprising:
(a) providing a biomass feedstock that contains non-condensable gases within biomass pores of the biomass feedstock;
(b) introducing a condensable first vapor into the biomass pores to remove at least some of the non-condensable gases out of the biomass pores, thereby generating an intermediate biomass material, wherein at least a portion of the condensable first vapor remains within the biomass pores;
(c) introducing a second vapor comprising a pretreatment chemical into the biomass pores;
(d) exposing the intermediate biomass material to a liquid solution to (i) infiltrate the liquid solution into the biomass pores, (ii) condense at least a portion of the condensable vapor within the biomass pores, and (iii) condense or dissolve at least a portion of the pretreatment chemical within the biomass pores, thereby generating an impregnated biomass material containing a reaction solution comprising the liquid solution and the condensed liquid, wherein the reaction solution includes the pretreatment chemical; and
(e) recovering or further processing the impregnated biomass material, wherein step (d) is conducted sequentially after step (c) and/or simultaneously with step (c), and wherein the pretreatment chemical is optionally sulfur dioxide or a derivative thereof.

Other variations of the invention utilize a process for impregnating a biomass feedstock with a reaction solution, the process comprising:
(a) providing a biomass feedstock that contains non-condensable gases within biomass pores of the biomass feedstock;
(b) introducing a condensable vapor into the biomass pores to remove at least some of the non-condensable gases out of the biomass pores, thereby generating an intermediate biomass material, wherein at least a portion of the condensable vapor remains within the biomass pores, and wherein the condensable vapor optionally includes at least one pretreatment chemical;
(c) indirectly cooling the intermediate biomass material to condense at least a portion of the condensable vapor to form a condensed liquid contained within the biomass pores, thereby generating an impregnated biomass material containing a reaction solution comprising at least one pretreatment chemical; and (d) recovering or further processing the impregnated biomass material, wherein at least one pretreatment chemical is optionally sulfur dioxide or a derivative thereof.

Some variations of the invention utilize a system for impregnating a biomass feedstock with a reaction solution, the system comprising:

(a) an input for a biomass feedstock that contains non-condensable gases within biomass pores of the biomass feedstock;

(b) a first impregnation stage configured to introduce a condensable vapor into the biomass pores to remove at least some of the non-condensable gases out of the biomass pores, thereby generating an intermediate biomass material, wherein at least a portion of the condensable vapor remains within the biomass pores;

(c) a second impregnation stage configured to expose the intermediate biomass material to a liquid solution to (i) infiltrate the liquid solution into the biomass pores and (ii) condense at least a portion of the condensable vapor to form a condensed liquid contained within the biomass pores, thereby generating an impregnated biomass material containing a reaction solution comprising the liquid solution and the condensed liquid, In this system, the first impregnation stage and the second impregnation stage may be in a common unit or in separate units. A unit may be a tank, a reactor, a column, a pipe, or any other vessel that is suitable for carrying out the process.

Other variations of the invention utilize a system for impregnating a biomass feedstock with a reaction solution, the system comprising:

(a) an input for a biomass feedstock that contains non-condensable gases within biomass pores of the biomass feedstock;

(b) a first impregnation stage configured to introduce a condensable vapor into the biomass pores to remove at least some of the non-condensable gases out of the biomass pores, thereby generating an intermediate biomass material, wherein at least a portion of the condensable vapor remains within the biomass pores;

(c) a second impregnation stage configured to introduce a second vapor comprising a pretreatment chemical into said biomass pores;

(d) a third impregnation stage configured to expose the intermediate biomass material to a liquid solution to (i) infiltrate the liquid solution into the biomass pores, (ii) condense at least a portion of the condensable vapor to form a condensed liquid contained within the biomass pores, and (iii) condense or dissolve at least a portion of the pretreatment chemical within the biomass pores, thereby generating an impregnated biomass material containing a reaction solution comprising the liquid solution and the condensed liquid, wherein the reaction solution includes the pretreatment chemical; wherein the first impregnation stage, the second impregnation stage, and the third impregnation stage are in a common unit, in two separate units, or in three separate units.

Some variations produce a composition comprising an impregnated biomass material, the composition produced by a process comprising:

(a) providing a biomass feedstock that contains non-condensable gases within biomass pores of the biomass feedstock;

(b) introducing a condensable vapor into the biomass pores to remove at least some of the non-condensable gases out of the biomass pores, thereby generating an intermediate biomass material, wherein at least a portion of the condensable vapor remains within the biomass pores;

(c) exposing the intermediate biomass material to a liquid solution to (i) infiltrate the liquid solution into the biomass pores and (ii) condense at least a portion of the condensable vapor to form a condensed liquid contained within the biomass pores, thereby generating an impregnated biomass material containing a reaction solution comprising the liquid solution and the condensed liquid; and (d) recovering or further processing the impregnated biomass material.

In some embodiments, the lignocellulosic biomass feedstock is selected from the group consisting of hardwoods, softwoods, sugarcane bagasse, sugarcane straw, energy cane, corn stover, corn cobs, corn fiber, and combinations thereof.

The biomass feedstock may be selected from hardwoods, softwoods, forest residues, agricultural residues (such as sugarcane bagasse), industrial wastes, consumer wastes, or combinations thereof. In any of these processes, the feedstock may include sucrose. In some embodiments with sucrose present in the feedstock (e.g., energy cane, sugarcane, or sugar beets), some of the sucrose is recovered as part of the fermentable sugars. In some embodiments with dextrose (or starch that is readily hydrolyzed to dextrose) present in the feedstock (e.g., corn), some of the dextrose is recovered as part of the fermentable sugars.

Some embodiments of the invention enable processing of agricultural residues, which for present purposes is meant to include lignocellulosic biomass associated with food crops, annual grasses, energy crops, or other annually renewable feedstocks. Exemplary agricultural residues include, but are not limited to, corn stover, corn fiber, wheat straw, sugarcane bagasse, rice straw, oat straw, barley straw, miscanthus, energy cane, or combinations thereof.

Certain exemplary embodiments of the invention will now be described. These embodiments are not intended to limit the scope of the invention as claimed. The order of steps may be varied, some steps may be omitted, and/or other steps may be added. Reference herein to first step, second step, etc. is for illustration purposes only. Similarly, unit operations may be configured in different sequences, some units may be omitted, and other units may be added.

In some embodiments, in a first impregnation stage, a condensable vapor (such as steam) is used to remove at least a portion of non-condensable gases (such as air) from pores of a biomass feedstock. The removed non-condensable gases exit the first impregnation stage in a gas purge. In a second impregnation stage, a liquid solution (such as water with sulfuric acid) contacts the biomass feedstock that is depleted of non-condensable gases and that contains condensable vapor in biomass pores. The liquid solution is at an initial temperature that is lower than the condensation temperature of the condensable vapor, resulting in at least partial if not complete condensation of the condensable vapor. The mixture of liquid solution and condensed vapor forms a reaction solution within the biomass material, which may be referred to as impregnated biomass material. The impregnated biomass material is then optionally utilized in downstream processes, such as (but not limited to) pretreatment, solid/liquid separation, hydrolysis, fermentation, purification, or nanocellulose generation (e.g., production of cellulose nanofibrils and/or cellulose nanocrystals).

In some embodiments, in a first impregnation stage, a condensable vapor with a pretreatment chemical (such as steam with ethanol and/or sulfur dioxide) is used to remove at least a portion of non-condensable gases (such as air) from pores of a biomass feedstock. The removed non-condensable gases exit the first impregnation stage in a gas purge. In a second impregnation stage, a liquid solution (such as water and/or ethanol) contacts the biomass feedstock that is depleted of non-condensable gases and that contains condensable vapor in biomass pores. The liquid solution is at an initial temperature that is lower than the condensation temperature of the condensable vapor, resulting in at least partial if not complete condensation of the condensable vapor. The mixture of liquid solution and condensed vapor forms a reaction solution (such as water, ethanol, and sulfur dioxide) within the biomass material. The impregnated biomass material is then optionally utilized in downstream processes, such as (but not limited to) pretreatment, solid/liquid separation, hydrolysis, fermentation, purification, or nanocellulose generation (e.g., production of cellulose nanofibrils and/or cellulose nanocrystals).

In some embodiments, in a first impregnation stage, a condensable vapor (such as steam) is used to remove at least a portion of non-condensable gases (such as air) from pores of a biomass feedstock. The removed non-condensable gases exit the first impregnation stage in a gas purge. In a second impregnation stage, an additional vapor with a pretreatment chemical (such as steam with sulfur dioxide, or sulfur dioxide alone) is added to the biomass feedstock that is depleted of non-condensable gases and that contains condensable vapor in biomass pores. The additional vapor may displace an additional quantity of non-condensable gases (i.e., non-condensable gases that were not removed in the first impregnation stage). The additional vapor mixes with the condensable vapor within the biomass pores, and depending on the temperature of the additional vapor, there may be some condensation of the condensable vapor in the second impregnation stage. In a third impregnation stage, a liquid solution (such as water or a water/ethanol mixture) contacts the biomass feedstock that is depleted of non-condensable gases and that contains condensable vapor and additional vapor in biomass pores. The liquid solution is at an initial temperature that is lower than at least one condensation temperature of mixture of condensable vapor and additional vapor, resulting in at least partial if not complete condensation of the mixture of condensable vapor and additional vapor. The mixture of liquid solution, condensed vapor, and condensed (or dissolved) additional vapor forms a reaction solution within the biomass material. The impregnated biomass material is then optionally utilized in downstream processes, such as (but not limited to) pretreatment, solid/liquid separation, hydrolysis, fermentation, purification, or nanocellulose generation (e.g., production of cellulose nanofibrils and/or cellulose nanocrystals).

In some embodiments, in a first impregnation stage, a condensable vapor (such as ethanol vapor) is used to remove at least a portion of non-condensable gases (such as carbon dioxide) from pores of a biomass feedstock. The removed non-condensable gases exit the first impregnation stage in a gas purge. In a second impregnation stage, a liquid solution (such as water) contacts the biomass feedstock that is depleted of non-condensable gases and that contains condensable vapor in biomass pores. The liquid solution is at an initial temperature that is lower than the condensation temperature of the condensable vapor, resulting in at least partial if not complete condensation of the condensable vapor. In a third impregnation stage, an additional vapor with a pretreatment chemical (such as sulfur dioxide) is added to the biomass feedstock that is depleted of non-condensable gases and that contains condensed vapor in biomass pores. Depending on the temperature of the additional vapor, there may be some condensation or vaporization of the solution contained in the biomass pores. The mixture of liquid solution, condensed vapor, and condensed (or dissolved) additional vapor forms a reaction solution within the biomass material. The impregnated biomass material is then optionally utilized in downstream processes, such as (but not limited to) pretreatment, solid/liquid separation, hydrolysis, fermentation, purification, or nanocellulose generation (e.g., production of cellulose nanofibrils and/or cellulose nanocrystals).

In some embodiments, in a first impregnation stage, a condensable vapor (such as steam and ethanol vapor) is used to remove at least a portion of non-condensable gases (such as air) from pores of a biomass feedstock. The removed non-condensable gases exit the first impregnation stage in a gas purge. Then, indirect cooling (no injection of cool liquid) is utilized to cause condensation of at least a portion of the condensable vapor in biomass pores. The condensed vapor forms a reaction solution within the biomass material. The impregnated biomass material is then optionally utilized in downstream processes, such as (but not limited to) pretreatment, solid/liquid separation, hydrolysis, fermentation, purification, or nanocellulose generation (e.g., production of cellulose nanofibrils and/or cellulose nanocrystals).

Much of the discussion that follows is in reference to the process step(s) of further processing the impregnated biomass material. As will be readily recognized, a number of individual steps may be utilized to carry out treatment of the impregnated biomass material by chemical, mechanical, thermal, electrochemical, or other means, to generate products and potential co-products. In an integrated and continuous biorefinery, the impregnated biomass material will typically be converted immediately (i.e., without intermediate storage) to products. However, that is not necessarily the case. Impregnated biomass material may be stored for a period of time before further processing. Additives may be introduced to the impregnated biomass material before further processing. The impregnated biomass material may be conveyed to an adjacent site or even transported to another site for processing.

All references here in "impregnated biomass material", "impregnated biomass", "impregnated biomass feedstock" and the like are in reference to various embodiments of this disclosure, in which a starting biomass feedstock is combined with a reaction solution, or with a recovered vapor, according to the principles of the invention. Stated another way, for convenience, the above process descriptions to generate impregnated biomass material are not repeated in all the embodiments described below, but it will be understood that the principles of the invention may be utilized to produce the impregnated biomass material to be processed.

Some variations utilize a process to produce a fermentation product (e.g., ethanol) from lignocellulosic biomass, the process comprising:
 (a) introducing an impregnated biomass material to a single-stage digestor, wherein the impregnated biomass material includes (i) a feedstock containing cellulose, hemicellulose, and lignin and (ii) a reaction solution;
 (b) exposing the biomass material to the impregnated reaction solution comprising steam or liquid hot water within the digestor, to solubilize at least a portion of the hemicellulose in a liquid phase and to provide a cellulose-rich solid phase;

(c) refining the cellulose-rich solid phase, together with the liquid phase, in a mechanical refiner to reduce average particle size of the cellulose-rich solid phase, thereby providing a mixture comprising refined cellulose-rich solids and the liquid phase;

(d) enzymatically hydrolyzing the mixture in a hydrolysis reactor with cellulase enzymes, to generate fermentable sugars from the mixture, wherein the hydrolysis reactor includes one or more hydrolysis stages; and (e) fermenting at least some of the fermentable sugars in a fermentor to produce a fermentation product.

A lignocellulosic biomass feedstock may be pretreated, prior to step (a), using one or more techniques selected from the group consisting of cleaning, washing, drying, milling, particle size-classifying, and combinations thereof. The process may include cleaning the starting feedstock by wet or dry cleaning. The process may include size reduction, hot-water soaking, dewatering, steaming, or other operations, upstream of the digestor.

The impregnated biomass material may be treated, prior to step (a) or during step (a), using one or more techniques selected from the group consisting of cleaning, washing, drying, milling or other mechanical treatment, and combinations thereof.

Step (b) may utilize a digestor residence time from about 2 minutes to about 4 hours. In some embodiments, the digestor residence time is about 10 minutes or less. In various embodiments, the digestor residence time is about 15, 20, 25, 30, 35, 40, 45, 50, 55 minutes, or about 1.0, 1.5, 2.0, 2.5, 3.0, 3.5, or 4.0 hours, including any intervening ranges.

Step (b) may utilize a digestor temperature from about 100° C. to about 220° C., such as from about 160° C. to about 190° C. In various embodiments, the digestor temperature is about 110° C., 120° C., 130° C., 140° C., 150° C., 160° C., 170° C., 180° C., 190° C., 200° C., or 210° C., including any intervening ranges. At a given reaction severity, there is a trade-off between time and temperature. Optionally, a temperature profile (in time and/or in space) is specified for the digestor.

It is noted that the digestor temperature may be measured in a variety of ways. The digestor temperature may be taken as the vapor temperature within the digestor. The digestor temperature may be measured from the temperature of the solids and/or the liquids (or a reacting mixture thereof). The digestor temperature may be taken as the digestor inlet temperature, the digestor outlet temperature, or a combination or correlation thereof. The digestor temperature may be measured as, or correlated with, the digestor wall temperature. Note that especially at short residence times (e.g., 5 minutes), the temperatures of different phases present (e.g., vapor, liquid, solid, and metal walls) may not reach equilibrium.

Step (b) may utilize a digestor pressure from atmospheric pressure up to about 40 bar, such as from about 10 bar to about 20 bar. The digestor pressure may correspond to the steam saturation pressure at the digestor temperature. In some embodiments, the digestor pressure is higher than the steam saturation pressure at the digestor temperature, such as when supersaturated water vapor is desired, or when an inert gas is also present in the digestor. In some embodiments, the digestor pressure is lower than the steam saturation pressure at the digestor temperature, such as when superheated steam is desired, or when a digestor vapor bleed line is present.

Step (b) may be conducted at a digestor liquid-solid weight ratio from about 0.1 to about 10, such as from about 1 to about 10, preferably about 2 or less. In various embodiments, the digestor liquid-solid weight ratio is about 1, 1.1, 1.2, 1.3, 1.4, 1.5, 1.6, 1.7, 1.8, 1.9, 2, 2.5, 3, 4, 5, 6, 7, 8, including any intervening ranges.

Step (b) may be conducted at a digestor pH from about 0.5 to about 6, such as from about 3 to 5, or from about 3.5 to about 4.5. In various embodiments, the digestor pH is about 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0, including any intervening ranges. Generally, a lower pH gives a higher reaction severity. Typically, the digestor pH is not controlled but is dictated by the composition of the starting feedstock (e.g., acid content or buffer capacity) and whether an acid is included in the aqueous reaction solution. Based on measurements made to the starting material or dynamic measurements made or correlated during the process, an additive (e.g., an acid or base) may be added to the digestor to vary the digestor pH.

In some embodiments of the process, a blow tank is configured for receiving the cellulose-rich solid phase or the refined cellulose-rich solids at a pressure lower than the digestor pressure. The blow tank may be disposed downstream of the digestor and upstream of the mechanical refiner, i.e. between the digestor and refiner. Or the blow tank may be disposed downstream of the mechanical refiner. In certain embodiments, a first blow tank is disposed upstream of the mechanical refiner and a second blow tank is disposed downstream of the mechanical refiner. Optionally, vapor is separated from the blow tank(s), or from a vapor-separation unit described earlier in this specification. The vapor may be purged and/or condensed or compressed and returned to the digestor. In either case, heat may be recovered from at least some of the vapor.

The mechanical refiner (if employed) may be selected from the group consisting of a hot-blow refiner, a hot-stock refiner, a blow-line refiner, a disk refiner, a conical refiner, a cylindrical refiner, an in-line defibrator, an extruder, a homogenizer, and combinations thereof.

The mechanical refiner may be operated at a refining pressure selected from about 1 bar to about 20 bar. In some embodiments, the refining pressure is about 3 bar or less. In some embodiment, the mechanical refiner is operated at or about at atmospheric pressure.

The mechanical refiner may operate at an electrical load from about 2 kW/ton to about 200 kW/ton, such as from about 30 kW/ton to about 120 kW/ton, units of refining power per ton of the cellulose-rich solid phase. In various embodiments, the mechanical refiner operates at an electrical load of about 2, 5, 10, 20, 30, 40, 50, 60, 70, 80, 90, 100, 110, 120, 130, 140, 150, 160, 170, 180, 190, or 200 kW/ton, including any intervening ranges.

The mechanical refiner may transfer from about 50 kW·hr/ton to about 200 kW·hrton, units of refining energy per ton of the cellulose-rich solid phase. In various embodiments, the mechanical refiner transfers about 10, 20, 30, 40, 50, 60, 70, 80, 90, 100, 110, 120, 130, 140, 150, 160, 170, 180, 190, 200, 225, 250, 275, 300, 325, 350, or 400 kW·hr/ton, including any intervening ranges.

The mechanical refiner may be designed and operating using principles that are well-known in the art of pulp and paper plants and biorefineries. For example, refiner plate gap dimensions may be varied, such as from about 0.1 mm to about 10 mm, or about 0.5 mm to about 2 mm, to reach the desired particle-size distribution. The choice of gap dimensions may depend on the nature of the starting feedstock, for example. Pretreated material derived from some biomass feedstocks is relatively easy to refine, such that the refining severity need not be high, or gap dimensions need not be very small. Indeed, pretreated material derived from certain biomass feedstocks and certain process conditions does not require mechanical refining at all.

In some embodiments, the mechanical refiner is designed and/or adjusted to achieve certain average fiber lengths, such as about 1 mm, 0.9 mm, 0.8 mm, 0.7 mm, 0.6 mm, 0.5 mm, 0.4 mm, 0.3 mm, 0.2 mm, 0.1 mm or less. Generally speaking, shorter fibers or fibers with lower diameter are easier to enzymatically hydrolyze to sugars, compared to larger fibers.

In some embodiments, the mechanical refiner is designed and/or adjusted to achieve a certain shives (bundles of fibers) content, such as less than about 5%, 4%, 3%, 2%, 1%, 0.5%, or less. Shives are not desirable because they tend to be more difficult to enzymatically hydrolyze to sugars. Knots and other large particles should be refined as well.

The process may utilize multiple mechanical refiners at different parts of the process. For example, between steps (c) and (d), at least a portion of the mixture may be conveyed to a second mechanical refiner, typically operated at the same or a lower refining pressure compared to that of the mechanical refiner in step (c). In certain embodiments, the first mechanical refiner in step (c) is a pressurized refiner and the second mechanical refiner is an atmospheric refiner.

In some embodiments, step (d) utilizes multiple enzymatic-hydrolysis reactors. For example, step (d) may utilize single-stage enzymatic hydrolysis configured for cellulose liquefaction and saccharification, wherein the single-stage enzymatic hydrolysis includes one or more tanks or vessels. Step (d) may utilize multiple-stage enzymatic hydrolysis configured for cellulose liquefaction followed by saccharification, wherein each stage includes one or more tanks or vessels. When multiple-stage enzymatic hydrolysis is employed, the process may include additional mechanical refining of the mixture, or a partially hydrolyzed form thereof, following at least a first stage of enzymatic hydrolysis.

In some embodiments, non-acid and non-enzyme catalysts may be employed for co-hydrolyzing glucose oligomers and hemicellulose oligomers. For example, base catalysts, solid catalysts, catalytic ionic liquids, or other effective catalysts may be employed.

The process utilized in some embodiments further includes:
 introducing the mixture to a first enzymatic-hydrolysis reactor under effective hydrolysis conditions to produce a liquid hydrolysate comprising sugars from the refined cellulose-rich solids and optionally from the hemicellulose, and a residual cellulose-rich solid phase;
 optionally separating at least some of the liquid hydrolysate from the residual cellulose-rich solid phase;
 conveying the residual cellulose-rich solid phase through an additional mechanical refiner and/or recycling the residual cellulose-rich solid phase through the mechanical refiner, to generate refined residual cellulose-rich solids; and
 introducing the refined residual cellulose-rich solids to a second enzymatic-hydrolysis reactor under effective hydrolysis conditions, to produce additional sugars.

In some embodiments, a self-cleaning filter is configured downstream of the hydrolysis reactor to remove cellulosic fiber strands. The cellulosic fiber strands may be recycled, at least in part, back to the hydrolysis reactor.

Cellulase enzymes may be introduced directly to the mechanical refiner, so that simultaneous refining and hydrolysis occurs. Alternatively, or additionally, cellulase enzymes may be introduced to the cellulose-rich solid phase prior to step (c), so that during step (c), simultaneous refining and hydrolysis occurs. In these embodiments, the mechanical refiner is preferably operated at a maximum temperature of 75° C., 70° C., 65° C., 60° C., 55° C., 50° C. or less to maintain effective hydrolysis conditions.

The process may include conversion of hemicellulose to a fermentation product, in various ways. For example, step (d) may include enzymatic hydrolysis of hemicellulose oligomers to generate fermentable monomer sugars. Step (e) may include enzymatic hydrolysis of hemicellulose oligomers to generate fermentable monomer sugars within the fermentor. The monomer sugars, derived from hemicellulose, may be co-fermented along with glucose or may be fermented in a second fermentor operated in series or parallel with the primary fermentor.

The process may further comprise removal of one or more fermentation inhibitors, such as by steam stripping. In some embodiments, acetic acid (a fermentation inhibitor) is removed and optionally recycled to the digestor.

The process typically includes concentrating the fermentation product by distillation. The distillation generates a distillation bottoms stream, and in some embodiments the distillation bottoms stream is evaporated in a distillation bottoms evaporator that is a mechanical vapor compression evaporator or is integrated in a multiple-effect evaporator train.

The fermentation product may be selected from the group consisting of ethanol, isopropanol, acetone, n-butanol, isobutanol, 1,4-butanediol, succinic acid, lactic acid, and combinations thereof. In certain embodiments, the fermentation product is ethanol (and $CO_2$ necessarily co-produced in fermentation).

The solid yield (also known as pulp yield or fiber yield) is the fraction of solids remaining (not dissolved) following digestion and refining, but prior to enzymatic hydrolysis, relative to the starting biomass feedstock. The solid yield of the process may vary, such as from about 60% to about 97%, typically from about 70% to about 80%. The solid yield does not include dissolved solids (e.g., hemicellulose sugars in solution). In various embodiments, the solid yield is about 70%, 75%, 80%, 85%, 90%, or 95%, including any intervening ranges.

The sugar yield (also known as carbohydrate yield) is the fraction of sugar monomers and oligomers following enzymatic hydrolysis, but prior to fermentation of the hydrolysate, relative to the solid material entering hydrolysis from digestion and any refining. The sugar yield of the process may vary, such as from about 40% to about 80% (or more), preferably at least 50%. In various embodiments, the sugar yield is about 50%, 52%, 54%, 56%, 58%, 60%, 62%, 64%, 66%, 68%, 70%, or more, including any intervening ranges.

The fraction of starting hemicellulose that is extracted into solution may be from about 10% to about 95%, such as about 15%, 20%, 25%, 30%, 35%, 40%, 45%, 50%, 55%, 60%, 65%, 70%, 75%, 80%, 85%, or 90%, including any intervening ranges.

The fermentation product yield (e.g., ethanol yield) is the yield of final product produced in fermentation, relative to the theoretical yield if all sugars are fermented to the product. The theoretical fermentation yield accounts for any necessary co-products, such as carbon dioxide in the case of ethanol. In the specific case of ethanol, the ethanol yield of the process may vary, such as from about 65% to about 95%, typically at least 80%. In various embodiments, the ethanol yield is about 75%, 76%, 77%, 78%, 79%, 80%, 81%, 82%, 83%, 84%, 85%, 86%, 87%, 88%, 89%, 90%, or more, including any intervening ranges. An ethanol yield on the basis of starting feedstock can also be calculated. In various embodiments, the ethanol yield is from about 150 to about 420 liters per bone-dry metric tons of starting biomass feedstock, typically at least about 200, 210, 220, 230, 240, 250, 260, 270, 280, 290, or 300 liters ethanol per metric bone-dry metric tons of starting biomass feedstock.

Other variations of the invention utilize a process to produce a fermentation product from lignocellulosic biomass, the process comprising:
(a) introducing an impregnated biomass material to a single-stage or multiple-stage digestor, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor, to solubilize at least a portion of the hemicellulose in a liquid phase and to provide a cellulose-rich solid phase;
(c) separating at least a portion of the liquid phase from the cellulose-rich solid phase;
(d) mechanically refining the cellulose-rich solid phase to reduce average particle size, thereby providing refined cellulose-rich solids;
(e) enzymatically hydrolyzing the refined cellulose-rich solids in a hydrolysis reactor with cellulase enzymes, to generate fermentable sugars;
(f) hydrolyzing the hemicellulose in the liquid phase, separately from step (e), to generate fermentable hemicellulose sugars; and
(g) fermenting at least some of the fermentable sugars, and optionally at least some of the fermentable hemicellulose sugars, in a fermentor to produce a fermentation product.

Still other variations of the invention utilize a process to produce a fermentation product from lignocellulosic biomass, the process comprising:
(a) introducing an impregnated biomass material to a single-stage digestor, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor, to solubilize at least a portion of the hemicellulose in a liquid phase and to provide a cellulose-rich solid phase;
(c) mechanically refining the cellulose-rich solid phase to reduce average particle size, thereby providing refined cellulose-rich solids mixed with the liquid phase;
(d) separating at least a portion of the liquid phase from the refined cellulose-rich solids;
(e) enzymatically hydrolyzing the refined cellulose-rich solids in a hydrolysis reactor with cellulase enzymes, to generate fermentable sugars;
(f) hydrolyzing the hemicellulose in the liquid phase, separately from step (e), to generate fermentable hemicellulose sugars; and
(g) fermenting at least some of the fermentable sugars, and optionally at least some of the fermentable hemicellulose sugars, in a fermentor to produce a fermentation product.

Yet other variations of the invention utilize a process to produce fermentable sugars from lignocellulosic biomass, the process comprising:
(a) introducing an impregnated biomass material to a single-stage digestor, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor, to solubilize at least a portion of the hemicellulose in a liquid phase and to provide a cellulose-rich solid phase;
(c) mechanically refining the cellulose-rich solid phase, together with the liquid phase, to reduce average particle size of the cellulose-rich solid phase, thereby providing a mixture comprising refined cellulose-rich solids and the liquid phase;
(d) enzymatically hydrolyzing the mixture in a hydrolysis reactor with cellulase enzymes, to generate fermentable sugars from the mixture; and
(e) recovering or further treating the fermentable sugars.

In some variations, a process is utilized for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) conveying the digested stream through a mechanical refiner, thereby generating a refined stream with reduced average particle size of the cellulose-rich solids;
(d) separating a vapor from the refined stream;
(e) introducing the refined stream to an enzymatic hydrolysis unit under effective hydrolysis conditions to produce sugars from the cellulose-rich solids and optionally from the hemicellulose oligomers; and
(f) recovering or further processing at least some of the sugars as fermentable sugars.

Some variations utilize a process for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) conveying the digested stream through a mechanical refiner, thereby generating a refined stream with reduced average particle size of the cellulose-rich solids;
(d) separating a vapor from the refined stream;
(e) introducing the refined stream to an acid hydrolysis unit under effective hydrolysis conditions to produce sugars from the cellulose-rich solids and optionally from the hemicellulose oligomers;
(f) recovering or further processing at least some of the sugars as fermentable sugars.

Certain embodiments utilize a process for producing ethanol from cellulosic biomass, the process comprising:
- (a) generating an impregnated biomass material, wherein the impregnated biomass material includes (i) a feedstock containing cellulose, hemicellulose, and lignin and (ii) a reaction solution;
- (b) exposing the biomass material to the impregnated reaction solution comprising steam or liquid hot water within the digestor under effective reaction conditions to produce a digested stream containing cellulose-rich solids, hemicellulose oligomers, and lignin;
- (c) conveying the digested stream through a blow-line refiner, thereby generating a refined stream with reduced average particle size of the cellulose-rich solids;
- (d) separating a vapor from the refined stream;
- (e) introducing the refined stream to an enzymatic hydrolysis unit under effective hydrolysis conditions to produce sugars from the cellulose-rich solids and from the hemicellulose oligomers;
- (f) fermenting the sugars to produce ethanol in dilute solution; and
- (g) concentrating the dilute solution to produce an ethanol product.

In some variations, a process for producing fermentable sugars from cellulosic biomass utilizes the following steps:
- (a) generating an impregnated biomass material, wherein the impregnated biomass material includes (i) a feedstock containing cellulose, hemicellulose, and lignin and (ii) a reaction solution;
- (b) exposing the biomass material to the impregnated reaction solution comprising steam or liquid hot water within the digestor under effective reaction conditions to produce a digested stream containing cellulose-rich solids, hemicellulose oligomers, and lignin;
- (c) reducing pressure of the digested stream;
- (d) introducing the digested stream to an enzymatic hydrolysis unit under effective hydrolysis conditions to produce a liquid phase comprising sugars from the cellulose-rich solids and optionally from the hemicellulose oligomers, and a solid phase comprising the cellulose-rich solids;
- (e) separating the liquid phase and the solid phase from step (d);
- (f) conveying the solid phase through a mechanical refiner, thereby generating a refined stream with reduced average particle size of the cellulose-rich solids;
- (g) recycling the refined stream to the enzymatic hydrolysis unit, to produce additional sugars from the cellulose-rich solids contained in the solid phase from step (d); and
- (h) recovering or further processing at least some of the sugars and at least some of the additional sugars as fermentable sugars.

Other variations utilize a process for producing fermentable sugars from cellulosic biomass, the process comprising:
- (a) generating an impregnated biomass material, wherein the impregnated biomass material includes (i) a feedstock containing cellulose, hemicellulose, and lignin and (ii) a reaction solution;
- (b) exposing the biomass material to the impregnated reaction solution comprising steam or liquid hot water within the digestor under effective reaction conditions to produce a digested stream containing cellulose-rich solids, hemicellulose oligomers, and lignin;
- (c) reducing pressure of the digested stream;
- (d) introducing the digested stream to a first enzymatic hydrolysis unit under effective hydrolysis conditions to produce a liquid phase comprising sugars from the cellulose-rich solids and optionally from the hemicellulose oligomers, and a solid phase comprising the cellulose-rich solids;
- (e) separating the liquid phase and the solid phase from step (d);
- (f) conveying the solid phase through a mechanical refiner, thereby generating a refined stream with reduced average particle size of the cellulose-rich solids;
- (g) recycling the refined stream to a second enzymatic hydrolysis unit, to produce additional sugars from the cellulose-rich solids contained in the solid phase from step (d); and
- (h) recovering or further processing at least some of the sugars and/or additional sugars (from the liquid phase from step (d)) as fermentable sugars.

Other variations utilize a process for producing a fermentation product from cellulosic biomass, the process comprising:
- (a) generating an impregnated biomass material, wherein the impregnated biomass material includes (i) a feedstock containing cellulose, hemicellulose, and lignin and (ii) a reaction solution;
- (b) exposing the biomass material to the impregnated reaction solution comprising steam or liquid hot water within the digestor under effective reaction conditions to produce a digested stream containing cellulose-rich solids, hemicellulose oligomers, and lignin;
- (c) optionally exploding the digested stream, thereby generating an exploded stream with reduced average particle size of the cellulose-rich solids;
- (d) introducing the digested stream and/or (if step (c) is conducted) the exploded stream to an enzymatic hydrolysis unit under effective hydrolysis conditions to produce a sugar-containing hydrolysate;
- (e) evaporating the hydrolysate using a multiple-effect evaporator or a mechanical vapor compression evaporator, to produce a concentrated hydrolysate;
- (f) fermenting the concentrated hydrolysate to produce a dilute fermentation product; and
- (g) concentrating the dilute fermentation product to produce a concentrated fermentation product.

Some variations utilize a process for producing fermentable sugars from cellulosic biomass, the process comprising:
- (a) generating an impregnated biomass material, wherein the impregnated biomass material includes (i) a feedstock containing cellulose, hemicellulose, and lignin and (ii) a reaction solution;
- (b) exposing the biomass material to the impregnated reaction solution comprising steam or liquid hot water within the digestor under effective reaction conditions to produce a digested stream containing cellulose-rich solids, hemicellulose oligomers, and lignin;
- (c) optionally conveying the digested stream through a mechanical refiner, thereby generating a refined stream with reduced average particle size of the cellulose-rich solids;
- (d) introducing the digested stream and/or (if step (c) is conducted) the refined stream to an enzymatic hydrolysis unit under effective hydrolysis conditions to produce a sugar-containing hydrolysate;
- (e) optionally evaporating the hydrolysate using a multiple-effect evaporator or a mechanical vapor compression evaporator, to produce a concentrated hydrolysate;

(f) fermenting the hydrolysate to produce a dilute fermentation product; and
(g) concentrating the dilute fermentation product to produce a concentrated fermentation product.

Other variations utilize a process for producing a fermentation product from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) optionally exploding the digested stream, thereby generating an exploded stream with reduced average particle size of the cellulose-rich solids;
(d) introducing the digested stream and/or (if step (c) is conducted) the exploded stream to an enzymatic hydrolysis unit under effective hydrolysis conditions to produce a sugar-containing hydrolysate;
(e) evaporating the hydrolysate using a multiple-effect evaporator or a mechanical vapor compression evaporator, to produce a concentrated hydrolysate;
(f) fermenting the concentrated hydrolysate to produce a dilute fermentation product; and
(g) concentrating the dilute fermentation product to produce a concentrated fermentation product.

Other variations utilize a process for producing a fermentation product from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) optionally conveying at least a portion of the digested stream through a first mechanical refiner in a blow line;
(d) optionally conveying at least a portion of the digested stream through a second mechanical refiner following pressure reduction of the digested stream;
(e) introducing the digested stream and/or (if step (c) and/or step (d) is conducted) a mechanically treated derivative thereof, to an enzymatic liquefaction unit under effective liquefaction conditions to produce a first intermediate stream;
(f) optionally conveying at least a portion of the first intermediate stream through a third mechanical refiner;
(g) introducing the first intermediate stream and/or (if step (f) is conducted) a mechanically treated derivative thereof, to a first enzymatic hydrolysis unit under effective hydrolysis conditions to produce a second intermediate stream;
(h) optionally conveying at least a portion of the second intermediate stream through a fourth mechanical refiner;
(i) introducing the second intermediate stream and/or (if step (h) is conducted) a mechanically treated derivative thereof, to a second enzymatic hydrolysis unit under effective hydrolysis conditions to produce a concentrated hydrolysate;
(j) fermenting the concentrated hydrolysate to produce a dilute fermentation product; and
(k) concentrating the dilute fermentation product to produce a concentrated fermentation product.

The process may include no refiner, or only the first mechanical refiner, or only the second mechanical refiner, or only the third mechanical refiner, or only the fourth mechanical refiner, or any combination thereof—e.g., any two of such refiners, or any three of such refiners, or all four of such refiners.

Some variations utilize a process for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) optionally conveying the digested stream through a mechanical refiner, thereby generating a refined stream with reduced average particle size of the cellulose-rich solids;
(d) introducing the digested stream and/or (if step (c) is conducted) the refined stream to an enzymatic hydrolysis unit under effective hydrolysis conditions to produce a sugar-containing hydrolysate;
(e) evaporating the hydrolysate using a multiple-effect evaporator or a mechanical vapor compression evaporator, to produce a concentrated hydrolysate;
(f) fermenting the concentrated hydrolysate to produce a dilute fermentation product; and
(g) concentrating the dilute fermentation product to produce a concentrated fermentation product.

Other variations of the invention utilize a process for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) conveying the digested stream through a mechanical refiner, thereby generating a refined stream with reduced average particle size of the cellulose-rich solids;
(d) introducing enzymes to the mechanical refiner and maintaining effective hydrolysis conditions to produce sugars from the cellulose-rich solids and optionally from the hemicellulose oligomers, simultaneously with step (c);
(e) evaporating water from the hydrolysate from step (d); and
(f) recovering or further processing at least some of the sugars as fermentable sugars.

Some variations utilize a process for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;

(b) exposing the biomass material to the impregnated reaction solution comprising steam or liquid hot water within the digestor under effective reaction conditions to produce a digested stream containing cellulose-rich solids, hemicellulose oligomers, and lignin;

(c) conveying the digested stream through a mechanical refiner, thereby generating a refined stream with reduced average particle size of the cellulose-rich solids;

(d) introducing the refined stream to an acid hydrolysis unit under effective hydrolysis conditions to produce sugars from the cellulose-rich solids and optionally from the hemicellulose oligomers;

(e) separating a vapor from the refined stream before, during, or after step (d); and (f) recovering or further processing at least some of the sugars as fermentable sugars.

In some embodiments, the reaction solution comprises or consists essentially of steam in saturated, superheated, or supersaturated form. In these or other embodiments, the reaction solution comprises or consists essentially of pressurized liquid hot water, for example water that is heated but under pressure (e.g., any pressure disclosed herein) such that the water is partially or completely in a liquid phase at equilibrium.

In certain embodiments, a combination of steam and liquid hot water is employed. For example, a pre-steaming step may be employed prior to the digestor, and then liquid hot water may be introduced to the digestor along with pre-steamed biomass. Depending on the temperature and pressure, the steam may partially or completely condense, or the liquid hot water may partially or completely enter the vapor phase, in the digestor head space and/or within open space between cellulose fibers, for example.

The reaction solution optionally includes an acid catalyst, to assist in extraction of hemicelluloses from the starting material, and possibly to catalyze some hydrolysis. In some embodiments, the acid is a sulfur-containing acid (e.g., sulfur dioxide). In some embodiments, the acid is acetic acid, which may be recovered from the digested stream (i.e., from downstream operations). Additives may be present in the reaction solution, such as acid or base catalysts, or other compounds present in recycled streams.

Many types of digestors are possible. The digestor may be horizontal, vertical, or inclined. The digestor may or may not have any internal agitator or means for agitation. The digestor may be fixed in place, or be allowed to rotate (e.g., about its axial or radial dimensions). The digestor may be operated in upflow or downflow mode, relative to the solids or the solid-liquid mixture. When there is excess liquid, the digestor may be operated either cocurrently or countercurrently (solid flow versus liquid flow). The digestor may be operated continuously, semi-continuously, in batch, or some combination or hybrid thereof. The flow pattern in the digestor may be plug flow, well-mixed, or any other flow pattern. The digestor may be heated internally or externally, such as by steam, hot oil, etc. Generally, the principles of chemical-reactor engineering may be applied to digestor design and operation.

In certain preferred embodiments of the invention, the digestor is a vertical digestor. In some embodiments, the digestor is not or does not include a horizontal digestor (e.g., Pandia-type vessel). Although the prior art tends to teach away from a vertical digestor for processing annual fibers (agricultural residues), a single-stage pretreatment in a vertical digestor works surprisingly well for steam or hot-water extraction of agricultural residues prior to enzymatic hydrolysis.

As intended herein, a "vertical digestor" can include non-vertical ancillary equipment, including feeding and discharge equipment. For example, a horizontal or inclined inlet (e.g., plug-screw feeder) or horizontal or inclined outlet (e.g., plug-screw discharger), a horizontal or inclined pre-impregnator, a horizontal or inclined blow line, and so on may be included in the process when a vertical digestor is utilized. Also, a vertical digestor may be substantially vertical but may contain sections or zones that are not strictly vertical, and may contain side-streams (inlet or outlet), internal recycle streams, and so on that may be construed as non-vertical. In some embodiments, a vertical digestor has a varying diameter along its length (height).

In certain embodiments of the invention, the digestor is a single-stage digestor. Here "single stage" means that biomass is extracted with an extraction solution (e.g., liquid hot water with an optional acid such as acetic acid) at reaction temperature and pressure, to solubilize hemicelluloses and lignin, with no intermediate separation prior to entering a mechanical refiner, blow line, or blow valve. The hemicelluloses are not separated and the cellulose-rich solids are not separately processed prior to enzymatic hydrolysis. Following the digestor and optional blow-line refiner, and after the pressure is released to reach atmospheric pressure, in some embodiments, the hemicelluloses may be washed from the solids and separately processed to hydrolyze hemicelluloses to monomers and/or to separately ferment hemicellulose sugars to ethanol.

In some embodiments, there is no intermediate separation: all extracted/digested contents-both the solid and liquid phases—are sent to enzymatic hydrolysis to produce glucose and other monomer sugars such as xylose. This configuration can be beneficial for process simplicity and lower costs.

In other embodiments, there is intermediate separation, i.e. solid/liquid separation of the solid and liquid phases from the digestor. Intermediate separation can be beneficial to enable separate processing and optimization of each stream. For example, the solid stream may be rich in cellulose and readily hydrolyzed using conventional cellulase enzymes. The liquid stream may be rich in hemicellulose and may be hydrolyzed using optimized hemicellulase enzymes. In such a scheme, the cellulose-derived sugars (e.g., glucose) may be fermented or converted to one product, while the hemicellulose-derived sugars (e.g., xylose, mannose, etc.) may be fermented or converted to another product. Simultaneous hydrolysis and fermentation may be applied to one stream but not the other, and so on, giving enhanced process flexibility.

Some specific embodiments of the invention utilize a single-stage vertical digestor configured to continuously pretreat incoming biomass with liquid hot water, followed by blow-line refining of the entire pretreated material, and then followed by enzymatic hydrolysis of the entire refined material.

The mechanical refiner may be selected from the group consisting of a hot-blow refiner, a hot-stock refiner, a blow-line refiner, a disk refiner, a conical refiner, a cylindrical refiner, an in-line defibrator, a homogenizer, and combinations thereof (noting that these industry terms are not mutually exclusive to each other). In certain embodiments, the mechanical refiner is a blow-line refiner. Other mechanical refiners may be employed, and chemical refining aids (e.g., fatty acids) may be introduced, such as to adjust viscosity, density, lubricity, etc.

Mechanically treating (refining) may employ one or more known techniques such as, but by no means limited to, milling, grinding, beating, sonicating, or any other means to reduce cellulose particle size. Such refiners are well-known in the industry and include, without limitation, Valley beaters, single disk refiners, double disk refiners, conical refiners, including both wide angle and narrow angle, cylindrical refiners, homogenizers, microfluidizers, and other similar milling or grinding apparatus. See, for example, Smook, *Handbook for Pulp & Paper Technologists*, Tappi Press, 1992.

A pressurized refiner may operate at the same pressure as the digestor, or at a different pressure. In some embodiments, both the digestor and the refiner operate in a pressure range corresponding to equilibrium steam saturation temperatures from about 170° C. to about 210° C., such as about 180° C. to about 200° C. Local hot spots may be present within the refiner, such as in regions of high-shear, high-friction contact between cellulose-rich solids and metal plates.

In some embodiments, a pressurized refiner is fed by a screw between the digestor and the refiner. In principle, the pressure in the refiner may be higher than the digestor pressure, due to mechanical energy input. For example, a high-pressure screw feeder may be utilized to increase refining pressure, if desired. Also, it will be recognized that localized pressures (force divided by area) may be higher than the vapor pressure, due to the presence of mechanical surface force (e.g., plates) impacting the solid material or slurry.

A blow tank may be situated downstream of the mechanical refiner, so that the mechanical refiner operates under pressure. The pressure of the mechanical refiner may be the same as the digestor pressure, or it may be different. In some embodiments, the mechanical refiner is operated at a refining pressure selected from about 2 bar ("bar" herein refers to gauge pressure unless otherwise noted) to about 20, such as about 3 bar to about 10 bar.

A blow tank may be situated upstream of the mechanical refiner, so that the mechanical refiner operates under reduced pressure or atmospheric pressure. In some embodiments, the mechanical refiner is operated a refining pressure of less than about 4 bar, less than about 2 bar, or at or about atmospheric pressure.

Note that "blow tank" should be broadly construed to include not only a tank but any other apparatus or equipment capable of allowing a pressure reduction in the process stream. Thus a blow tank may be a tank, vessel, section of pipe, valve, or other unit. In some embodiments, a blow tank is a vacuum cyclone separator. A blow tank may serve as one stage of a multi-stage vapor-separation unit, such as a multi-stage unit with three stages consisting of a blowback valve, followed by a particle-size separator, followed by a vacuum cyclone separator (blow tank).

In some embodiments, following a digestor to remove hemicellulose, an intermediate blow is performed to, for example, about 3 bar. The material is sent to a blow-line refiner, and then to a final blow to atmospheric pressure, for example. In some embodiments, a cold blow discharger is utilized to feed a pressurized refiner. In some embodiments, a transfer conveyor is utilized to feed a pressurized refiner.

The refining may be conducted at a wide range of solids concentrations (consistency), including from about 2% to about 50% consistency, such as about 4%, 6%, 8%, 10%, 15%, 20%, 30%, 35%, or 40% consistency.

A pressurized refiner may operate at the same pressure as the digestor, or at a different pressure. In some embodiments, both the digestor and the refiner operate in a pressure range corresponding to equilibrium steam saturation temperatures from about 170° C. to about 210° C., such as about 180° C. to about 200° C. In some embodiments, a pressurized refiner is fed by a screw between the digestor and the refiner.

In certain embodiments, a first blow tank is situated upstream of the mechanical refiner and a second blow tank is situated downstream of the mechanical refiner. In this scenario, the pressure is reduced somewhat between the digestor and the refiner, which operates above atmospheric pressure. Following the refining, the pressure is released in the second blow tank. In some embodiments, the mechanical refiner is operated at a refining pressure selected from about 1 bar to about 10 bar, such as about 2 bar to about 7 bar.

In some embodiments, the vapor is separated from a blow tank, and heat is recovered from at least some of the vapor. At least some of the vapor may be compressed and returned to the digestor. Some of the vapor may be purged from the process.

In some embodiments, heat is recovered from at least some of the vapor, using heat-integration principles described in detail above. At least some of the vapor may be compressed and returned to the digestor. Some of the vapor may be purged from the process.

In certain embodiments, the reduction of pressure that occurs across a blow valve causes, or assists, fiber expansion or fiber explosion. Fiber expansion or explosion is a type of physical action that can occur, reducing particle size or surface area of the cellulose phase, and enhancing the enzymatic digestibility of the pretreated cellulose. Certain embodiments employ a blow valve (or multiple blow valves) to replace a mechanical refiner or to augment the refining that results from a mechanical refiner, disposed either before or after such blow valve. Some embodiments combine a mechanical refiner and blow valve into a single apparatus that simultaneously refines the cellulose-rich solids while blowing the material to a reduced pressure.

In some embodiments, enzymes introduced or present in the enzymatic hydrolysis unit may include not only cellulases but also hemicellulases. In certain embodiments, enzymes introduced or present in the enzymatic hydrolysis unit include endoglucanases and exoglucanases.

Enzymatic hydrolysis may be conducted at a solid concentration from about 10 wt % to about 30 wt %, such as about 12 wt %, 15 wt %, 17 wt %, 20 wt %, 22 wt %, 25 wt %, or 28 wt %, for example.

Effective hydrolysis conditions may include a maximum temperature of 75° C. or less, preferably 65° C. or less. In some embodiments, the effective hydrolysis conditions include a hydrolysis temperature of about 30° C., 40° C., 45° C., 50° C., 55° C., 60° C., 65° C., or 70° C. These are average temperatures within the hydrolysis reactor.

Effective enzymatic hydrolysis conditions may include a pH from about 4 to about 6, such as a pH of about, at least about, or at most about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, or 6.0, including any intervening ranges.

When hydrolysis is catalyzed with an acid catalyst rather than enzymes, an effective hydrolysis temperature may be from about 90° C. to about 150° C., and an effective hydrolysis pH may be from about 0.5 to about 2, for example.

When hydrolysis is catalyzed with an alkaline catalyst rather than enzymes, an effective hydrolysis temperature may be from about 90° C. to about 150° C., and an effective hydrolysis pH may be from about 10 to about 12, for example.

Effective hydrolysis conditions may include a pressure of about atmospheric pressure, such as a pressure from about 0.5 bar to about 2 bar, or from about 0.8 bar to about 1.2 bar.

The enzymatic hydrolysis unit may include a single stage configured for cellulose liquefaction and saccharification, wherein the single stage includes one or more tanks or vessels. Alternatively, the enzymatic hydrolysis unit may include two stages configured for cellulose liquefaction followed by saccharification, wherein each stage includes one or more tanks or vessels.

When the hydrolysis process employs enzymes, these enzymes will typically contain cellulases (endoglucanases and exoglucanases) and hemicellulases. The cellulases here may include β-glucosidases that convert cellooligosaccharides and disaccharide cellobiose into glucose. There are enzymes that can attack hemicelluloses, such as (but not limited to) glucoronide, acetylesterase, xylanase, arabinase, β-xylosidase, galactomannase, and glucomannase.

In some embodiments, a hydrolysis reactor is configured to cause at least some liquefaction as a result of enzymatic action on the cellulose-rich solids. "Liquefaction" means partial hydrolysis of cellulose and/or hemicellulose to form sugar oligomers that dissolve into solution, but not total hydrolysis of cellulose or hemicellulose to sugar monomers (saccharification).

Various fractions of cellulose may be hydrolyzed during liquefaction. In some embodiments, the fraction of cellulose hydrolyzed during liquefaction may be from about 5% to about 90%, such as about 10% to about 75%, e.g. about 15%, 20%, 25%, 30%, 35%, 40%, 45%, 50%, 55%, 60%, 65%, or 70%.

Various fractions of hemicellulose may be hydrolyzed during liquefaction. In some embodiments, the fraction of hemicellulose hydrolyzed during liquefaction may be from about 5% to about 90%, such as about 10% to about 75%, e.g. about 15%, 20%, 25%, 30%, 35%, 40%, 45%, 50%, 55%, 60%, 65%, or 70%.

In certain embodiments, there is no separate liquefaction tank or reactor; liquefaction and hydrolysis may occur in the same vessel.

A "liquefaction-focused blend of enzymes" means a mixture of enzymes that includes at least one enzyme capable of hydrolyzing cellulose and/or hemicellulose to form soluble oligomers. In some embodiments, a liquefaction-focused blend of enzymes includes both endoglucanases and exoglucanases. Endoglucanases are cellulases that attack low-crystallinity regions in the cellulose fibers by endoaction, creating free chain-ends. Exoglucanases or cellobiohydrolases are cellulases that hydrolyze the 1,4-glycocidyl linkages in cellobiose.

Various cellulase enzymes may be utilized in the liquefaction-focused blend of enzymes, such as one or more enzymes disclosed in Verardi et al., "Hydrolysis of Lignocellulosic Biomass: Current Status of Processes and Technologies and Future Perspectives," *Bioethanol*, InTech (2012), which is incorporated by reference herein.

Some embodiments employ thermotolerant enzymes obtained from thermophilic microorganisms. The thermophilic microorganisms can be grouped in thermophiles (growth up to 60° C.), extreme thermophiles (65-80° C.) and hyperthermophiles (85-110° C.). The unique stability of the enzymes produced by these microorganisms at elevated temperatures, extreme pH, and high pressure (up to 1000 bar) makes them valuable for processes at harsh conditions. Also, thermophilic enzymes have an increased resistance to many denaturing conditions such as the use of detergents which can be an efficient means to obviate the irreversible adsorption of cellulases on the substrates. Furthermore, the utilization of high operation temperatures, which cause a decrease in viscosity and an increase in the diffusion coefficients of substrates, have a significant influence on the cellulose solubilization. Most thermophilic cellulases do not show inhibition at high level of reaction products (e.g. cellobiose and glucose). As consequence, higher reaction rates and higher process yields are expected. The high process temperature also reduces contamination. See Table 6, "Thermostable cellulases" in Verardi et al., cited above, for exemplary thermotolerant enzymes that may be used in the liquefaction-focused blend of enzymes, or in other embodiments.

In some embodiments, an enzyme is selected such that at a high temperature, the enzyme is able to catalyze liquefaction (partial hydrolysis) but not saccharification (total hydrolysis). When the temperature is reduced, the same enzyme is able to catalyze saccharification to produce glucose monomer.

Some embodiments employ two or more enzymatic hydrolysis units. The first enzymatic hydrolysis unit may include a single stage configured for cellulose liquefaction and saccharification, wherein the single stage includes one or more tanks or vessels. Alternatively, the first enzymatic hydrolysis unit may include two stages configured for cellulose liquefaction followed by saccharification, wherein each stage includes one or more tanks or vessels.

The second enzymatic hydrolysis unit may include a single stage configured for cellulose liquefaction and saccharification, wherein the single stage includes one or more tanks or vessels. Alternatively, the second enzymatic hydrolysis unit may include two stages configured for cellulose liquefaction followed by saccharification, wherein each stage includes one or more tanks or vessels. In certain embodiments, the process further comprises recycling at least some material treated in the second enzymatic hydrolysis unit, for solid/liquid separation, for example.

Enzymes introduced or present in the second enzymatic hydrolysis unit may likewise include cellulases and hemicellulases. In some embodiments, enzymes introduced or present in the second enzymatic hydrolysis unit include endoglucanases and exoglucanases.

The hydrolysis reactor may be configured in one or more stages or vessels. In some embodiments, a hydrolysis reactor is a system of two, three, or more physical vessels which are configured to carry out liquefaction or hydrolysis of sugar oligomers. For example, in certain embodiments, a liquefaction tank is followed by a hydrolysis tank, which is then followed by another tank for extended hydrolysis. Enzymes may be added to any one or more of these vessels, and enzyme recycling may be employed.

In other embodiments, a single physical hydrolysis reactor is utilized, which reactor contains a plurality of zones, such as a liquefaction zone, a first hydrolysis zone, and a second hydrolysis zone. The zones may be stationary or moving, and the reactor may be a continuous plug-flow reactor, a continuous stirred reactor, a batch reactor, a semi-batch reactor, or any combination of these, including arbitrary flow patterns of solid and liquid phases.

A mechanical refiner may be included before liquefaction, between the liquefaction tank and hydrolysis tank, and/or between the hydrolysis tank and the extended hydrolysis tank. Alternatively or additionally, a mechanical refiner may be included elsewhere in the process. Enzymes may be introduced directly into any of the refiners, if desired.

In some embodiments, enzymes are introduced directly to the mechanical refiner. In these or other embodiments, the enzymes are introduced to the digested stream, upstream of the mechanical refiner. The enzymes may include cellulases (e.g., endoglucanases and exoglucanases) and hemicellulases.

In certain embodiments, a self-cleaning filter is configured downstream of a hydrolysis tank to remove cellulose fiber strands prior to sending the hydrolysate to a fermentor or other unit (e.g., another hydrolysis vessel for extended hydrolysis of soluble material). The self-cleaning filter continuously rejects solids (including cellulose fiber strands) that may be recycled back to the first hydrolysis vessel. For example, the cellulose fiber strands may be recycled to a biomass cooler that feeds a viscosity-reduction tank at the beginning of hydrolysis.

Many fluid streams contain particulate matter, and it is often desirable to separate this particulate matter from the fluid stream. If not separated, the particulate matter may degrade product quality, efficiency, reduce performance, or cause severe damage to components within the system. Many types of filters have been designed for the purpose of removing particulate matter from fluid streams. Such filters have typically included a filter element designed to screen the particulate material. However, the particulate material often becomes entrapped in the filter element. As the quantity of particulate material, often referred to as filter cake, collects on the filter element, the pressure drop that occurs across the filter element increases. A pressure drop across the filter element of sufficient magnitude can significantly reduce fluid flow at which point the filter element must be periodically cleaned, or replaced with a new filter. Often, this is done manually by removing the filter element and cleaning the filter before reinstalling it back in the system. To minimize manual operations, filters have been designed to accomplish continuous self-cleaning.

As intended herein, a "self-cleaning filter" should be construed broadly to refer to self-cleaning filtration devices, self-cleaning decanters, self-cleaning screens, self-cleaning centrifuges, self-cleaning cyclones, self-cleaning rotary drums, self-cleaning extruders, or other self-cleaning separation devices.

Some self-cleaning filters use back pulsing to dislodge materials or blades to scrape off caked particulate. Some self-cleaning filters are cleaned with sprayed fluids, such as water or air to remove the particulates. Some self-cleaning filters utilize high pressures or forces to dislodge caked particulate from the filter. Some self-cleaning filters employ a moving (e.g., rotating) filter design wherein particulates are continuously filtered and removed due to centrifugal force or other forces. Many self-cleaning filters are available commercially.

Also see, for example, U.S. Pat. No. 4,552,655, issued Nov. 12, 1985 and U.S. Pat. No. 8,529,661, issued Sep. 10, 2013, which are hereby incorporated by reference for their descriptions of certain self-cleaning filters.

As intended herein, "cellulose fiber strands" generally refer to relatively large, non-soluble cellulose-containing particles in the form of individual fibers or bundles of fibers. Cellulose fiber strands, without limitation, may have lengths or effective lengths in the range of about 0.1 mm to about 10 mm, such as about 0.5 mm to about 5 mm. Some fiber strand bundles may have very large length or particle size, such as about 10 mm or more. The principles of the invention may be applied to smaller cellulose particles, with length or particle size less than 0.1 mm, as long as the particles can be captured by a self-cleaning filter.

In some embodiments, the composition of some cellulose fiber strands may be similar to the composition of the starting biomass material, such as when large particles were not effectively pretreated in the digestor.

In some embodiments, a self-cleaning filter is configured downstream of an enzymatic hydrolysis unit to remove cellulosic fiber strands. The self-cleaning filter is preferably operated continuously. The cellulosic fiber strands may be recycled back to one or more of the one or more enzymatic hydrolysis units, for further cellulose hydrolysis.

In some embodiments, a self-cleaning filter is configured downstream of the enzymatic liquefaction unit to remove cellulosic fiber strands. In these or other embodiments, a self-cleaning filter is configured downstream of the first enzymatic hydrolysis unit to remove cellulosic fiber strands. In these or other embodiments, a self-cleaning filter is configured downstream of the second enzymatic hydrolysis unit to remove cellulosic fiber strands.

At least a portion of the cellulosic fiber strands may be recycled back to the enzymatic liquefaction unit or to vessel or heat exchanger that feeds into the enzymatic liquefaction unit. Alternatively, or additionally, at least a portion of the cellulosic fiber strands are recycled back to the first enzymatic hydrolysis unit or to vessel or heat exchanger that feeds into the first enzymatic hydrolysis unit. Alternatively, or additionally, at least a portion of the cellulosic fiber strands are recycled back to the digestor and/or to one of the mechanical refiners.

Generally speaking, enzymatic hydrolysis should be optimized for the biomass type, the capital cost of tanks versus solids content, energy integration with the rest of the plant, and enzyme cost versus sugar yield. For each commercial implementation, one skilled in the art may carry out a design of experiments in cooperation with an enzyme supplier, or in conjunction with on-site enzyme production. In some embodiments, a process disclosed herein is retrofitted to an existing impregnation system, an existing digestor, an existing refiner, an existing hydrolysis reactor, and/or an existing fermentation system.

The process may further include removal of one or more fermentation inhibitors by stripping. This stripping may be conducted following step (e), i.e. treating the hydrolyzed cellulose stream, prior to fermentation. Alternatively, or additionally, the stripping may be conducted on a stream following digestion, such as in the blow line, or as part of an acetic acid recycle system.

The process may further include a step of fermenting the fermentable sugars to a fermentation product. Typically the process will further include concentration and purification of the fermentation product. The fermentation product may be selected from ethanol, n-butanol, 1,4-butanediol, succinic acid, lactic acid, or combinations thereof, for example.

Some embodiments further include removing a solid stream containing lignin following prior to fermentation of the fermentable sugars. In these or other embodiments, the process may further include removing a solid stream containing lignin following fermentation of the fermentable sugars. The lignin may be combusted for energy production or used for other purposes, such as conversion to carbon products.

Some variations described herein are premised on the design of process options to increase the yield of ethanol production (or other fermentation product). Some process configurations include sending digested pulp, after a hot blow but before any mechanical refining, to continuous enzymatic hydrolysis. The enzymatic hydrolysis may be configured in one step (liquefaction and saccharification in one vessel) or two steps (tanks) in series. The different vessels may be designed/operated as continuous stirred tank reactors. The material (liquid and solid) from the enzymatic hydrolysis may undergo a solid/liquid separation, wherein the liquid phase containing $C_5$ and $C_6$ sugars is sent to fermentation. The solid phase may be sent to an atmospheric pulp refiner wherein further deconstruction of the non-hydrolyzed fiber (solid phase) is achieved by adjusting the refiner power load and physical parameters (e.g., dimensions of gaps or grooves). Next, the refined fiber is sent to another enzymatic hydrolysis unit or is recycled back to the primary hydrolysis unit. These embodiments may increase enzymatic hydrolysis yield by recycling more deconstructed fiber, and/or increase fiber digestibility to fermentation microorganisms which translates into higher product yield. Less solids sent to fermentation translates to higher fermentation yield. A cleaner fermentation beer will cause less fouling of the beer column.

Some variations utilize a process for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) reducing pressure of the digested stream;
(d) introducing the digested stream to an enzymatic hydrolysis unit under effective hydrolysis conditions to produce a liquid phase comprising sugars from the cellulose-rich solids and optionally from the hemicellulose oligomers, and a solid phase comprising the cellulose-rich solids;
(e) separating the liquid phase and the solid phase from step (d);
(f) conveying the solid phase through a mechanical refiner, thereby generating a refined stream with reduced average particle size of the cellulose-rich solids;
(g) recycling the refined stream to the enzymatic hydrolysis unit, to produce additional sugars from the cellulose-rich solids contained in the solid phase from step (d); and
(h) recovering or further processing at least some of the sugars and at least some of the additional sugars as fermentable sugars.

Other variations utilize a process for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) reducing pressure of the digested stream;
(d) introducing the digested stream to a first enzymatic hydrolysis unit under effective hydrolysis conditions to produce a liquid phase comprising sugars from the cellulose-rich solids and optionally from the hemicellulose oligomers, and a solid phase comprising the cellulose-rich solids;
(e) separating the liquid phase and the solid phase from step (d);
(f) conveying the solid phase through a mechanical refiner, thereby generating a refined stream with reduced average particle size of the cellulose-rich solids;
(g) recycling the refined stream to a second enzymatic hydrolysis unit, to produce additional sugars from the cellulose-rich solids contained in the solid phase from step (d); and
(h) recovering or further processing at least some of the sugars and/or the additional sugars as fermentable sugars.

Some variations utilize a process for producing fermentable sugars from cellulosic biomass, the process comprising:
(a) generating an impregnated biomass material, wherein the impregnated biomass material includes (i) a feedstock containing cellulose, hemicellulose, and lignin and (ii) a reaction solution;
(b) exposing the biomass material to the impregnated reaction solution comprising steam or liquid hot water within the digestor under effective reaction conditions to produce a digested stream containing cellulose-rich solids, hemicellulose oligomers, and lignin;
(c) optionally conveying the digested stream through a mechanical refiner, thereby generating a refined stream with reduced average particle size of the cellulose-rich solids;
(d) introducing the digested stream and/or (if step (c) is conducted) the refined stream to an enzymatic hydrolysis unit under effective hydrolysis conditions to produce a sugar-containing hydrolysate;
(e) evaporating the hydrolysate using a multiple-effect evaporator or a mechanical vapor compression evaporator, to produce a concentrated hydrolysate;
(f) fermenting the concentrated hydrolysate to produce a dilute fermentation product; and
(g) concentrating the dilute fermentation product to produce a concentrated fermentation product.

Step (d) may be conducted at a solid concentration from about 5 wt % to about 25 wt %, such as about 10 wt %, 15 wt %, or 20 wt %.

Step (g) may utilize distillation, which generates a distillation bottoms stream. In some embodiments, the distillation bottoms stream is evaporated in a distillation bottoms evaporator that is integrated with step (e) in a multiple-effect evaporator train. The distillation bottoms evaporator may provide lignin-rich combustion fuel.

Suspended solids (lignin or other solids) may be removed prior to step (e). In some embodiments, suspended solids are removed during or after step (e) and prior to the distillation bottoms evaporator.

The concentrated fermentation product may be selected from ethanol, n-butanol, isobutanol, 1,4-butanediol, succinic acid, lactic acid, or combinations thereof, for example. In certain embodiments, the concentrated fermentation product is ethanol.

In some embodiments, the process includes washing the cellulose-rich solids using an aqueous wash solution, to produce a wash filtrate; and optionally combining at least some of the wash filtrate with the extract liquor. In some of these embodiments, the process further includes pressing the cellulose-rich solids to produce the washed cellulose-rich solids and a press filtrate; and optionally combining at least some of the press filtrate with the extract liquor.

The process may include countercurrent washing, such as in two, three, four, or more washing stages. The separation/washing may be combined with the application of enzymes, in various ways.

Two hydrolysis catalysts may be utilized in series. In some embodiments, a first hydrolysis catalyst includes cellulases. In some embodiments, a second hydrolysis catalyst includes hemicellulases. In other embodiments, the first hydrolysis catalyst and the second hydrolysis catalyst are acid catalysts, base catalysts, ionic liquids, solid catalysts, or other effective materials. The first hydrolysis catalyst may be the same as, or different than, the second hydrolysis catalyst.

In some embodiments, the glucose is recovered in a separate stream from the hemicellulose monomers. In other embodiments, the glucose and the hemicellulose monomers are recovered in the same stream. The process may include fermentation of the glucose and/or the fermentable hemicellulose sugars to a fermentation product.

In some embodiments, the process starts as biomass is received or reduced to a desired particle size. In a first step of the process, the biomass is fed (e.g., from a feed bin) to an impregnation system as disclosed above. Impregnated biomass material is fed to a pressurized extraction vessel operating continuously or in batch mode. The biomass may first be water-washed to remove dirt. The pressurized extraction vessel is heated to a temperature between about 100° C. to about 250° C., for example 150° C., 160° C., 170° C., 180° C., 190° C., 200° C., or 210° C. Preferably, the biomass is heated to about 180° C. to 210° C.

The pressure in the pressurized vessel may be adjusted to maintain the aqueous liquor as a liquid, a vapor, or a combination thereof. Exemplary pressures are about 1 bar to about 30 bar, such as about 3 bar, 5 bar, 10 bar, or 15 bar.

The solid-phase residence time for the digestor (pressurized extraction vessel) may vary from about 2 minutes to about 4 hours, such as about 5 minutes to about 1 hour. In certain embodiments, the digestor residence time is controlled to be about 5 to 15 minutes, such as 5, 6, 7, 8, 9, 10, 11, 12, 13, 14 or 15 minutes. The liquid-phase residence time for the digestor may vary from about 2 minutes to about 4 hours, such as about 5 minutes to about 1 hour. The vapor-phase residence time for the digestor may vary from about 1 minute to about 2 hours, for example, such as about 3 minutes to about 30 minutes. The solid-phase, liquid-phase, and vapor-phase residence times may all be about the same, or they may be independently controlled according to reactor-engineering principles (e.g., recirculation strategies).

The aqueous liquor may contain acidifying compounds, such as (but not limited to) sulfuric acid, sulfurous acid, sulfur dioxide, acetic acid, formic acid, or oxalic acid, or combinations thereof. The dilute acid concentration (if any) can range from 0.01 wt % to 10 wt % as necessary to improve solubility of particular minerals, such as potassium, sodium, or silica. Preferably, the acid concentration is selected from about 0.01 wt % to 4 wt %, such as 0.1 wt %, 0.5 wt %, or 1 wt %.

A second step may include depressurization of the extracted biomass into a blow tank or other tank or unit. The vapor can be used for heating the incoming biomass or cooking liquor, directly or indirectly. The volatilized organic acids (e.g., acetic acid), which are generated or included in the cooking step, may be recycled back to the cooking.

A third step may include mechanically refining the extracted biomass. This step (using, for example, a blow-line refiner) may be done before or after depressurization.

Optionally, refined solids may be washed. The washing may be accomplished with water, recycled condensates, recycled permeate, or a combination thereof. Washing typically removes most of the dissolved material, including hemicelluloses and minerals. The final consistency of the dewatered cellulose-rich solids may be increased to 30% or more, preferably to 50% or more, using a mechanical pressing device. The mechanical pressing device may be integrated with the mechanical refiner, to accomplish combined refining and washing.

A fourth step may include hydrolyzing the extracted chips with enzymes to convert some of the cellulose to glucose. When enzymes are employed for the cellulose hydrolysis, the enzymes preferably include cellulase enzymes. Enzymes may be introduced to the extracted chips along with water, recycled condensates, recycled permeate, additives to adjust pH, additives to enhance hydrolysis (such as lignosulfonates), or combinations thereof.

Some or all of the enzymes may be added to the blow line before or at a blow-line refiner, for example, to assist in enzyme contact with fibers. In some embodiments, at least a portion of enzymes are recycled in a batch or continuous process.

When an acid is employed for the cellulose hydrolysis, the acid may be selected from sulfuric acid, sulfurous acid, sulfur dioxide, formic acid, acetic acid, oxalic acid, or combinations thereof. Acids may be added to the extracted chips before or after mechanical refining. In some embodiments, dilute acidic conditions are used at temperatures between about 100° C. and 190° C., for example about 120° C., 130° C., 140° C., 150° C., 160° C., or 170° C., and preferably from 120° C. to 150° C. In some embodiments, at least a portion of the acid is recycled in a batch or continuous process.

The acid may be selected from sulfuric acid, sulfurous acid, or sulfur dioxide. Alternatively, or additionally, the acid may include formic acid, acetic acid, or oxalic acid from the cooking liquor or recycled from previous hydrolysis.

A fifth step may include conditioning of hydrolysate to remove some or most of the volatile acids and other fermentation inhibitors. The evaporation may include flashing or stripping to remove sulfur dioxide, if present, prior to removal of volatile acids. The evaporation step is preferably performed below the acetic acid dissociation pH of 4.8, and most preferably a pH selected from about 1 to about 2.5. In some embodiments, additional evaporation steps may be employed. These additional evaporation steps may be conducted at different conditions (e.g., temperature, pressure, and pH) relative to the first evaporation step.

In some embodiments, some or all of the organic acids evaporated may be recycled, as vapor or condensate, to the first step (cooking step) to assist in the removal of hemicelluloses or minerals from the biomass. This recycle of organic acids, such as acetic acid, may be optimized along with process conditions that may vary depending on the amount recycled, to improve the cooking effectiveness.

A sixth step may include recovering fermentable sugars, which may be stored, transported, or processed. A sixth step may include fermenting the fermentable sugars to a product, as further discussed below.

A seventh step may include preparing the solid residuals (containing lignin) for combustion. This step may include refining, milling, fluidizing, compacting, and/or pelletizing the dried, extracted biomass. The solid residuals may be fed to a boiler in the form of fine powder, loose fiber, pellets, briquettes, extrudates, or any other suitable form. Using known equipment, solid residuals may be extruded through a pressurized chamber to form uniformly sized pellets or briquettes.

In some embodiments, the fermentable sugars are recovered from solution, in concentrated form. In some embodiments, the fermentable sugars are fermented to produce biochemicals or biofuels such as (but by no means limited to) ethanol, 1-butanol, isobutanol, acetic acid, lactic acid, or any other fermentation products. A purified fermentation product may be produced by distilling the fermentation product, which will also generate a distillation bottoms stream containing residual solids. A bottoms evaporation stage may be used, to produce residual solids.

Following fermentation, residual solids (such as distillation bottoms) may be recovered, or burned in solid or slurry form, or recycled to be combined into the biomass pellets. Use of the fermentation residual solids may require further removal of minerals. Generally, any leftover solids may be used for burning, after concentration of the distillation bottoms.

Alternatively, or additionally, the process may include recovering the residual solids as a fermentation co-product in solid, liquid, or slurry form. The fermentation co-product may be used as a fertilizer or fertilizer component, since it will typically be rich in potassium, nitrogen, and/or phosphorous.

In certain embodiments, the process further comprises combining, at a pH of about 4.8 to 10 or higher, a portion of vaporized acetic acid with an alkali oxide, alkali hydroxide, alkali carbonate, and/or alkali bicarbonate, wherein the alkali is selected from the group consisting of potassium, sodium, magnesium, calcium, and combinations thereof, to convert the portion of the vaporized acetic acid to an alkaline acetate. The alkaline acetate may be recovered. If desired, purified acetic acid may be generated from the alkaline acetate.

In some variations, fermentation inhibitors are separated from a biomass-derived hydrolysate, such as by the following steps:
(a) providing a biomass-derived liquid hydrolysate stream comprising a fermentation inhibitor;
(b) introducing the liquid hydrolysate stream to a stripping column;
(c) introducing a steam-rich vapor stream to the stripping column to strip at least a portion of the fermentation inhibitor from the liquid hydrolysate stream;
(d) recovering, from the stripping column, a stripped liquid stream and a stripper vapor output stream, wherein the stripped liquid stream has lower fermentation inhibitor concentration than the liquid hydrolysate stream;
(e) compressing the stripper vapor output stream to generate a compressed vapor stream;
(f) introducing the compressed vapor stream, and a water-rich liquid stream, to an evaporator;
(g) recovering, from the evaporator, an evaporated liquid stream and an evaporator output vapor stream; and
(h) recycling at least a portion of the evaporator output vapor stream to the stripping column as the steam-rich vapor stream, or a portion thereof.

The biomass-derived hydrolysate may be the product of acidic or enzymatic hydrolysis, or it may be material from the digestor, for example. In some embodiments, the fermentation inhibitor is selected from the group consisting of acetic acid, formic acid, formaldehyde, acetaldehyde, methanol, lactic acid, furfural, 5-hydroxymethylfurfural, furans, uronic acids, phenolic compounds, terpenes, sulfur-containing compounds, and combinations or derivatives thereof.

In some embodiments, the water-rich liquid stream contains biomass solids that are concentrated in the evaporator. These biomass solids may be derived from the same biomass feedstock as is the biomass-derived liquid hydrolysate, in an integrated process.

Optionally, the fermentation inhibitor is recycled to a previous unit operation (e.g., digestor or reactor) for generating the biomass-derived liquid hydrolysate stream, to assist with hydrolysis or pretreatment of a biomass feedstock or component thereof. For example, acetic acid may be recycled for this purpose, to aid in removal of hemicelluloses from biomass and/or in oligomer hydrolysis to monomer sugars.

Some variations utilize a process for separating fermentation inhibitors from a biomass-derived hydrolysate, the process comprising:
(a) providing a biomass-derived liquid hydrolysate stream comprising a fermentation inhibitor;
(b) introducing the liquid hydrolysate stream to a stripping column;
(c) introducing a steam-rich vapor stream to the stripping column to strip at least a portion of the fermentation inhibitor from the liquid hydrolysate stream;
(d) recovering, from the stripping column, a stripped liquid stream and a stripper vapor output stream, wherein the stripped liquid stream has lower fermentation inhibitor concentration than the liquid hydrolysate stream;
(e) introducing the stripper vapor output stream, and a water-rich liquid stream, to an evaporator;
(f) recovering, from the evaporator, an evaporated liquid stream and an evaporator output vapor stream;
(g) compressing the evaporator output vapor stream to generate a compressed vapor stream; and
(h) recycling at least a portion of the compressed vapor stream to the stripping column as the steam-rich vapor stream, or a portion thereof.

In some embodiments, the evaporator is a boiler, the water-rich liquid stream comprises boiler feed water, and the evaporated liquid stream comprises boiler condensate.

The stripping process may be continuous, semi-continuous, or batch. When continuous or semi-continuous, the stripping column may be operated countercurrently, cocurrently, or a combination thereof.

In certain variations, a process is utilized for separating and recovering a fermentation inhibitor from a biomass-derived hydrolysate comprises:
(a) providing a biomass-derived liquid hydrolysate stream comprising a fermentation inhibitor;
(b) introducing the liquid hydrolysate stream to a stripping column;
(c) introducing a steam-rich vapor stream to the stripping column to strip at least a portion of the fermentation inhibitor from the liquid hydrolysate stream;
(d) recovering, from the stripping column, a stripped liquid stream and a stripper vapor output stream, wherein the stripped liquid stream has lower fermentation inhibitor concentration than the liquid hydrolysate stream;
(e) introducing the stripper vapor output stream, and a water-rich liquid stream, to a rectification column;
(f) recovering, from the rectification column, a rectified liquid stream and a rectification column vapor stream, wherein the rectified liquid stream has higher fermentation inhibitor concentration than the liquid hydrolysate stream; and
(g) recycling at least a portion of the rectification column vapor stream to the stripping column as the steam-rich vapor stream, or a portion thereof.

The fermentation inhibitor may be selected from the group consisting of acetic acid, formic acid, formaldehyde, acetaldehyde, lactic acid, furfural, 5-hydroxymethylfurfural, furans, uronic acids, phenolic compounds, sulfur-containing compounds, and combinations or derivatives thereof. In some embodiments, the fermentation inhibitor comprises or consists essentially of acetic acid.

In the case of acetic acid, the stripped liquid stream preferably has less than 10 g/L acetic acid concentration, such as less than 5 g/L acetic acid concentration. The rectification column vapor stream preferably has less than 0.5 g/L acetic acid concentration, such as less than 0.1 g/L acetic acid concentration. The rectified liquid stream preferably has at least 25 g/L acetic acid concentration, such as about 40 g/L or more acetic acid. In some embodiments, the rectified liquid stream has at least 10 times higher concentration of acetic acid compared to the stripped liquid stream. In certain embodiments, the process further comprises recovering the acetic acid contained in the rectified liquid stream using liquid-vapor extraction or liquid-liquid extraction.

In some embodiments, the water-rich liquid stream includes evaporator condensate. The evaporator condensate may be derived from an evaporator in which biomass solids are concentrated, and the biomass solids may be derived from the same biomass feedstock as the biomass-derived liquid hydrolysate, in an integrated process.

Optionally, the fermentation inhibitor (e.g., acetic acid) is recycled to a previous unit operation for generating the biomass-derived liquid hydrolysate stream, to assist with hydrolysis or pretreatment of a biomass feedstock or component thereof.

The rectification process may be continuous, semi-continuous, or batch. When continuous or semi-continuous, the stripping column may be operated countercurrently, cocurrently, or a combination thereof. The rectification column may be operated continuously or in batch.

In various embodiments, step (g) comprises compressing and/or conveying the rectification column vapor stream using a device selected from the group consisting of a mechanical centrifugal vapor compressor, a mechanical axial vapor compressor, a thermocompressor, an ejector, a diffusion pump, a turbomolecular pump, and combinations thereof.

If desired, a base or other additive may be included in the water-rich liquid stream, or separately introduced to the rectification column, to produce salts or other reaction products derived from fermentation inhibitors. In some embodiments, the water-rich liquid stream includes one or more additives capable of reacting with the fermentation inhibitor. In certain embodiments, the fermentation inhibitor includes acetic acid, and the one or more additives include a base. An acetate salt may then be generated within the rectification column, or in a unit coupled to the rectification column. Optionally, the acetate salt may be separated and recovered using liquid-vapor extraction or liquid-liquid extraction.

In some embodiments, the process is a variation of Green Power+® and/or GP3+® process technology which is commonly owned with the assignee of this patent application.

Generally, the present invention is not limited by the components of the reaction solution. As explained in this specification, the reaction solution typically contains water and may contain one or more pretreatment chemicals (e.g., acids, bases, or salts) that may function as hydrolysis catalysts and/or may have other functions. The reaction solution may contain additives, impurities (e.g., silica or dirt), entrained gases, and other components that do not materially affect the process efficiency. Strictly speaking, water is not absolutely necessary in the reaction solution; for example, a non-aqueous liquid could be employed as the liquid solution for impregnation.

The reaction solution may contain a solvent for lignin, which can be advantageous to enable better delignification from a starting feedstock as well as more-efficient lignin management in the overall process. In the present specification, for convenience, the following section describes processes and systems that utilize a solvent for lignin. The above sections describe processes and systems that may utilize a solvent for lignin, but not necessarily.

In some embodiments, the solvent for lignin comprises an organic acid. For example, without limitation, the organic acid may be selected from the group consisting of acetic acid, formic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, and combinations thereof. In these or other embodiments, the solvent for lignin comprises an inorganic acid, such as concentrated phosphoric acid.

The process may further include recovering the lignin, lignosulfonates, or both of these. Recovery of lignin typically involves removal of solvent, dilution with water, adjustment of temperature or pH, addition of an acid or base, or some combination thereof.

The sulfur dioxide may be present in a liquid-phase concentration of about 1 wt % to about 50 wt % during step (a), such as about 3 wt % to about 30 wt %, e.g. about 5 wt % to about 10 wt %, in various embodiments.

Step (b) typically includes washing of the cellulose-rich solids, which preferably includes countercurrent washing of the cellulose-rich solids.

Hydrolyzing the hemicellulose contained in the liquor, in step (c), may be catalyzed by lignosulfonic acids that are generated during step (a).

The fermentation product may include an organic acid, such as (but not limited to) organic acids selected from the group consisting of formic acid, acetic acid, oxalic acid, lactic acid, propionic acid, 3-hydroxypropionic acid, malonic acid, aspartic acid, fumaric acid, malic acid, succinic acid, glutaric acid, adipic acid, citric acid, itaconic acid, levulinic acid, ascorbic acid, gluconic acid, kojic acid, threonine, glutamic acid, proline, lysine, alanine, serine, and any isomers, derivatives, or combinations thereof. In certain embodiments, the organic acid is succinic acid. "Derivatives" may be salts of these acids, or esters, or reaction products to convert the acid to another molecule that is not an acid. For example, when the fermentation product is succinic acid, it may be further converted to 1,4-butanediol as a derivative using known hydrotreating chemistry.

The fermentation product may include an oxygenated compound, such as (but not limited to) oxygenated compounds selected from the group consisting of ethanol, propanol, butanol, pentanol, hexanol, heptanol, octanol, glycerol, sorbitol, propanediol, butanediol, butanetriol, pentanediol, hexanediol, acetone, acetoin, butyrolactone, 3-hydroxybutyrolactone, and any isomers, derivatives, or combinations thereof.

In some embodiments, the oxygenated compound is a $C_3$ or higher alcohol or diol, such as 1-butanol, isobutanol, 1,4-butanediol, 2,3-butanediol, or mixtures thereof.

The fermentation product may include a hydrocarbon, such as isoprene, α-farnasene (3,7,11-trimethyl-1,3,6,10-dodecatetraene), and related compounds.

Multiple fermentation products may be produced in a single fermentor, in co-product production or as a result of byproducts due to contaminant microorganisms. For example, during fermentation to produce lactic acid, ethanol is a common byproduct due to contamination (and vice-versa).

Multiple fermentation products may be produced in separate fermentors. In some embodiments, a first fermentation product, such as an organic acid, is produced from glucose (hydrolyzed cellulose) while a second fermentation product, such as ethanol, is produced from hemicellulose sugars. Or, in some embodiments, different fermentations are directed to portions of feedstock having varying particle size, crystallinity, or other properties.

In some embodiments, different fermentations are directed to portions of whole biomass that is separated into a starch or sucrose-rich fraction, and a cellulose-rich fraction (for example, corn starch/stover or sugarcane syrup/bagasse). For example, from raw corn, an organic acid or polyol may be produced from starch (hydrolyzed to glucose), the same or a different organic acid or polyol may be produced from cellulose (hydrolyzed to glucose), and ethanol may be produced from hemicellulose sugars. Many variations are possible, as will be recognized by a person skilled in the biorefinery art, in view of the present disclosure.

The solvent for lignin may include a component that is the same as the fermentation product. In some embodiments, the solvent for lignin is the same compound as the fermentation product. For example, the solvent and the fermentation product may be 1-butanol, or lactic acid, succinic acid, or 1,4-butanediol. Of course, other solvents may be present even when these products are utilized as solvents or co-solvents. Beneficially, a portion of the fermentation product may be recycled to step (a) for use as the solvent for lignin.

In some embodiments, the fermentation product includes an enzymatically isomerized variant of at least a portion of the fermentable sugars. For example, the enzymatically isomerized variant may include fructose which is isomerized from glucose. In some embodiments, glucose, which is normally D-glucose, is isomerized with enzymes to produce L-glucose.

In some embodiments, the fermentation product includes one or more proteins, amino acids, enzymes, or microorganisms. Such fermentation products may be recovered and used within the process; for example, cellulase or hemicellulase enzymes may be used for hydrolyzing cellulose-rich solids or hemicellulose oligomers.

Some variations are premised on the recognition that the clean cellulose produced may be not only hydrolyzed to glucose, but also recovered as a cellulose pulp product, intermediate, or precursor (such as for nanocellulose). Also, when employing a solvent for lignin, the initial fractionation step (in the digestor) does not necessarily employ $SO_2$ as the hydrolysis catalyst.

In some variations, a process for fractionating lignocellulosic biomass into cellulose, hemicellulose, and lignin comprises:
  (a) in a digestor, fractionating an impregnated biomass material in the presence of a solvent for lignin, a hydrolysis catalyst, and water, to produce a liquor containing hemicellulose, cellulose-rich solids, and lignin;
  (b) substantially separating the cellulose-rich solids from the liquor;
  (c) hydrolyzing the hemicellulose contained in the liquor to produce hemicellulosic monomers;
  (d) recovering the hemicellulosic monomers as fermentable sugars;
  (e) fermenting at least a portion of the fermentable sugars to a fermentation product having a higher normal boiling point than water; and
  (f) recovering the fermentation product.

The hydrolysis catalyst in step (a) may be selected from the group consisting of sulfur dioxide, sulfur trioxide, sulfurous acid, sulfuric acid, sulfonic acid, lignosulfonic acid, elemental sulfur, polysulfides, and combinations or derivatives thereof, for example.

In some embodiments, hydrolyzing in step (c) utilizes the hydrolysis catalyst from step (a), or a reaction product thereof. For example, in certain embodiments the hydrolysis catalyst is sulfur dioxide and the reaction product is lignosulfonic acid. In other embodiments, the hydrolyzing in step (c) utilizes hemicellulase enzymes as a hydrolysis catalyst.

In some embodiments, the solvent for lignin also contains the functionality of a hydrolysis catalyst, i.e. there is not a separate hydrolysis catalyst present. In particular, when the solvent for lignin is phosphoric acid or an organic acid, such acid serve dual functions of solvent for lignin plus hydrolysis catalyst.

In some embodiments, the process further comprises saccharifying at least some of the cellulose-rich solids to produce glucose. In these or other embodiments, the process further comprises recovering or further treating or reacting at least some of the cellulose-rich solids as a pulp precursor or product. When glucose is produced (by acid or enzyme hydrolysis of the cellulose), that glucose may form part of the fermentable sugars, either separately from the hemicellulose-derived fermentable sugars, or as a combined sugar stream.

In some embodiments, the fermentation product is ethanol, 1-butanol, succinic acid, 1,4-butanediol, or a combination thereof. In some embodiments, the solvent for lignin includes a component that is the same as the fermentation product, or is the same compound as the fermentation product. Thus a portion of the fermentation product may be recycled to step (a) for use as the solvent for lignin.

Some variations utilize a process for fractionating lignocellulosic biomass into cellulose, hemicellulose, and lignin, the process comprising:
  (a) in a digestor, fractionating an impregnated biomass material in the presence of a solvent for lignin, a hydrolysis catalyst, and water, to produce a liquor containing hemicellulose, cellulose-rich solids, and lignin;
  (b) substantially separating the cellulose-rich solids from the liquor;
  (c) hydrolyzing the hemicellulose contained in the liquor to produce hemicellulosic monomers;
  (d) recovering the hemicellulosic monomers as fermentable sugars;
  (e) fermenting at least a portion of the fermentable sugars to a fermentation product having a relative volatility with water of less than 1.0; and
  (f) recovering the fermentation product.

In any of the embodiments described above, the process may further include hydrolyzing at least a portion of the cellulose-rich solids into glucose, and optionally fermenting the glucose to the fermentation product.

Some variations utilize a process for fractionating lignocellulosic biomass into cellulose, hemicellulose, and lignin, the process comprising:
  (a) in a digestor, fractionating an impregnated biomass material in the presence of a solvent for lignin, a hydrolysis catalyst, and water, to produce a liquor containing hemicellulose, cellulose-rich solids, and lignin;

(b) hydrolyzing the hemicellulose contained in the liquor to produce hemicellulosic monomers;

(c) substantially separating the cellulose-rich solids from the liquor;

(d) recovering the hemicellulosic monomers as fermentable sugars;

(e) fermenting at least a portion of the fermentable sugars to a fermentation product having a relative volatility with water of less than 1.0; and (f) recovering the fermentation product, wherein steps (a) and (b) are optionally combined in a single vessel.

When employing a solvent for lignin, reaction conditions and operation sequences may vary widely. Some embodiments employ conditions described in U.S. Pat. No. 8,030,039, issued Oct. 4, 2011; U.S. Pat. No. 8,038,842, issued Oct. 11, 2011; and/or U.S. Pat. No. 8,268,125, issued Sep. 18, 2012, for example. Each of these commonly owned patent applications is hereby incorporated by reference herein in its entirety. In some embodiments, the process is a variation of AVAP® process technology which is commonly owned with the assignee of this patent application.

In some embodiments, following the impregnation process described above, a process step is "cooking" (equivalently, "digesting") which fractionates the impregnated biomass material into three lignocellulosic material components (cellulose, hemicellulose, and lignin) to allow easy downstream removal. Specifically, hemicelluloses are dissolved and over 50% are completely hydrolyzed; cellulose is separated but remains resistant to hydrolysis; and part of the lignin is sulfonated into water-soluble lignosulfonates.

The lignocellulosic material is processed in a solution (cooking liquor) of aliphatic alcohol, water, and sulfur dioxide. The cooking liquor preferably contains at least 10 wt %, such as at least 20 wt %, 30 wt %, 40 wt %, or 50 wt % of a solvent for lignin. For example, the cooking liquor may contain about 30-70 wt % solvent, such as about 50 wt % solvent. The solvent for lignin may be an aliphatic alcohol, such as methanol, ethanol, 1-propanol, 2-propanol, 1-butanol, 2-butanol, isobutanol, 1-pentanol, 1-hexanol, or cyclohexanol. The solvent for lignin may be an aromatic alcohol, such as phenol or cresol. Other lignin solvents are possible, such as (but not limited to) glycerol, methyl ethyl ketone, or diethyl ether. Combinations of more than one solvent may be employed.

Preferably, enough solvent is included in the extractant mixture to dissolve the lignin present in the starting material. The solvent for lignin may be completely miscible, partially miscible, or immiscible with water, so that there may be more than one liquid phase. Potential process advantages arise when the solvent is miscible with water, and also when the solvent is immiscible with water. When the solvent is water-miscible, a single liquid phase forms, so mass transfer of lignin and hemicellulose extraction is enhanced, and the downstream process must only deal with one liquid stream. When the solvent is immiscible in water, the extractant mixture readily separates to form liquid phases, so a distinct separation step can be avoided or simplified. This can be advantageous if one liquid phase contains most of the lignin and the other contains most of the hemicellulose sugars, as this facilitates recovering the lignin from the hemicellulose sugars.

The cooking liquor preferably contains sulfur dioxide and/or sulfurous acid ($H_2SO_3$). The cooking liquor preferably contains $SO_2$, in dissolved or reacted form, in a concentration of at least 1 wt %, preferably at least 2 wt %, such as about, at least about, or at most about 2 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 20 wt %, 25 wt %, or 30 wt %, including all intervening ranges. The cooking liquor may also contain one or more species, separately from $SO_2$, to adjust the pH. The pH of the cooking liquor is typically about 4 or less.

Sulfur dioxide is a preferred acid catalyst, because it can be recovered easily from solution after hydrolysis. The majority of the $SO_2$ from the hydrolysate may be stripped and recycled back to the reactor. Recovery and recycling translates to less lime required compared to neutralization of comparable sulfuric acid, less solids to dispose of, and less separation equipment. The increased efficiency owing to the inherent properties of sulfur dioxide mean that less total acid or other catalysts may be required. This has cost advantages, since sulfuric acid can be expensive. Additionally, and quite significantly, less acid usage also will translate into lower costs for a base (e.g., lime) to increase the pH following hydrolysis, for downstream operations. Furthermore, less acid and less base will also mean substantially less generation of waste salts (e.g., gypsum) that may otherwise require disposal.

In some embodiments, an additive may be included in amounts of about 0.1 wt % to 10 wt % or more to increase cellulose viscosity. Exemplary additives include ammonia, ammonia hydroxide, urea, anthraquinone, magnesium oxide, magnesium hydroxide, sodium hydroxide, and their derivatives.

The cooking is performed in one or more stages using batch or continuous digestors. Solid and liquid may flow cocurrently or countercurrently, or in any other flow pattern that achieves the desired fractionation. The cooking reactor may be internally agitated, if desired.

Depending on the lignocellulosic material to be processed, the cooking conditions are varied, with temperatures from about 65° C. to 175° C., for example 75° C., 85° C., 95° C., 105° C., 115° C., 125° C., 130° C., 135° C., 140° C., 145° C., 150° C., 155° C., 165° C. or 170° C., and corresponding pressures from about 1 atmosphere to about 15 atmospheres in the liquid or vapor phase. The cooking time of one or more stages may be selected from about 15 minutes to about 720 minutes, such as about 30, 45, 60, 90, 120, 140, 160, 180, 250, 300, 360, 450, 550, 600, or 700 minutes. Generally, there is an inverse relationship between the temperature used during the digestion step and the time needed to obtain good fractionation of the biomass into its constituent parts.

The cooking liquor to lignocellulosic material ratio may be selected from about 1 to about 10, such as about 2, 3, 4, 5, or 6. In some embodiments, biomass is digested in a pressurized vessel with low liquor volume (low ratio of cooking liquor to lignocellulosic material), so that the cooking space is filled with ethanol and sulfur dioxide vapor in equilibrium with moisture. The cooked biomass is washed in alcohol-rich solution to recover lignin and dissolved hemicelluloses, while the remaining pulp is further processed. In some embodiments, the process of fractionating lignocellulosic material comprises vapor-phase cooking of lignocellulosic material with aliphatic alcohol (or other solvent for lignin), water, and sulfur dioxide. See, for example, U.S. Pat. Nos. 8,038,842 and 8,268,125 which are incorporated by reference herein.

A portion or all of the sulfur dioxide may be present as sulfurous acid in the extract liquor. In certain embodiments, sulfur dioxide is generated in situ by introducing sulfurous acid, sulfite ions, bisulfite ions, combinations thereof, or a salt of any of the foregoing. Excess sulfur dioxide, following hydrolysis, may be recovered and reused.

In some embodiments, sulfur dioxide is saturated in water (or aqueous solution, optionally with an alcohol) at a first temperature, and the hydrolysis is then carried out at a second, generally higher, temperature. In some embodiments, sulfur dioxide is sub-saturated. In some embodiments, sulfur dioxide is super-saturated. In some embodiments, sulfur dioxide concentration is selected to achieve a certain degree of lignin sulfonation, such as 1%, 2%, 3%, 4%, 5%, 6%, 7%, 8%, 9%, or 10% sulfur content. $SO_2$ reacts chemically with lignin to form stable lignosulfonic acids which may be present in both the solid and liquid phases.

The concentration of sulfur dioxide, additives, and aliphatic alcohol (or other solvent) in the solution and the time of cook may be varied to control the yield of cellulose and hemicellulose in the pulp. The concentration of sulfur dioxide and the time of cook may be varied to control the yield of lignin versus lignosulfonates in the hydrolysate. In some embodiments, the concentration of sulfur dioxide, temperature, and the time of cook may be varied to control the yield of fermentable sugars.

Once the desired amount of fractionation of both hemicellulose and lignin from the solid phase is achieved, the liquid and solid phases are separated. Conditions for the separation may be selected to minimize the reprecipitation of the extracted lignin on the solid phase. This is favored by conducting separation or washing at a temperature of at least the glass-transition temperature of lignin (about 120° C.).

The physical separation can be accomplished either by transferring the entire mixture to a device that can carry out the separation and washing, or by removing only one of the phases from the reactor while keeping the other phase in place. The solid phase can be physically retained by appropriately sized screens through which liquid can pass. The solid is retained on the screens and can be kept there for successive solid-wash cycles. Alternately, the liquid may be retained and solid phase forced out of the reaction zone, with centrifugal or other forces that can effectively transfer the solids out of the slurry. In a continuous system, countercurrent flow of solids and liquid can accomplish the physical separation.

The recovered solids normally will contain a quantity of lignin and sugars, some of which can be removed easily by washing. The washing-liquid composition can be the same as or different than the liquor composition used during fractionation. Multiple washes may be performed to increase effectiveness. Preferably, one or more washes are performed with a composition including a solvent for lignin, to remove additional lignin from the solids, followed by one or more washes with water to displace residual solvent and sugars from the solids. Recycle streams, such as from solvent-recovery operations, may be used to wash the solids.

After separation and washing as described, a solid phase and at least one liquid phase are obtained. The solid phase contains substantially undigested cellulose. A single liquid phase is usually obtained when the solvent and the water are miscible in the relative proportions that are present. In that case, the liquid phase contains, in dissolved form, most of the lignin originally in the starting lignocellulosic material, as well as soluble monomeric and oligomeric sugars formed in the hydrolysis of any hemicellulose that may have been present. Multiple liquid phases tend to form when the solvent and water are wholly or partially immiscible. The lignin tends to be contained in the liquid phase that contains most of the solvent. Hemicellulose hydrolysis products tend to be present in the liquid phase that contains most of the water.

In some embodiments, hydrolysate from the cooking step is subjected to pressure reduction. Pressure reduction may be done at the end of a cook in a batch digestor, or in an external flash tank after extraction from a continuous digestor, for example. The flash vapor from the pressure reduction may be collected into a cooking liquor make-up vessel. The flash vapor contains substantially all the unreacted sulfur dioxide which may be directly dissolved into new cooking liquor. The cellulose is then removed to be washed and further treated as desired.

A process washing step recovers the hydrolysate from the cellulose. The washed cellulose is pulp that may be used for various purposes (e.g., paper or nanocellulose production). The weak hydrolysate from the washer continues to the final reaction step; in a continuous digestor this weak hydrolysate may be combined with the extracted hydrolysate from the external flash tank. In some embodiments, washing and/or separation of hydrolysate and cellulose-rich solids is conducted at a temperature of at least about 100° C., 110° C., or 120° C. The washed cellulose may also be used for glucose production via cellulose hydrolysis with enzymes or acids.

In another reaction step, the hydrolysate may be further treated in one or multiple steps to hydrolyze the oligomers into monomers. This step may be conducted before, during, or after the removal of solvent and sulfur dioxide. The solution may or may not contain residual solvent (e.g. alcohol). In some embodiments, sulfur dioxide is added or allowed to pass through to this step, to assist hydrolysis. In these or other embodiments, an acid such as sulfurous acid or sulfuric acid is introduced to assist with hydrolysis. In some embodiments, the hydrolysate is autohydrolyzed by heating under pressure. In some embodiments, no additional acid is introduced, but lignosulfonic acids produced during the initial cooking are effective to catalyze hydrolysis of hemicellulose oligomers to monomers. In various embodiments, this step utilizes sulfur dioxide, sulfurous acid, sulfuric acid at a concentration of about 0.01 wt % to 30 wt %, such as about 0.05 wt %, 0.1 wt %, 0.2 wt %, 0.5 wt %, 1 wt %, 2 wt %, 5 wt %, 10 wt %, or 20 wt %. This step may be carried out at a temperature from about 100° C. to 220° C., such as about 110° C., 120° C., 130° C., 140° C., 150° C., 160° C., 170° C., 180° C., 190° C., 200° C., or 210° C. Heating may be direct or indirect to reach the selected temperature.

The reaction step produces fermentable sugars which can then be concentrated by evaporation to a fermentation feedstock. Concentration by evaporation may be accomplished before, during, or after the treatment to hydrolyze oligomers. The final reaction step may optionally be followed by steam stripping of the resulting hydrolysate to remove and recover sulfur dioxide and alcohol, and for removal of potential fermentation-inhibiting side products. The evaporation process may be under vacuum or pressure, from about −0.1 bar to about 10 bar, such as about 0.1 bar, 0.3 bar, 0.5 bar, 1.0 bar, 1.5 bar, 2 bar, 4 bar, 6 bar, or 8 bar.

Recovering and recycling the sulfur dioxide may utilize separations such as, but not limited to, vapor-liquid disengagement (e.g. flashing), steam stripping, extraction, or combinations or multiple stages thereof. Various recycle ratios may be practiced, such as about 0.1, 0.2, 0.3, 0.4, 0.5, 0.6, 0.7, 0.8, 0.9, 0.95, or more. In some embodiments, about 90-99% of initially charged $SO_2$ is readily recovered by distillation from the liquid phase, with the remaining 1-10%

(e.g., about 3-5%) of the $SO_2$ primarily bound to dissolved lignin in the form of lignosulfonates.

In a preferred embodiment, the evaporation step utilizes an integrated alcohol stripper and evaporator. Evaporated vapor streams may be segregated so as to have different concentrations of organic compounds in different streams. Evaporator condensate streams may be segregated so as to have different concentrations of organic compounds in different streams. Alcohol may be recovered from the evaporation process by condensing the exhaust vapor and returning to the cooking liquor make-up vessel in the cooking step. Clean condensate from the evaporation process may be used in the washing step.

In some embodiments, an integrated alcohol stripper and evaporator system is employed, wherein aliphatic alcohol is removed by vapor stripping, the resulting stripper product stream is concentrated by evaporating water from the stream, and evaporated vapor is compressed using vapor compression and is reused to provide thermal energy.

The hydrolysate from the evaporation and final reaction step contains mainly fermentable sugars but may also contain lignin depending on the location of lignin separation in the overall process configuration. The hydrolysate may be concentrated to a concentration of about 5 wt % to about 60 wt % solids, such as about 10 wt %, 15 wt %, 20 wt %, 25 wt %, 30 wt %, 35 wt %, 40 wt %, 45 wt %, 50 wt % or 55 wt % solids. The hydrolysate contains fermentable sugars.

Fermentable sugars are defined as hydrolysis products of cellulose, galactoglucomannan, glucomannan, arabinoglucuronoxylans, arabinogalactan, and glucuronoxylans into their respective short-chained oligomers and monomer products, i.e., glucose, mannose, galactose, xylose, and arabinose. The fermentable sugars may be recovered in purified form, as a sugar slurry or dry sugar solids, for example. Any known technique may be employed to recover a slurry of sugars or to dry the solution to produce dry sugar solids.

In some embodiments, the fermentable sugars are fermented to produce biochemicals or biofuels such as (but by no means limited to) ethanol, isopropanol, acetone, 1-butanol, isobutanol, lactic acid, succinic acid, or any other fermentation products. Some amount of the fermentation product may be a microorganism or enzymes, which may be recovered if desired.

When the fermentation will employ bacteria, such as Clostridia bacteria, it is preferable to further process and condition the hydrolysate to raise pH and remove residual $SO_2$ and other fermentation inhibitors. The residual $SO_2$ (i.e., following removal of most of it by stripping) may be catalytically oxidized to convert residual sulfite ions to sulfate ions by oxidation. This oxidation may be accomplished by adding an oxidation catalyst, such as $FeSO_4·7H_2O$, that oxidizes sulfite ions to sulfate ions. Preferably, the residual $SO_2$ is reduced to less than about 100 ppm, 50 ppm, 25 ppm, 10 ppm, 5 ppm, or 1 ppm.

In some embodiments, the process further comprises recovering the lignin as a co-product. The sulfonated lignin may also be recovered as a co-product. In certain embodiments, the process further comprises combusting or gasifying the sulfonated lignin, recovering sulfur contained in the sulfonated lignin in a gas stream comprising reclaimed sulfur dioxide, and then recycling the reclaimed sulfur dioxide for reuse.

A lignin separation step may be utilized for the separation of lignin from the hydrolysate and can be located before or after the final reaction step and evaporation. If located after, then lignin will precipitate from the hydrolysate since alcohol has been removed in the evaporation step. The remaining water-soluble lignosulfonates may be precipitated by converting the hydrolysate to an alkaline condition (pH higher than 7) using, for example, an alkaline earth oxide, preferably calcium oxide (lime). The combined lignin and lignosulfonate precipitate may be filtered. The lignin and lignosulfonate filter cake may be dried as a co-product or burned or gasified for energy production. The hydrolysate from filtering may be recovered and sold as a concentrated sugar solution product or further processed in a subsequent fermentation or other reaction step.

Native (non-sulfonated) lignin is hydrophobic, while lignosulfonates are hydrophilic. Hydrophilic lignosulfonates may have less propensity to clump, agglomerate, and stick to surfaces. Even lignosulfonates that do undergo some condensation and increase of molecular weight, will still have an $HSO_3$ group that will contribute some solubility (hydrophilic).

In some embodiments, the soluble lignin precipitates from the hydrolysate after solvent has been removed in the evaporation step. In some embodiments, reactive lignosulfonates are selectively precipitated from hydrolysate using excess lime (or other base, such as ammonia) in the presence of aliphatic alcohol. In some embodiments, hydrated lime is used to precipitate lignosulfonates. In some embodiments, part of the lignin is precipitated in reactive form and the remaining lignin is sulfonated in water-soluble form.

The process may further include fermentation and distillation steps for the production of fermentation products, such as alcohols or organic acids. After removal of cooking chemicals and lignin, and further treatment (oligomer hydrolysis), the hydrolysate contains mainly fermentable sugars in water solution from which any fermentation inhibitors have been preferably removed or neutralized. The hydrolysate is fermented to produce dilute alcohol or organic acids, from 1 wt % to 20 wt % concentration. The dilute product is distilled or otherwise purified as is known in the art.

When alcohol is produced, such as ethanol, some of it may be used for cooking liquor makeup in the process cooking step. Also, in some embodiments, a distillation column stream, such as the bottoms, with or without evaporator condensate, may be reused to wash cellulose. In some embodiments, lime may be used to dehydrate product alcohol. Side products may be removed and recovered from the hydrolysate. These side products may be isolated by processing the vent from the final reaction step and/or the condensate from the evaporation step. Side products include furfural, hydroxymethylfurfural (IMEF), methanol, acetic acid, and lignin-derived compounds, for example.

The cellulose-rich material is highly reactive in the presence of industrial cellulase enzymes that efficiently break the cellulose down to glucose monomers. It has been found experimentally that the cellulose-rich material, which generally speaking is highly delignified, rapidly hydrolyzes to glucose with relatively low quantities of enzymes. For example, the cellulose-rich solids may be converted to glucose with at least 80% yield within 24 hours at 50° C. and 2 wt % solids, in the presence of a suitable cellulase enzyme mixture.

The glucose may be fermented to an alcohol, an organic acid, or another fermentation product. The glucose may be used as a sweetener or isomerized to enrich its fructose content. The glucose may be used to produce baker's yeast. The glucose may be catalytically or thermally converted to various organic acids and other materials.

In some embodiments, the cellulose-rich material is further processed into one more cellulose products. Cellulose products include market pulp, dissolving pulp (also known as α-cellulose), fluff pulp, nanocellulose, purified cellulose, paper, paper products, and so on. Further processing may include bleaching, if desired. Further processing may include modification of fiber length or particle size, such as when producing nanocellulose or nanofibrillated or microfibrillated cellulose. It is believed that the cellulose produced by this process is highly amenable to derivatization chemistry for cellulose derivatives and cellulose-based materials such as polymers.

When hemicellulose is present in the starting biomass, all or a portion of the liquid phase contains hemicellulose sugars and soluble oligomers. It is preferred to remove most of the lignin from the liquid, as described above, to produce a fermentation broth which will contain water, possibly some of the solvent for lignin, hemicellulose sugars, and various minor components from the digestion process. This fermentation broth can be used directly, combined with one or more other fermentation streams, or further treated. Further treatment can include sugar concentration by evaporation; addition of glucose or other sugars (optionally as obtained from cellulose saccharification); addition of various nutrients such as salts, vitamins, or trace elements; pH adjustment; and removal of fermentation inhibitors such as acetic acid and phenolic compounds. The choice of conditioning steps should be specific to the target product(s) and microorganism(s) employed.

In some embodiments, hemicellulose sugars are not fermented but rather are recovered and purified, stored, sold, or converted to a specialty product. Xylose, for example, can be converted into xylitol using known techniques. Xylose may be purified and sold as a sugar product.

In some embodiments, cellulose sugars (typically glucose) are not fermented but rather are recovered and purified, stored, sold, or converted to another product. The common isomer of glucose, D-glucose, is also known as dextrose. Glucose may be purified and sold as a dextrose product, for example. Dextrose is commonly commercially manufactured from corn starch, potato starch, wheat starch, or tapioca starch. An equivalent dextrose may be produced from lignocellulosic biomass, using processes disclosed herein.

D-glucose may also be enzymatically isomerized to L-glucose, which is an enantiomer of D-glucose that is indistinguishable in taste from D-glucose but cannot be used by humans as a source of energy because it cannot be phosphorylated by hexokinase, the first enzyme in the glycolysis pathway. For that reason, L-glucose may be used as an artificial sweetener in foods and beverages.

Glucose and other sugars may be converted to ethanol not by microbial fermentation, but rather using chemical catalysts. See, for example, U.S. Pat. No. 9,533,929 issued on Jan. 3, 2017 to Carter.

Glucose and other may sugars may be catalytically converted to hydrocarbons directly, rather than proceeding through fermentation to produce alcohols followed by alcohol dehydration and olefin oligomerization. For example, aqueous-phase heterogeneous reforming may be utilized to reduce the oxygen content of the feedstock. Reactions may include reforming to generate hydrogen, dehydrogenation of alcohols, hydrogenation of carbonyls, deoxygenation, hydrogenolysis, and cyclization. This process may be operated at temperatures of about 150-350 C and pressures of about 10-100 bar. An acid condensation reactor, using a ZSM-5 zeolite catalyst, may be used to produce hydrocarbon "drop-in" fuels, including jet fuel. The intermediate from catalytic conversion is sent to fractionation (typically, one or more distillation columns) where the intermediate is separated to various hydrocarbon fuel products, such as gasoline, diesel fuel, jet fuel, which may be referred to as sustainable gasoline, sustainable diesel fuel, and sustainable aviation fuel, respectively.

A lignin product can be readily obtained from a liquid phase using one or more of several methods. One simple technique is to evaporate off all liquid, resulting in a solid lignin-rich residue. This technique would be especially advantageous if the solvent for lignin is water-immiscible. Another method is to cause the lignin to precipitate out of solution. Some of the ways to precipitate the lignin include (1) removing the solvent for lignin from the liquid phase, but not the water, such as by selectively evaporating the solvent from the liquid phase until the lignin is no longer soluble; (2) diluting the liquid phase with water until the lignin is no longer soluble; and (3) adjusting the temperature and/or pH of the liquid phase. Methods such as centrifugation can then be utilized to capture the lignin. Yet another technique for removing the lignin is continuous liquid-liquid extraction to selectively remove the lignin from the liquid phase, followed by removal of the extraction solvent to recover relatively pure lignin.

Lignin produced in accordance with the invention can be used as a fuel. As a solid fuel, lignin is similar in energy content to coal. Lignin can act as an oxygenated component in liquid fuels, to enhance octane while meeting standards as a renewable fuel. The lignin produced herein can also be used as polymeric material, and as a chemical precursor for producing lignin derivatives. The sulfonated lignin may be sold as a lignosulfonate product, or burned for fuel value.

In various embodiments, the carbon intensity of a disclosed process is reduced, compared to a process that does not utilize this disclosure, by about, or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more, including any intervening ranges.

In various embodiments, the process water balance of a disclosed process is improved, compared to a process that does not utilize this disclosure, by about, or at least about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, or more, including any intervening ranges.

The present invention also provides systems configured for carrying out the disclosed processes, and compositions produced therefrom. Any stream generated by the disclosed processes may be partially or completed recovered, purified or further treated, and/or marketed or sold.

Any process described herein may be designed and operated as a system using known apparatus. A skilled engineer is able to design and build a system capable of carrying out a disclosed process. A system that is designed and constructed for the intended purpose of running a process disclosed herein, or otherwise taking advantage of one or more inventive concepts set forth herein, is regarded as enabled within the scope of this disclosure. In this sense, each of FIGS. 1 to 16, which depict processes, may also be considered to depict systems. All reference herein to a "stage" refers to a process stage, but also is understood to refer to a physical system stage that is capable of performing the steps of the process stage.

Materials of construction for the each unit may vary widely, depending on the process conditions. The invention is not necessarily limited to any particular materials of construction.

Some variations provide a system configured for carrying out a process for preparing a biomass feedstock for conversion to a sugar, a biofuel, a biochemical, or a biomaterial, the process comprising:
- (a) providing a biomass feedstock containing cellulose, hemicellulose, and lignin;
- (b) optionally, introducing the biomass feedstock and a first vapor stream to a biomass-heating unit, thereby generating a heated biomass stream;
- (c) introducing the biomass feedstock, or the heated biomass stream if step (b) is conducted, and a first liquid stream to a liquid-addition unit, thereby generating a wet biomass stream, wherein the first liquid stream contains a pretreatment chemical;
- (d) introducing the wet biomass stream to a mechanical conveyor operated to physically remove liquid from the wet biomass stream, thereby generating an excess-liquid stream comprising the pretreatment chemical and a solid discharge stream comprising the biomass feedstock and the pretreatment chemical;
- (e) recycling at least a portion of the excess-liquid stream to the first liquid stream; and
- (f) recovering or further processing the solid discharge stream.

Some variations provide a system configured for carrying out a process for converting a biomass feedstock into a pretreated biomass material, the process comprising:
- (a) providing a biomass feedstock containing cellulose, hemicellulose, and lignin;
- (b) introducing the biomass feedstock and a recycled vapor stream to a biomass-heating unit, thereby generating a heated biomass stream at a first temperature, wherein the recycled vapor stream is at a first pressure of at least atmospheric pressure;
- (c) feeding the heated biomass stream to a biomass digestor operated at a second temperature and a second pressure to pretreat the biomass feedstock, thereby generating a digested stream comprising a solid-liquid mixture and a digestor vapor, wherein the second temperature is higher than the first temperature, and wherein the second pressure is higher than the first pressure;
- (d) optionally recycling at least a portion of the digestor vapor to step (b), as some or all of the recycled vapor stream; and
- (e) recovering or further processing the solid-liquid mixture as a pretreated biomass material.

Some variations provide a system configured for carrying out a process for converting a biomass feedstock into a product, the process comprising:
- (a) providing a biomass feedstock containing cellulose, hemicellulose, and lignin;
- (b) providing a reaction solution comprising a fluid and optionally a pretreatment chemical;
- (c) feeding the biomass feedstock and the reaction solution to a biomass digestor operated to pretreat the biomass feedstock, thereby generating a digested stream comprising a solid-liquid mixture and a digestor vapor;
- (d) discharging the digested stream to a vapor-separation unit operated to separate the digestor vapor from the solid-liquid mixture;
- (e) optionally recycling at least a portion of the digestor vapor within the process;
- (f) conveying the solid-liquid mixture, or a portion thereof, to a hydrolysis reactor operated to hydrolyze the cellulose and/or the hemicellulose to monomeric and/or oligomeric sugars; and
- (g) converting the monomeric and/or oligomeric sugars to a product.

The present invention also provides one or more products, coproducts, and byproducts produced by a process as described. In preferred embodiments, a product comprises the fermentation product or a derivative thereof. In addition, an intermediate may be produced within a process, and recovered. For example, the intermediate may include purified fermentable sugars in dried form, crystallized form, pressed form, or slurried form.

Some variations provide a product produced by process comprising:
- (a) providing a biomass feedstock containing cellulose, hemicellulose, and lignin;
- (b) optionally, introducing the biomass feedstock and a first vapor stream to a biomass-heating unit, thereby generating a heated biomass stream;
- (c) introducing the biomass feedstock, or the heated biomass stream if step (b) is conducted, and a first liquid stream to a liquid-addition unit, thereby generating a wet biomass stream, wherein the first liquid stream contains a pretreatment chemical;
- (d) introducing the wet biomass stream to a mechanical conveyor operated to physically remove liquid from the wet biomass stream, thereby generating an excess-liquid stream comprising the pretreatment chemical and a solid discharge stream comprising the biomass feedstock and the pretreatment chemical;
- (e) recycling at least a portion of the excess-liquid stream to the first liquid stream; and
- (f) recovering or further processing the solid discharge stream.

Some variations provide a product produced by process comprising:
- (a) providing a biomass feedstock containing cellulose, hemicellulose, and lignin;
- (b) introducing the biomass feedstock and a recycled vapor stream to a biomass-heating unit, thereby generating a heated biomass stream at a first temperature, wherein the recycled vapor stream is at a first pressure of at least atmospheric pressure;
- (c) feeding the heated biomass stream to a biomass digestor operated at a second temperature and a second pressure to pretreat the biomass feedstock, thereby generating a digested stream comprising a solid-liquid mixture and a digestor vapor, wherein the second temperature is higher than the first temperature, and wherein the second pressure is higher than the first pressure;
- (d) optionally recycling at least a portion of the digestor vapor to step (b), as some or all of the recycled vapor stream; and
- (e) recovering or further processing the solid-liquid mixture as a pretreated biomass material.

Some variations provide a product produced by process comprising:
- (a) providing a biomass feedstock containing cellulose, hemicellulose, and lignin;
- (b) providing a reaction solution comprising a fluid and optionally a pretreatment chemical;
- (c) feeding the biomass feedstock and the reaction solution to a biomass digestor operated to pretreat the biomass feedstock, thereby generating a digested stream comprising a solid-liquid mixture and a digestor vapor;

(d) discharging the digested stream to a vapor-separation unit operated to separate the digestor vapor from the solid-liquid mixture;
(e) optionally recycling at least a portion of the digestor vapor within the process;
(f) conveying the solid-liquid mixture, or a portion thereof, to a hydrolysis reactor operated to hydrolyze the cellulose and/or the hemicellulose to monomeric and/or oligomeric sugars; and
(g) converting the monomeric and/or oligomeric sugars to a product.

Some embodiments incorporate a process-control system configured for automatically controlling a unit, such as a vapor-separation unit or a digestor. The process-control system may utilize artificial intelligence, such as a machine-learning algorithm, a deep-learning algorithm, a neural networks, or a combination thereof.

Some embodiments utilize a business system in which steps of a selected process are practiced at different sites and potentially by different corporate entities, acting in conjunction with each other in some manner, such as in a joint venture, an agency relationship, a toll producer, a customer with restricted use of product, etc. For example, biomass may be pretreated at a first site to generate a pretreated biomass material that is then sent to a second site for further processing.

The recited process and system options, and process and system embodiments, may be utilized entirely or partially. Some embodiments may omit process steps or system components. Some embodiments include other process steps or system components that are not explicitly taught herein but are conventional in the chemical-engineering and biorefinery arts. Solid, liquid, and gas streams produced or existing within the process can be independently recycled, passed to subsequent steps, or removed/purged from the process at any point.

The throughput, or process capacity, can vary widely from small experimental units to full operations, including any pilot, demonstration, or semi-commercial scale. In various embodiments, the process capacity (for feedstocks, products, or both) is at least about 0.1 tons/day (all tons are metric tons), 1 ton/day, 10 tons/day, 100 tons/day, 500 tons/day, 1000 tons/day, 2000 tons/day, or higher.

The biorefinery may be a retrofit to an existing plant. In other embodiments, the biorefinery is a greenfield plant. As will be appreciated by a person skilled in the art, the principles of this disclosure may be applied to many biorefinery plant configurations beyond those explicitly disclosed or described in the drawings hereto. Various combinations are possible and selected embodiments from some variations may be utilized or adapted to arrive at additional variations that do not necessarily include all features disclosed herein.

This disclosure also hereby incorporates by reference herein U.S. Patent App. Pub. No. 2021/013103 by Zebroski, published May 6, 2021, for its teachings of various process options that may be applicable to embodiments of this invention. U.S. Patent App. Pub. No. 2021/013103 discloses, among other things, a pre-impregnation process that removes non-condensable gases. The present invention may be utilized for pre-steaming and improving the overall environmental footprint of the process, recognizing that pre-steaming may, or may not, remove non-condensable gases from biomass pores. In addition, in the present invention, a separate liquid solution may, or may not, be introduced to pre-steamed biomass and/or to biomass being fed to, or contained in, a digestor.

In this detailed description, reference has been made to multiple embodiments of the invention and non-limiting examples relating to how the invention can be understood and practiced. Other embodiments that do not provide all of the features and advantages set forth herein may be utilized, without departing from the spirit and scope of the present invention. This invention incorporates routine experimentation and optimization of the methods and systems described herein. Such modifications and variations are considered to be within the scope of the invention defined by the claims. The headings in the detailed description shall not be construed as limiting the invention.

All publications, patents, and patent applications cited in this specification are herein incorporated by reference in their entirety as if each publication, patent, or patent application were specifically and individually put forth herein. In case of conflict between text that is explicitly set forth herein and information that is incorporated by reference, the explicit text in this patent application shall control over the text incorporated by reference.

Where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially.

Therefore, to the extent there are variations of the invention, which are within the spirit of the disclosure or equivalent to the inventions found in the appended claims, it is the intent that this patent will cover those variations as well. The present invention shall only be limited by what is claimed.

EXAMPLE

| Eucalyptus as biomass feedstock is provides with a normalized composition as follows: | |
| --- | --- |
| Glucan ($C_6$) | 44.7 wt % |
| Xylan ($C_5$) | 12.7 wt % |
| Galactan ($C_6$) | 2.2 wt % |
| Arabinan ($C_5$) | 0.4 wt % |
| Mannan ($C_6$) | 1.2 wt % |
| Acetyl | 1.5 wt % |
| Lignin | 24.2 wt % |
| Extractives | 7.4 wt % |
| Silica and Other | 5.7 wt % |

The biomass feedstock is first pre-steamed at atmospheric pressure for 30 minutes to heat the biomass, prepare the biomass for liquid impregnation, and remove non-condensable gases. The biomass feedstock is then immediately immersed in an impregnation liquid containing water and sulfuric acid ($H_2SO_4$). The target acid dose applied to the *eucalyptus* is 0.003-0.010 g sulfuric acid per g dry *eucalyptus*. The impregnated material is then digested in a thermal digestor at a temperature of 160° C. for a duration of 5 minutes, to form a digested material.

The digested material is then subjected to enzymatic hydrolysis. The slurry concentration is about 2 wt % total solids. A commercially available enzyme cocktail is used, at an enzyme dose of about 3 mg protein per g dry pretreated material. The pH during enzymatic hydrolysis is in the 4.7-5.4 range. The temperature during enzymatic hydrolysis is in the 50-55° C. range, and the hydrolysis is carried out for 72 hours to obtain a liquid hydrolysate.

For the pre-steamed and immersed *eucalyptus* described above, about 57.5% of the *eucalyptus* carbohydrate is recovered as monosaccharide at the end of enzymatic hydrolysis. For a control sample of *eucalyptus* that is immersed, but not pre-steamed, about 32.7% of the *eucalyptus* carbohydrate is recovered as monosaccharide at the end of enzymatic hydrolysis under the same conditions. The result is a greater than 40% increase in the conversion of *eucalyptus* carbohydrate to monosaccharide.

What is claimed is:

1. A process for converting a biomass feedstock into a pretreated biomass material, said process comprising:
   (a) providing a biomass feedstock containing cellulose, hemicellulose, and lignin;
   (b) introducing said biomass feedstock and a first vapor stream to a biomass-heating unit, thereby generating a heated biomass stream at a first temperature, wherein said first vapor stream is at a first pressure selected from about 0 barg to about 5 barg;
   (c) feeding said heated biomass stream to a biomass digestor operated at a second temperature and a second pressure to pretreat said biomass feedstock, thereby generating a digested stream comprising a solid-liquid mixture and a digestor vapor, wherein said second temperature is higher than said first temperature, and wherein said second pressure is higher than said first pressure; and
   (d) recovering or further processing said solid-liquid mixture as a pretreated biomass material.

2. The process of claim 1, wherein said first pressure is greater than atmospheric pressure.

3. The process of claim 1, wherein said first temperature is selected from about 50° C. to about 150° C.

4. The process of claim 1, wherein said second temperature is selected from about 100° C. to about 220° C.

5. The process of claim 1, wherein said second pressure is selected from about 1 barg to about 25 barg.

6. The process of claim 1, wherein said first vapor stream is clean steam that does not contain acetic acid, formic acid, formaldehyde, acetaldehyde, methanol, lactic acid, furfural, 5-hydroxymethylfurfural, furans, uronic acids, phenolic compounds, terpenes, sulfur-containing compounds, residual biomass particles, cellulose, lignin, monosaccharides, polysaccharides, or ash.

7. The process of claim 1, wherein said first vapor stream is selected from the group consisting of a process vapor stream, a utility vapor stream, a vapor stream obtained from an adjacent facility or process, and combinations thereof.

8. The process of claim 1, wherein said first vapor stream is contaminated steam that contains a vapor-phase contaminant selected from the group consisting of acetic acid, formic acid, formaldehyde, acetaldehyde, methanol, lactic acid, furfural, 5-hydroxymethylfurfural, furans, uronic acids, phenolic compounds, terpenes, sulfur-containing compounds, residual biomass particles, cellulose, lignin, monosaccharides, polysaccharides, ash, and combinations thereof.

9. The process of claim 1, wherein said first vapor stream contains a pretreatment chemical, and wherein said pretreatment chemical is optionally acetic acid, formic acid, or a combination thereof.

10. The process of claim 1, wherein said digested stream is fed to a mechanical refiner.

11. The process of claim 1, wherein said digestor vapor is separated from said solid-liquid mixture.

12. The process of claim 11, wherein said solid-liquid mixture is fed to a mechanical refiner, and wherein said mechanical refiner is selected from the group consisting of a hot-blow refiner, a hot-stock refiner, a blow-line refiner, a disk refiner, a conical refiner, a cylindrical refiner, an in-line defibrator, an extruder, a homogenizer, and combinations thereof.

13. The process of claim 11, wherein said solid-liquid mixture is divided into a solid-rich stream and a liquid-rich stream, wherein said solid-rich stream is optionally fed to a mechanical refiner, and wherein said mechanical refiner is selected from the group consisting of a hot-blow refiner, a hot-stock refiner, a blow-line refiner, a disk refiner, a conical refiner, a cylindrical refiner, an in-line defibrator, an extruder, a homogenizer, and combinations thereof.

14. The process of claim 1, wherein said solid-liquid mixture is processed to hydrolyze said cellulose and/or said hemicellulose to monomeric and/or oligomeric sugars.

\* \* \* \* \*